US010150801B1

(12) United States Patent
Chen et al.

(10) Patent No.: US 10,150,801 B1
(45) Date of Patent: Dec. 11, 2018

(54) RECOMBINANT POLYPEPTIDES AND METHODS OF USE THEREOF

(71) Applicant: Imunami Laboratories Pte. Ltd., Singapore (SG)

(72) Inventors: Ya-Huei Chen, Singapore (SG); Ting-Long Lin, Singapore (SG)

(73) Assignee: Imunami Laboratories Pte. Ltd., Singapore (SG)

( * ) Notice: Subject to any disclaimer, the term of this patent is extended or adjusted under 35 U.S.C. 154(b) by 0 days.

(21) Appl. No.: 15/854,906

(22) Filed: Dec. 27, 2017

(51) Int. Cl.
*C07K 14/465* (2006.01)
*A61P 35/00* (2006.01)
*A61K 38/00* (2006.01)

(52) U.S. Cl.
CPC ............ *C07K 14/465* (2013.01); *A61P 35/00* (2018.01); *A61K 38/00* (2013.01)

(58) Field of Classification Search
None
See application file for complete search history.

(56) References Cited

U.S. PATENT DOCUMENTS

| | | |
|---|---|---|
| 4,579,821 A | 4/1986 | Palmiter et al. |
| 4,599,311 A | 7/1986 | Kawasaki |
| 4,601,978 A | 7/1986 | Karin |
| 4,615,974 A | 10/1986 | Kingsman et al. |
| 4,656,134 A | 4/1987 | Ringold |
| 4,661,454 A | 4/1987 | Botstein et al. |
| 4,713,339 A | 12/1987 | Levinson et al. |
| 4,784,950 A | 11/1988 | Hagen et al. |
| 4,845,075 A | 7/1989 | Murray et al. |
| 4,870,008 A | 9/1989 | Brake |
| 4,882,279 A | 11/1989 | Cregg |
| 4,931,373 A | 6/1990 | Kawasaki et al. |
| 4,935,349 A | 6/1990 | McKnight et al. |
| 4,956,288 A | 9/1990 | Barsoum |
| 4,977,092 A | 12/1990 | Bitter |
| 4,990,446 A | 2/1991 | Oberto et al. |
| 5,037,743 A | 8/1991 | Welch et al. |
| 5,063,154 A | 11/1991 | Fink et al. |
| 5,139,936 A | 8/1992 | Botstein et al. |
| 5,143,830 A | 9/1992 | Holland et al. |
| 5,162,222 A | 11/1992 | Guarino et al. |
| 5,162,228 A | 11/1992 | Sumino et al. |
| 5,300,435 A | 4/1994 | Granados |
| 5,716,808 A | 2/1998 | Raymond |
| 5,736,383 A | 4/1998 | Raymond |
| 5,854,039 A | 12/1998 | Raymond et al. |
| 5,888,768 A | 3/1999 | Raymond |

FOREIGN PATENT DOCUMENTS

| | | |
|---|---|---|
| WO | WO 94/06463 A1 | 3/1994 |
| WO | WO 2013/174510 A1 | 11/2013 |

OTHER PUBLICATIONS

NCBI Blast Protein Sequence, SEQ ID No. 9, six pages (Jun. 19, 2018).*
NCBI Accession No. XP_013036875.1, Jul. 24, 2015.
Andley, U. P. et al., "Differential Protective Activity of αA- and αB-crystallin in Lens Epithelial Cells," The Journal of Biological Chemistry, vol. 275, No. 47, pp. 36823-36831 (2000).
Basu, S. et al., "Calreticulin, a Peptide-binding Chaperone of the Endoplasmic Reticulum, Elicits Tumor- and Peptide-specific Immunity," J. Exp. Med., vol. 189, No. 5, pp. 797-802 (1999).
Basu, S. et al., "CD91 Is a Common Receptor for Heat Shock Proteins gp96, hsp90, hsp70, and Calreticulin," Immunity, vol. 14, pp. 303-313 (2001).
Binder, R. J. et al., "Peptides chaperoned by heat-shock proteins are a necessary and sufficient source of antigen in the cross-priming of $CD8^+T$ cells," Nature Immunology, vol. 6, No. 6, pp. 593-599 (2005).
Blay, J. -Y. et al., "Early Lymphopenia After Cytotoxic Chemotherapy as a Risk Factor for Febrile Neutropenia," Journal of Clinical Oncology, vol. 14, No. 2, pp. 636-643 (1996).
Bonning, B. C. et al., "Superior expression of juvenile hormone esterase and β-galactosidase from the basic protein promoter of *Autographa californica* nuclear polyhedrosis virus compared to the p10 protein and polyhedrin promoters," Journal of General Virology, 75, pp. 1551-1556 (1994).
Campbell, A. C. et al., "Characteristics of the lymphopenia induced by radiotherapy," Clin. exp. Immunol., 23, pp. 200-208 (1976).
Carreno, B. M. et al., "A dendritic cell vaccine increases the breadth and diversity of melanoma neoantigen-specific T cells," Science, vol. 348, No. 6239, pp. 803-808 (2015) and Supplementary Materials, 27 pages.
Chazenbalk, G. D. et al., "Expression of the Extracellular Domain of the Thyrotropin Receptor in the Baculovirus System Using a Promoter Active Earlier than the Polyhedrin Promoter," The Journal of Biological Chemistry, vol. 270, No. 4, pp. 1543-1549 (1995).
Corsaro, C. M. et al., "Enhancing the Efficiency of DNA-Mediated Gene Transfer in Mammalian Cells," Somatic Cell Genetics, vol. 7, No. 5, pp. 603-616 (1981).
Drocourt, D. et al., "Cassettes of the *Streptoalloteichus hindustanus ble* gene for transformation of lower and higher eukaryotes to phleomycin resistance," Nucleic Acids Research, vol. 18, No. 13, p. 4009 (1990).
Franěk, F. et al., "Protection of B lymphocyte hybridoma against starvation-induced apoptosis: survival-signal role of some amino acids," Immunology Letters, 52, pp. 139-144 (1996).

(Continued)

*Primary Examiner* — Alana Harris Dent
(74) *Attorney, Agent, or Firm* — Cooley LLP; Matthew Pavao

(57) ABSTRACT

The present disclosure provides recombinant polypeptides, nucleic acids encoding the recombinant polypeptides and methods for using these polypeptides and/or nucleic acids in enhancing or inducing an immune response in a subject in need thereof. The present disclosure also provides methods of treating a cell proliferative disorder, such as cancer, by administering the disclosed polypeptides and/or nucleic acids to a subject in need thereof.

3 Claims, 34 Drawing Sheets

Specification includes a Sequence Listing.

(56) References Cited

OTHER PUBLICATIONS

Gatignol, A. et al., "Phleomycin resistance encoded by the ble gene from transposon Tn 5 as a dominant selectable marker in *Saccharomyces cerevisiae*," Mol. Gen. Genet., 207, pp. 342-348 (1987).
GenBank Accession No. AAA28635.1, Jun. 10, 2016.
GenBank Accession No. AAA28637.1, Jun. 10, 2016.
GenBank Accession No. AAH69528.1, Jul. 15, 2006.
GenBank Accession No. O12984.1, Feb. 28, 2018.
GenBank Accession No. P02505.1, Oct. 25, 2017.
GenBank Accession No. Q05557.1, Feb. 28, 2018.
GenBank Accession No. XP013036875.1, Jul. 24, 2015.
GenBank Accession No. XP013042703.1, Jul. 24, 2015.
Gerweck, L. E. et al., "Cellular pH Gradient in Tumor versus Normal Tissue: Potential Exploitation for the Treatment of Cancer," Cancer Research, 56, pp. 1194-1198 (1996).
Gillies, R. J. et al., "Evolutionary dynamics of carcinogens and why targeted therapy does not work," Nature Reviews, vol. 12, pp. 487-493 (2012).
Gleeson, M. A. et al., "Transformation of the Methylotrophic Yeast *Hansenula polymorpha*," Journal of General Microbiology, 132, pp. 3459-3465 (1986).
Graham, F. L. et al., "A New Technique for the Assay of Infectivity of Human Adenovirus 5 DNA," Virology, 52, pp. 456-467 (1973).
Hill-Perkins, M. S. et al., "A baculovirus expression vector derived from the basic protein promoter of *Autographa californica* nuclear polyhedrosis virus," Journal of General Virology, 71, pp. 971-976 (1990).
Ingolia, T. D. et al., "Four small *Drosophila* heat shock proteins are related to each other and to mammalian α-crystallin," Proc. Natl. Acad. Sci. USA, vol. 79, pp. 2360-2364 (1982).
Ishii, T. et al., "Isolation of MHC Class I-Restricted Tumor Antigen Peptide and its Precursors Associated with Heat Shock Proteins hsp70, hsp90, and gp96," J. Immunol., 162, pp. 1303-1309 (1999).
Jolles, C. J. et al., "Systemic immunosuppression induced by peritoneal photodynamic therapy," Am. J. Obstet. Gynecol., vol. 158, No. 6, Part 1, pp. 1446-1452 (1988).
Krysko, D. V. et al., "Immunogenic cell death and DAMPs in cancer therapy," Nature Reviews, vol. 12, pp. 860-875 (2012).
Li, Y. et al., "Selective killing of cancer cells by β-lapachone: Direct checkpoint activation as a strategy against cancer," PNAS, vol. 100, No. 5, pp. 2674-2678 (2003).
Luckow, V. A. et al., "Efficient Generation of Infectious Recombinant Baculoviruses by Site-Specific Transposon-Mediated Insertion of Foreign Genes into a Baculovirus Genome Propagated in *Escherichia coli*," Journal of Virology, vol. 67, No. 8, pp. 4566-4579 (1993).
Malin, D. et al., "αB-Crystallin: A Novel Regulator of Breast Cancer Metastasis to the Brain," Clinical Cancer Research, http://clincancerres.aacrjournals.org/; doi:10.1158/1078-0432.CCR-13-1255, 13 pages (2013).
Moyano, J. V. et al., "αB-Crystallin is a novel oncoprotein that predicts poor clinical outcome in breast cancer," The Journal of Clinical Investigation, vol. 116, No. 1, pp. 261-270 (2006).
Neumann, E. et al., "Gene transfer into mouse lyoma cells by electroporation in high electric fields," The EMBO Journal, vol. 1, No. 7, pp. 841-845 (1982).
Obeid, M. et al., "Calreticulin exposure dictates the immunogenicity of cancer cell death," Nature Medicine, vol. 13, No. 1, pp. 54-61 (2007).
Pasupuleti, N. et al., "The anti-apoptotic function of human αA-crystallin is directly related to its chaperone activity," Cell Death and Disease, 1, e31, doi:10.1038/cddis.2010.3, 12 pages (2010).
Penjweini, R. et al., "Optimizing the antitumor selectivity of PVP-Hypericin re A546 cancer cells and HLF normal cells through pulsed blue light," Photodiagnosis and Photodynamic Therapy, 10, pp. 591-599 (2013).
Photodynamic Therapy for Cancer, National Cancer Institute, https://www.cancer.gov/about-cancer/treatment/types/surgery/photodynamic-fact-sheet#r3, 3 pages (2011).
Raghunand, N. et al., "pH and drug resistance in tumors," Drug Resistance Updates, 3, pp. 39-47 (2000).
Raymond, C. K. et al., "Development of the Methylotrophic Yeast *Pichia methanolica* for the Expression of the 65 Kilodalton Isoform of Human Glutamate Decarboxylase," Yeast, vol. 14, pp. 11-23 (1998).
Savill, J., "Recognition and phagocytosis of cells undergoing apoptosis," British Medical Bulletin, vol. 53, No. 3, pp. 491-508 (1997).
Sinkar, V. P. et al., "Molecular biology of RI-plasmid—A review," J. Biosci., vol. 11, Nos. 1-4, pp. 47-57 (1987).
Trédan, O. et al., "Drug Resistance and the Solid Tumor Microenvironment," JNCI, vol. 99, No. 19, pp. 1441-1454 (2007).
Urlaub, G. et al., "Effect of Gamma Rays at the Dihydrofolate Reductase Locus: Deletions and Inversions," Somatic Cell and Molecular Genetics, vol. 12, No. 6, pp. 555-566 (1986).
Wakshlag, J. J. et al., "The Effects of Branched-Chain Amino Acids on Canine Neoplastic Cell Proliferation and Death," J. Nutrition, 136, pp. 2007S-2010S (2006).
Wigler, M. et al., "Biochemical Transfer of Single-Copy Eucaryotic Genes Using total Cellular DNA as Donor," Cell, vol. 14, pp. 725-731 (1978).
Yadav, M. et al., "Predicting immunogenic tumour mutations by combining mass spectrometry and exome sequencing," Nature, vol. 515, pp. 572-576 and Supplementary Materials, 7 pages (2014).
Yang, L. et al., "Improvement of the viability of cultured rat neurons by the non-essential amino acids L-serine and glycine that upregulates expression of the anti-apoptotic gene product Bcl-w," Neuroscience Letters, 295, pp. 97-100 (2000).

\* cited by examiner

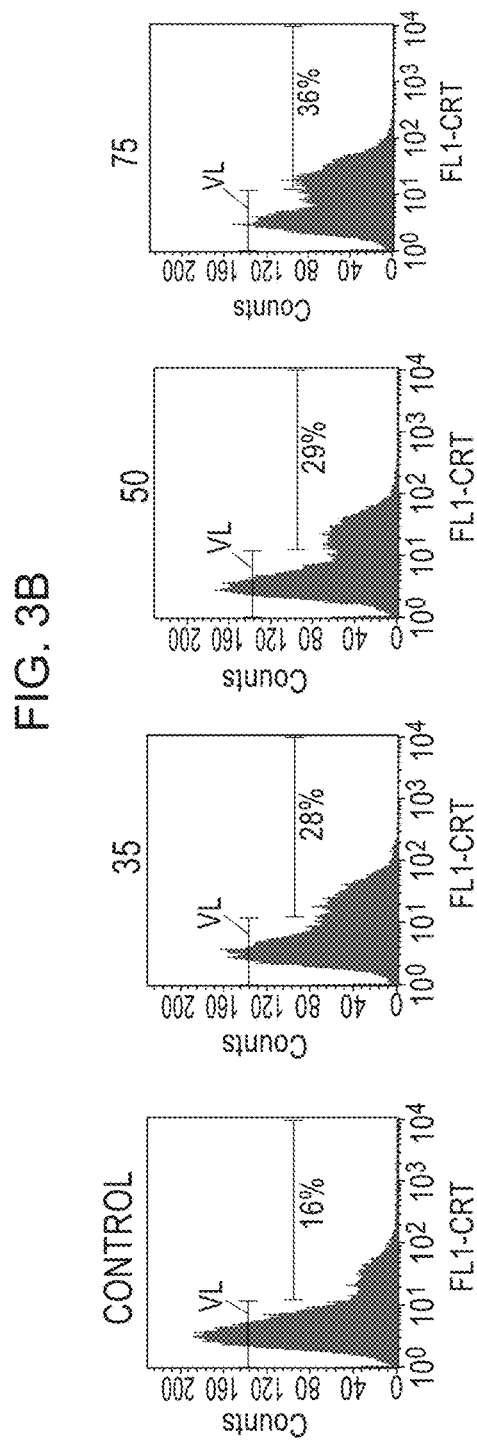

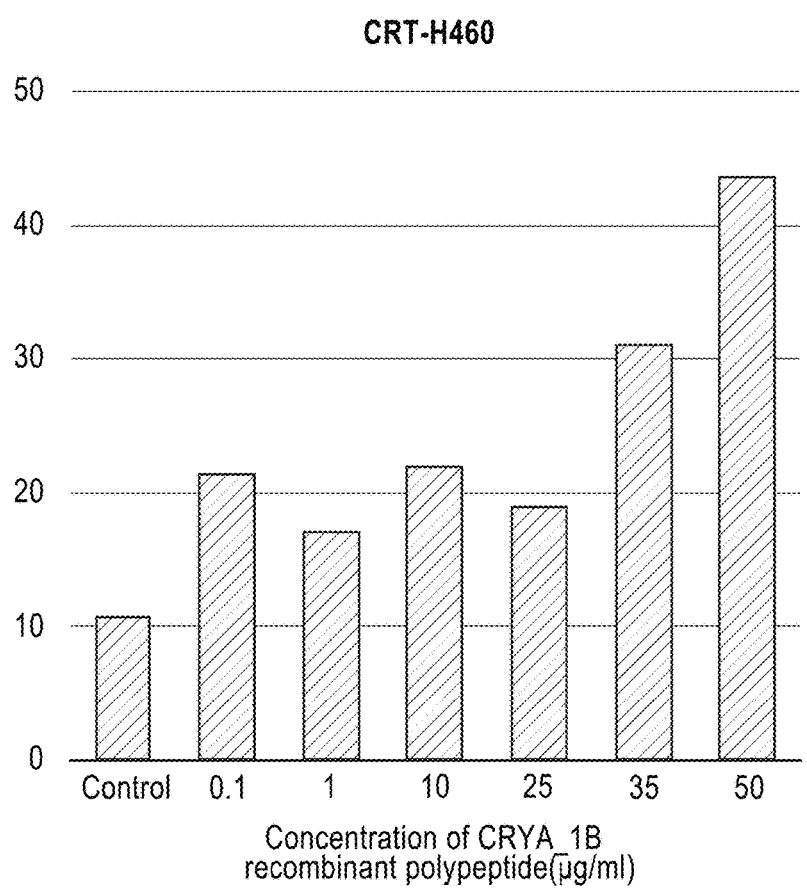

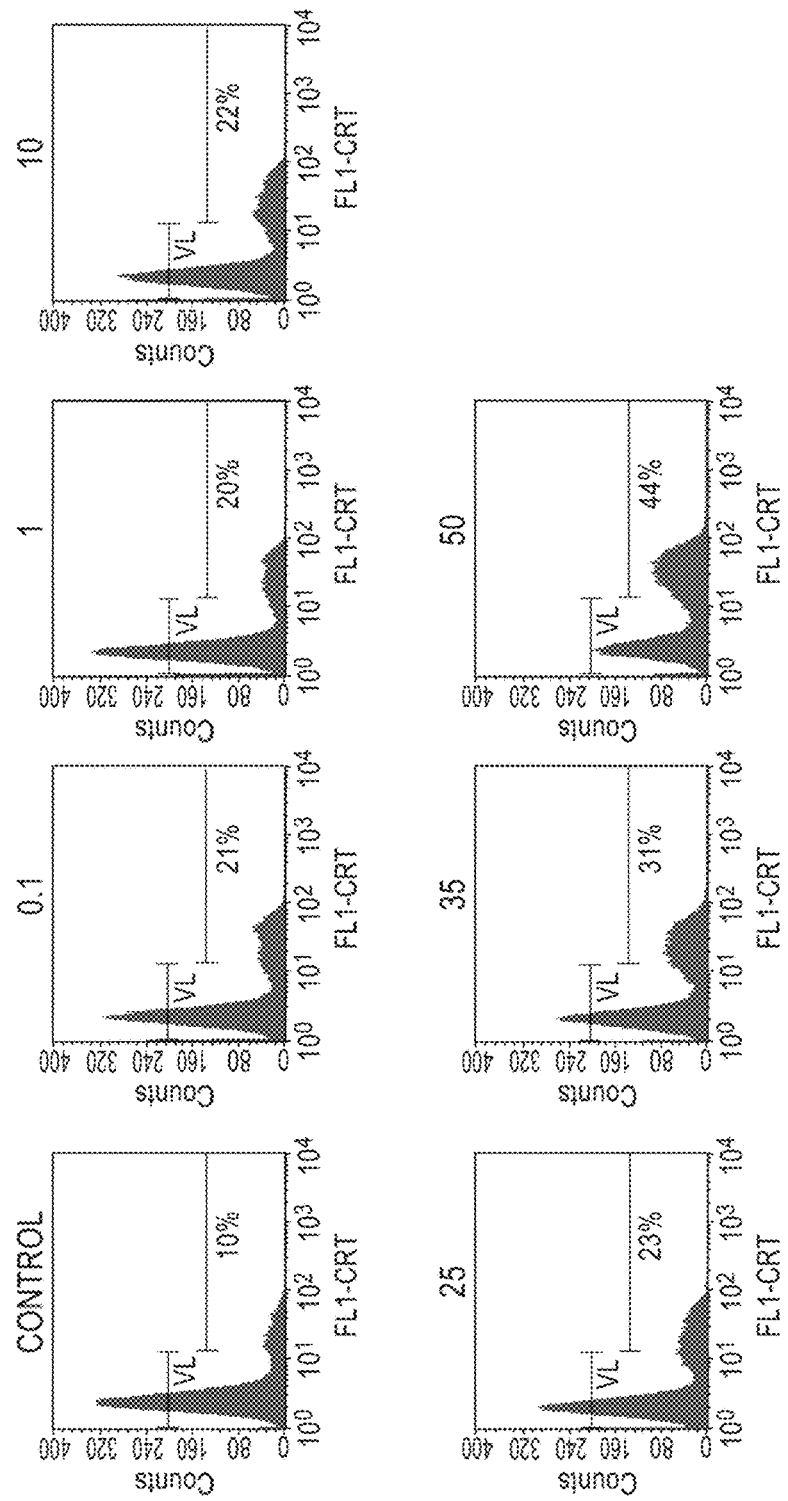

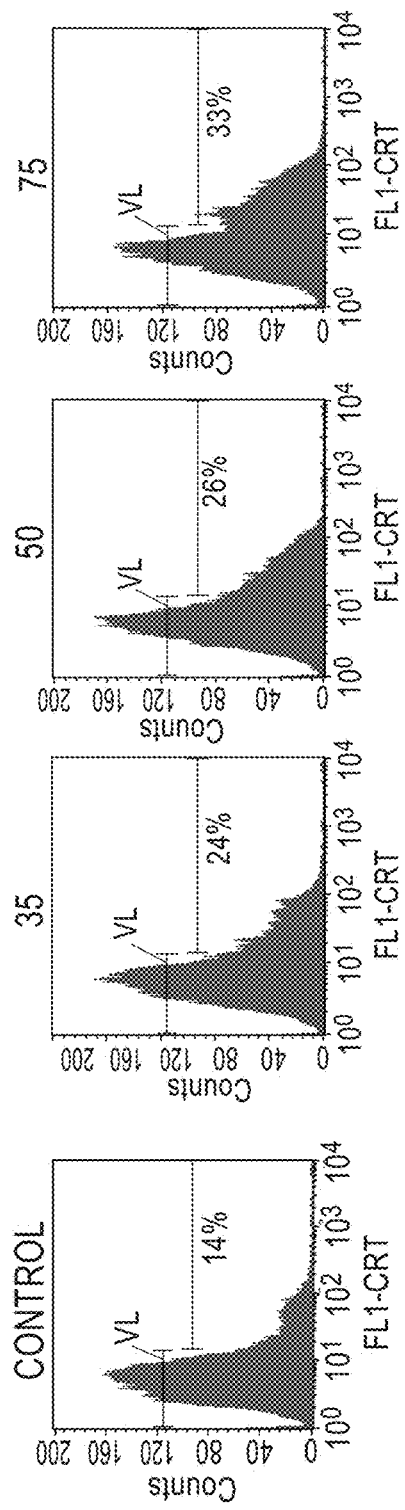

FIG. 7A

Hsp70-H441

Concentration of CRYA_1B recombinant polypeptide (μg/ml): Control, 35, 50, 75

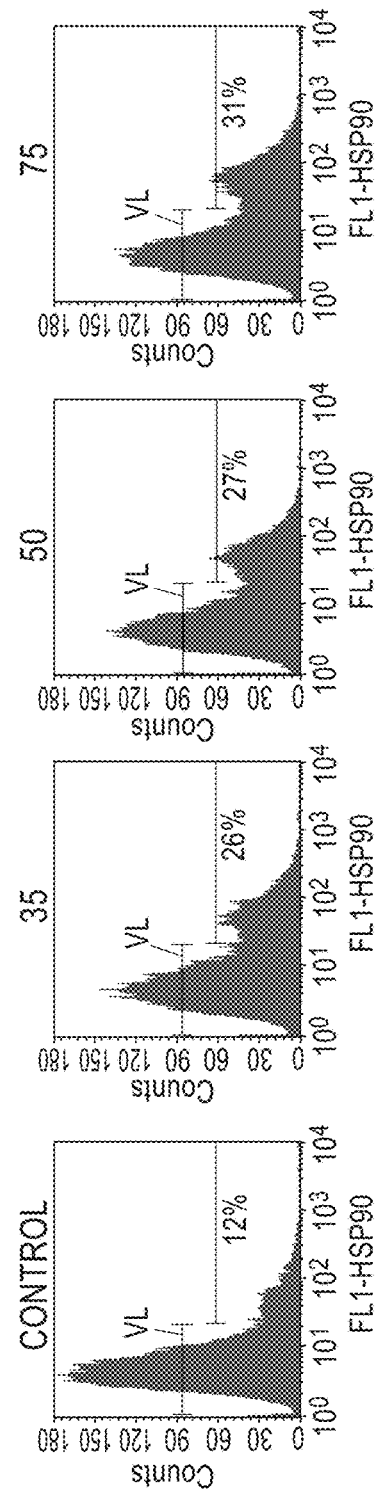

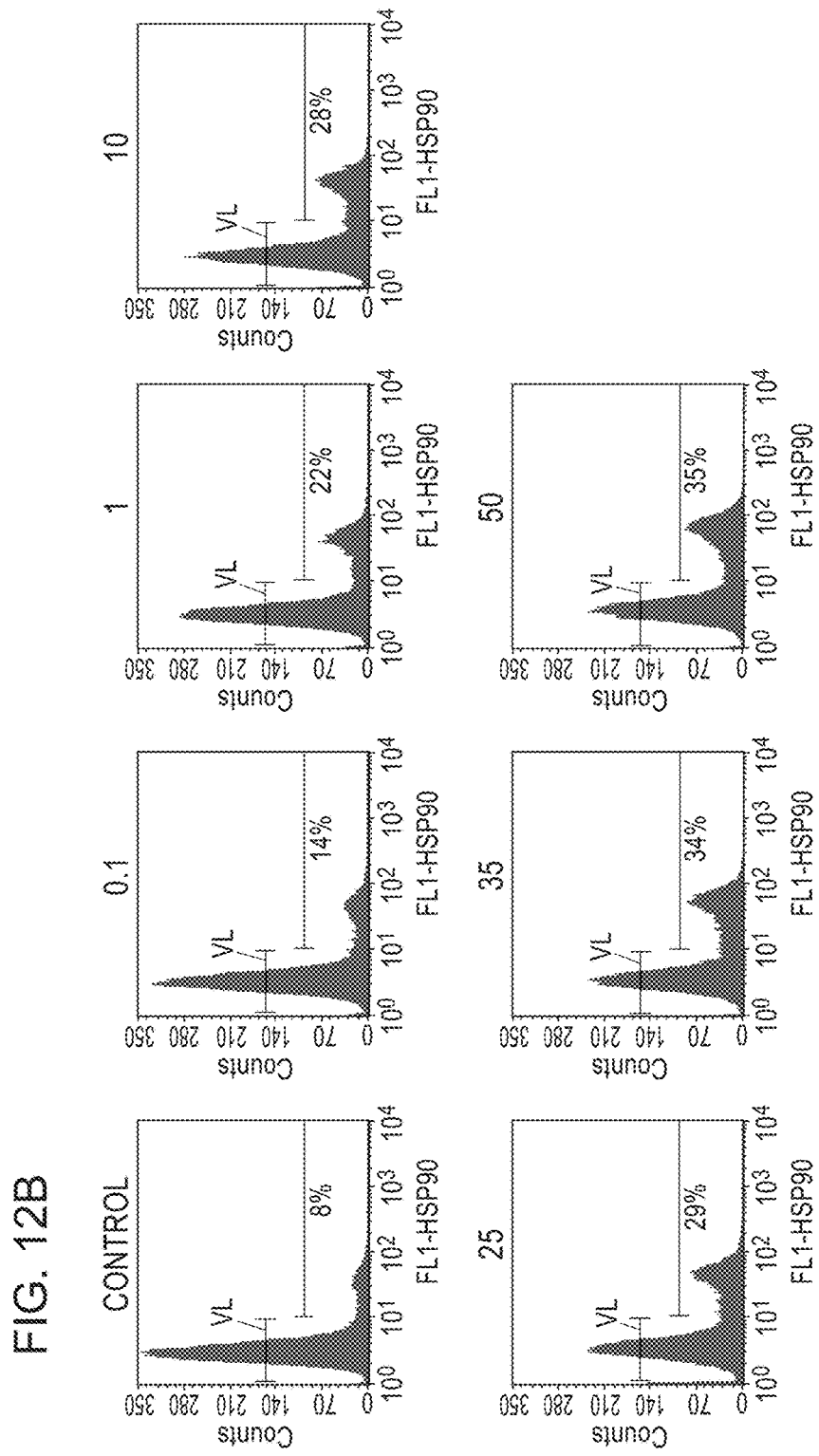

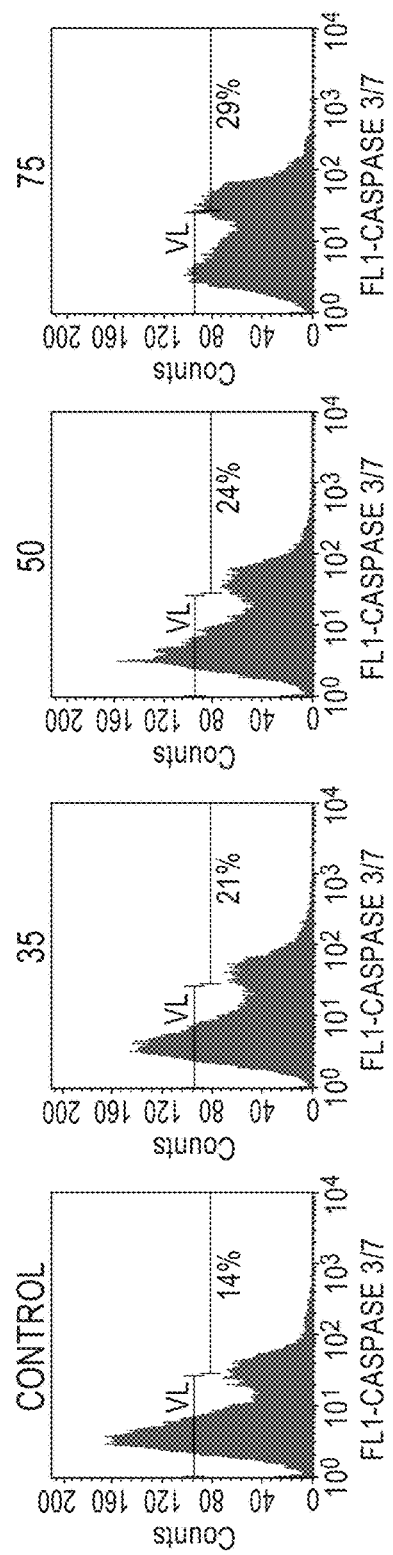

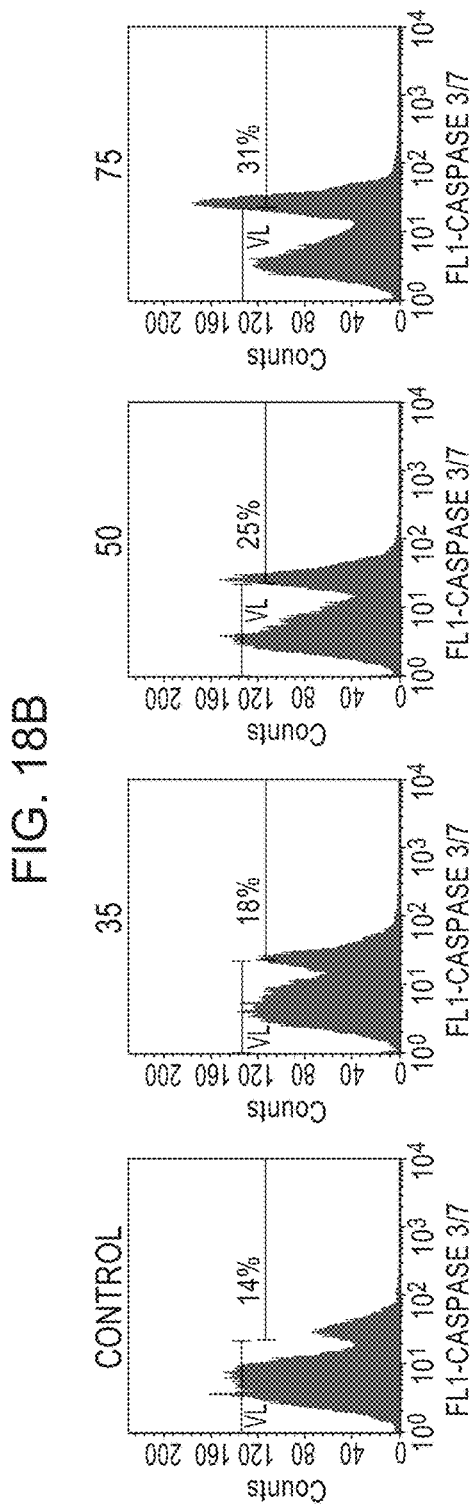

RECOMBINANT POLYPEPTIDES AND METHODS OF USE THEREOF

SEQUENCE LISTING

The instant application contains a Sequence Listing which has been submitted in ASCII format via EFS-Web and is hereby incorporated by reference in its entirety. Said ASCII copy, created on Nov. 21, 2017, is named IMHC-001/F01US_ST25.txt and is 42 KB in size.

BACKGROUND OF THE INVENTION

Immunogenic cell death is a form of cell death or apoptosis. Unlike traditional apoptosis, which is mostly non-immunogenic, immunogenic cell death in cancer cells can induce an effective anti-tumor immune response through the activation of dendritic cells. The pre-apoptotic state is defined as the state before the activation of Caspase 3/7, the manifestation of cell apoptosis. Immunogenic cell death is characterized by the expression of pre-apoptotic damage-associated-molecular-patterns (DAMPs) on the surface of a dying cell. There are three important pre-apoptotic DAMPs which are exposed to the cell surface during immunogenic cell death: calreticulin (CRT), HSP70 and HSP90. These three pre-apoptotic DAMP signals play an important role in dendritic cell recruitment and cell phagocytosis by CRT and dendritic cell maturation/activation by HSP70 and HSP90, resulting in effective anti-tumor immune response. Selected forms of chemotherapy and radiotherapy can induce collateral immunogenic cell death. While these therapies can induce one or two of the three pre-apoptotic DAMP signals, they do not induce the expression of all three pre-apoptotic DAMP signals. Furthermore, chemotherapy and radiotherapy are immunosuppressive therapies, which reduce numbers of lymphocytes and also cause collateral damages to surrounding non-tumor cells, resulting in poor anti-tumor immune responses and also adverse events respectively.

There is a need for compositions that induce immunogenic cell death with increased efficiency and potency by inducing the expression of all three pre-apoptotic DAMP signals, while minimizing adverse effects. The present disclosure addresses this need.

SUMMARY OF THE INVENTION

The present disclosure provides acidic recombinant polypeptides.

The present disclosure provides recombinant polypeptides comprising, consisting essentially of, or consisting of, an amino acid sequence selected from the group consisting of SEQ ID NO: 1-16 or an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences of SEQ ID NO: 1-16. In one aspect, the recombinant polypeptides comprise, consist essentially of, or consist of an amino acid sequence selected from the group consisting of SEQ ID NO: 1-8 or an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences of SEQ ID NO: 1-8. In one aspect, the recombinant polypeptides comprise, consist essentially of, or consist of an amino acid sequence selected from the group consisting of SEQ ID NO: 9-16 or an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences of SEQ ID NO: 9-16. In a preferred aspect, the recombinant polypeptide comprises, consists essentially of, or consists of an amino acid sequence of SEQ ID NO: 9 or amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences of SEQ ID NO: 9.

In one aspect, the recombinant polypeptides comprise, consist essentially of, or consist of an amino acid sequence selected from the group consisting of SEQ ID NO: 1-16 or amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences of SEQ ID NO: 1-16 that are acidic recombinant polypeptides as determined by pI. In one aspect, the pI of the recombinant polypeptide is lower than the pI of SEQ ID NO: 1-16. In one aspect, aspartic acid (D), glutamic acid (E) and leucine (L) are each independently present in an amount greater than, or equal to, the amount of any other amino acid residue present within the recombinant polypeptide sequence. In one aspect, the amino acid sequence of the acidic recombinant polypeptides comprise aspartic acid (D), glutamic acid (E) and leucine (L) as the three most abundant residues within the amino acid sequence or as greater than or equal to in abundance to the next most abundant amino acid residue of the acidic recombinant polypeptide.

The present disclosure also provides nucleic acid molecules encoding any of the recombinant polypeptides disclosed herein. In one aspect, the nucleic acid molecules encode the recombinant polypeptides of SEQ ID NO: 1-16. In one aspect, the nucleic acid molecule comprises, consists essentially of, or consists of a nucleic acid sequence of SEQ ID NO: 17-32 or a nucleic acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the nucleic acid sequence of SEQ ID NO: 17-32.

The present disclosure also provides expression vectors or plasmids comprising any of the nucleic acids disclosed herein. The present disclosure also provides host cells comprising any of the recombinant polypeptides and/or nucleic acids disclosed herein. The present disclosure also provides pharmaceutical compositions comprising any of the recombinant polypeptides and/or nucleic acids disclosed herein, and a pharmaceutically acceptable carrier. In one aspect, the pharmaceutically acceptable carrier comprises a buffer solution comprising a NaCl concentration from about 0.4M to about 1.0M at a pH of about 7.5 to about 9.0.

The present disclosure provides a method of enhancing or inducing an immune response in a subject in need thereof comprising administering to the subject any of the recombinant polypeptides and/or nucleic acids disclosed herein. The present invention provides a method of enhancing or inducing an immune response in a subject in need thereof comprising administering to the subject a pharmaceutical composition comprising any of the recombinant polypeptides and/or nucleic acids disclosed herein In one aspect, the immune response is by immunogenic cell death. In one aspect, the immunogenic cell death comprises endogenous dendritic cell activation. In one aspect, the cells have increased expression of pre-apoptotic Damage-Associated-Molecular-Pattern (DAMP) signals comprising of calreticulin (CRT), Heat Shock Protein 70 (HSP70), Heat Shock Protein 90 (HSP90), or a combination thereof. In one aspect, the cell is a cancer cell. In one aspect, the cancer cell is selected from a group comprising of lung cancer, colon cancer or breast cancer cells.

The present disclosure provides a method of enhancing or inducing the endogenous presentation of disease-associated antigens on a cell surface in a subject in need thereof, comprising administering to the subject any of the recombinant polypeptides and/or nucleic acids disclosed herein. The present disclosure provides a method of enhancing or inducing the endogenous presentation of disease-associated antigens on a cell surface in a subject in need thereof, comprising administering to the subject a pharmaceutical composition comprising any of the recombinant polypeptides and/or nucleic acids disclosed herein. In one aspect, the cell is a cancer cell. In one aspect, the cancer cell is selected from a group comprising of lung cancer, colon cancer or breast cancer cells.

The present disclosure provides a method of treating, preventing or alleviating at least one of the symptoms of a cell proliferative disorder in a subject in need thereof comprising administering to said subject a therapeutically effective amount of any of the recombinant polypeptides and/or nucleic acids disclosed herein. The present disclosure provides a method of treating, preventing or alleviating at least one of the symptoms of a cell proliferative disorder in a subject in need thereof comprising administering to said subject a therapeutically effective amount of a pharmaceutical composition comprising any of the recombinant polypeptides and/or nucleic acids disclosed herein. In one aspect, the cell proliferative disorder is a cancer. In one aspect, the cancer is selected from a group comprising of lung cancer, colon cancer or breast cancer.

The present disclosure also provides a kit comprising the compositions disclosed herein for performing any of the methods disclosed herein.

Any of the above aspects can be combined with any other aspect.

Unless otherwise defined, all technical and scientific terms used herein have the same meaning as commonly understood by one of ordinary skill in the art to which this disclosure belongs.

As used herein, the singular forms of a word also include the plural form of the word, unless the context clearly dictates otherwise; as examples, the terms "a," "an," and "the" are understood to be singular or plural and the term "or" is understood to be inclusive. By way of example, "an element" means one or more element.

Throughout the specification the word "comprising," or variations such as "comprises," will be understood to imply the inclusion of a stated element, integer or step, or group of elements, integers or steps, but not the exclusion of any other element, integer or step, or group of elements, integers or steps. Throughout the specification the word "consisting of," or variations such as "consists of," will be understood to imply the inclusion of a stated element, integer or step, or group of elements, integers or steps, and the exclusion of any other element, integer or step, or group of elements, integers or steps. Throughout the specification the word "consisting essentially of," or variations such as "consists essentially of," will be understood to imply the inclusion of a stated element, integer or step, or group of elements, integers or steps, and any other element, integer or step, or group of elements, integers or steps that do not materially affect the basic and novel characteristics of the claimed invention.

About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed disclosure. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

FIG. 3B shows the flow cytometry profiles used for quantification.

FIG. 4A shows a bar graph quantifying the percentage of cells that express CRT following treatment of H460 human lung cancer cell lines (HTB-177, ATCC) with various concentrations of CRYA_1B recombinant polypeptide (SEQ ID NO: 9). The stock CRYA_1B recombinant polypeptide (SEQ ID NO: 9) was diluted to the final concentration of 0.1, 1, 10, 25, 35, 50 µg/ml and the H460 cells were incubated for 30 minutes at 37° C. The CRT-expressing H460 cells were determined by FACSCalibur (BD Biosciences) flow cytometry using CRT mAb (Abcam). FIG. 4B shows the flow cytometry profiles used for quantification.

FIG. 6B shows the flow cytometry profiles used for quantification.

FIG. 7A shows a bar graph quantifying the percentage of cells that express HSP70 (70 kDa heat shock protein) following treatment of H441 human lung cancer cell lines (HTB-174, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 µg/ml and the H441 cells were incubated for 1 hour and 50 minutes at 37° C. The Hsp70-expressing H441 cells were determined by FACSCalibur (BD Biosciences) flow cytometry using Hsp70 mAb (Enzo Life Sciences).

FIG. 11B shows the flow cytometry profiles used for quantification.

FIG. 12B shows the flow cytometry profiles used for quantification.

FIG. 17B shows the flow cytometry profiles used for quantification.

FIG. 18B shows the flow cytometry profiles used for quantification.

DETAILED DESCRIPTION OF THE INVENTION

Figure 1:
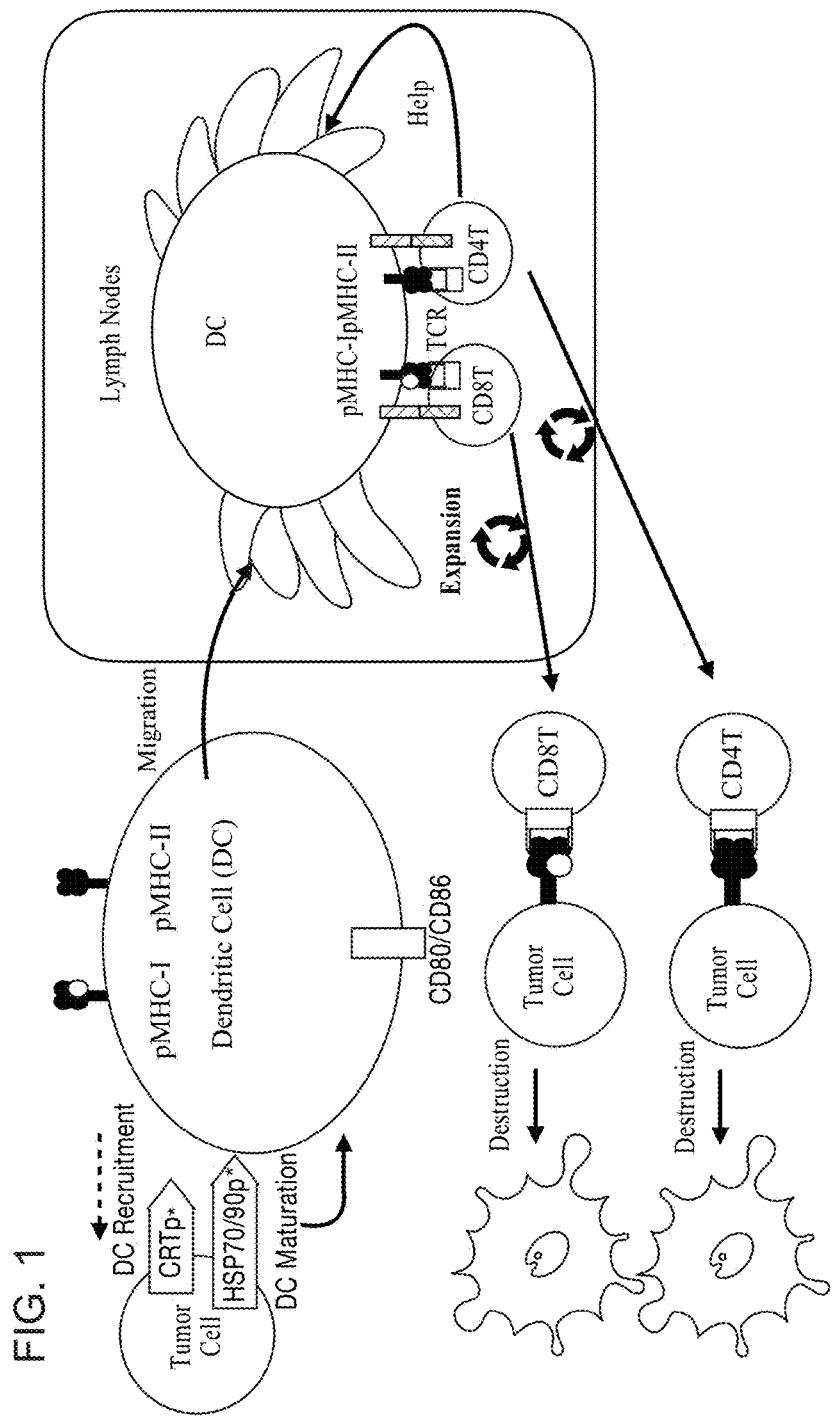
FIG. 1 is a schematic depiction of some characteristics of immunogenic cell death. Tumor cells marked for cell death have cell surface expression of pre-apoptotic Damage-Associated-Molecular-Pattern (DAMP) signals such as calreticulin (CRT), HSP70 and HSP90. Dendritic cells are activated upon the recognition of DAMP signals. Mature dendritic cells migrate to lymph nodes and can in turn prime CD4+ and CD8+ T-cells, which are important for mediating immunogenic cell death.

The present disclosure provides recombinant polypeptides, and the nucleic acids encoding these polypeptides, pharmaceutical compositions comprising these polypeptides and/or nucleic acids, and methods for using these polypeptides and/or nucleic acids to enhance or induce an immune response in a subject in need thereof Compositions of the Present Disclosure The present disclosure provides recombinant polypeptides that comprise, consist essentially of, or consist of, any of the amino acid sequences shown in Table 1A. The present disclosure also provides recombinant polypeptides comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences shown in Table 1A.

The present disclosure also provides acidic recombinant polypeptide variants that comprise, consist essentially of, or consist of, any of the amino acid sequences shown in Table 1A, wherein the recombinant polypeptide variant is acidic as determined by isoelectric point (pI). The present disclosure also provides acidic recombinant polypeptide variants comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences shown in Table 1A.

An "acidic variant" is a variant of a polypeptide of interest which is more acidic (e.g., as determined by calculation of pI) than the parent or original polypeptide of interest. The "pI" or "isoelectric point" of a polypeptide refers to the pH at which the polypeptide's positive charge balances its negative charge. pI can be calculated by any means known in the art, for example, from the net charge of the amino acid residues of the polypeptide or can be determined by isoelectric focusing.

In some aspects, an acidic variant is derived from the original parent sequence by making amino acid substitutions. A first mutational substitution is made by substituting any basic amino acid (K, R or H), neutral non-polar amino acid (G, A, V, L, I, M, F, W or P) or neutral polar amino acid (S, T, C, Y, N or Q) of the original parent sequence with an acidic amino acid (D or E). A second mutational substitution is made by making the inverse mutational substitution of the first mutational substitution. For example, all serine (S) residues from original parent sequence are substituted with glutamic acid (E) residues (first substitution). In addition, all glutamic acid (E) residues from the original parent sequence are substituted with serine (S) residues (second substitution). In one aspect, the inverse substitutions comprise, consist essentially of or consist of the mutation of all serine (S) residues of the original parent sequence to glutamic acid (E) and the mutation of all glutamic acid (E) residues of original parent sequence to serine (S) residues; the mutation of all serine (S) residues of the original parent sequence to aspartic acid (D) and the mutation of all aspartic acid (D) residues of the original parent sequence to serine (S) residues; the mutation of all valine (V) residues of the original parent sequence to aspartic acid (D) and the mutation of all aspartic acid (D) of the original parent sequence to valine (V) residues; or the mutation of all serine (S) residues of the original parent sequence to leucine (L) residues and the mutation of all leucine (L) residues of the original parent sequence to serine (S) residues. In a preferred aspect, the amino acid substitutions result in a recombinant polypeptide where aspartic acid (D), glutamic acid (E) and leucine (L) are each independently present in an amount greater than, or equal to, the amount of any other amino acid residue present within the recombinant polypeptide sequence. In a preferred aspect, the amino acid substitutions result in a recombinant polypeptide with leucine (L), aspartic acid (D) and glutamic acid (E) as the three most abundant amino acid residues of the acidic variant or as greater than or equal to in abundance to the next most abundant amino acid residue of the acidic variant. In some aspects, multiple inverse mutational substitutions of amino acids can be made.

The present disclosure also provides acidic recombinant polypeptide variants that comprise, consist essentially of, or consist of, any of the amino acid sequences shown in Table 1A, wherein the recombinant polypeptide variant is acidic as determined by isoelectric point (pI), wherein the pI of the recombinant peptide variant is lower than the pI of peptide sequence from which the recombinant peptide was derived, and wherein leucine (L), aspartic acid (D) and glutamic acid (E) are each independently present in an amount greater than, or equal to, the amount of any other amino acid residue present within the recombinant polypeptide sequence. The present disclosure also provides acidic recombinant polypeptide variants that comprise, consist essentially of, or consist of, any of the amino acid sequences shown in Table 1A, wherein the recombinant polypeptide variant is acidic as determined by isoelectric point (pI) and wherein leucine (L), aspartic acid (D) and glutamic acid (E) are the three most abundant amino acid residues of the acidic variant or are greater than or equal to in abundance to the next most abundant amino acid residue of the acidic variant. The present disclosure also provides acidic recombinant polypeptide variants comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences shown in Table 1A.

TABLE 1A

Recombinant Polypeptide Sequences

| Name | Amino Acid Sequence | SEQ ID NO: |
|---|---|---|
| Anser cygnoides domesticus CRYAA | MDITIQHPTA7FKRALGPLIPS RLFDQFFGEGLLEYDLLPLF SSTISPYYRQSLFRSVLESG ISEVRSDRDKFTIMLDVKHF SPEDLSVKIIDDFVEIHGKH SERQDDHGYISREFHRRYRL PANVDQSAITCSLSGDGMLT FSGPKVPSNMDPTHSERPIP VSREEKPTSAPSS | 1 |
| Rhea americana CRYAA | MDITIQHPWFKRALGPLIPS RLFDQFFGEGLLEYDLLPLF SSTISPYYRQSLFRSVLESG ISEVRSDREKFTIMLDVKHF SPEDLSVKIIDDFVEIHGKH SERQDDHGYISREFHRRYRL PSNVDQSAITCSLSSDGMLT FSGPKVQANMDPSHSERPIP VSREEKPTSAPSS | 2 |
| Anas platyrhynchos CRYAA | RALGPLIPSRLFDQFFGEGL LEYDLLPLFSSTISPYYRQS LFRSVLESGISEVRSDRDKF TIMLDVKHFSPEDLSVKIID DFVEIHGKHSERQDDHGYIS REFHRRYRLPANVDQSAITC SLSGDGMLTFSGPKVPSNMD PTHSERPIP | 3 |
| Anas platyrhynchos CRYAB | MDITIHNPLIRRPLFSWLAP SRIFDQIFGEHLQESELLPA SPSLSPFLMRSPIFRMPSWL ETGLSEMRLEKDKFSVNLDV KHFSPEELKVKVLGDMVEIH GKHEERQDEHGFIAREFNRK YRIPADVDPLTITSSLSLDG VLTVSAPRKQSDVPERSIPI TREEKPAIAGAQRK | 4 |
| Homo sapiens CRYAA | MDVTIQHPTWFKRTLGPFYPS RLFDQFFGEGLFEYDLLPFL SSTISPYYRQSLFRTVLDSG ISEVRSDRDKFVIFLDVKHF SPEDLTVKVQDDFVEIHGKH NERQDDHGYISREFHRRYRL PSNVDQSALSCSLSADGMLT FCGPKIQTGLDATHAERAIP VSREEKPTSAPSS | 5 |
| Drosophila melanogaster HSP23 | MANIPLLLSLADDLGRMSMV PFYEPYYCQRQRNPYLALVG PMEQQLRQLEKQVGASSGSS GAVSKIGKDGFQVCMDVSHF KPSELVVKVQDNSVLVEGNH EEREDDHGFITRHFVRRYAL PPGYEADKVASTLSSDGVLT IKVPKPPAIEDKGNERIVQI QQVGPAHLNVKENPKEAVEQ DNGNDK | 6 |
| Drosophila melanogaster H5P22 | MRSLPMFWRMAEEMARMPRL SSPFHAFFHEPPVWSVALPR NWQHIARWQEQELAPPATVN KDGYKLTLDVKDYSELKVKV LDESVVLVEAKSEQQEAEQG GYSSRHFLGRYVLPDGYEAD KVSSSLSDDGVLTISVPNPP GVQETLKEREVTIEQTGEPA KKSAEEPKDKTASQ | 7 |

TABLE 1A-continued

Recombinant Polypeptide Sequences

| Name | Amino Acid Sequence | SEQ ID NO: |
|---|---|---|
| Anser cygnoides domesticus CRYAB | MDITIHNPLIRRPLFSWLAP SRIFDQIFGEHLQESELLPA SPSLSPFLMRSPIFRMPSWL ETGLSEMRLEKDKFSVNLDV KHFSPEELKVKVLGDMVEIH GKHEERQDEHGFIAREFNRK YRIPADVDPLTITSSLSLDG VLTVSAPRKQSDVPERSIPI TREEKPAIAGAQRK | 8 |

In a preferred aspect, the present disclosure provides recombinant polypeptides that comprise, consist essentially of, or consist of, any of the amino acid sequences shown in Table 1B. The present disclosure also provides recombinant polypeptides that have an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences shown in Table 1B.

TABLE 1B

Recombinant Polypeptide Sequences

| Name | Amino Acid Sequence | SEQ ID NO: |
|---|---|---|
| CRYA_1B Anser cygnoides domesticus CRYAA | MDITIQHPWFKRALGPLIPE RLFDQFFGSGLLSYDLLPLF EETIEPYYRQELFREVLSEG IESVREDRDKFTIMLDVKHF EPSDLEVKIIDDFVSIHGKH ESRQDDHGYIERSFHRRYRL PANVDQEAITCELEGDGMLT FEGPKVPENMDPTHESRPIP VERSSKPTEAPEE | 9 |
| Rhea americana CRYAA | MDITIQHPWFKRALGPLIPE RLFDQFFGSGLLSYDLLPLF EETIEPYYRQELFREVLSEG IESVREDRSKFTIMLDVKHF EPSDLEVKIIDDFVSIHGKH ESRQDDHGYIERSFHRRYRL PENVDQEAITCELEEDGMLT FEGPKVQANMDPEHESRPIP VERSSKPTEAPEE | 10 |
| Anas platyrhynchos CRYAA | RALGPLIPERLFDQFFGSGL LSYDLLPLFEETIEPYYRQE LFREVLSEGIESVREDRDKF TIMLDVKHFEPSDLEVKIID DFVSIHGKHESRQDDHGYIE RSFHRRYRLPANVDQEAITC ELEGDGMLTFEGPKVPENMD PTHESRPIP | 11 |
| Anas platyrhynchos CRYAB | MSITIHNPLIRRPLFDWLAP DRIFSQIFGEHLQEDELLPA DPDLDPFLMRDPIFRMPDWL ETGLDEMRLEKSKFDVNLSV KHFDPEELKVKVLGSMVEIH GKHEERQSEHGFIAREFNRK YRIPASVSPLTITDDLDLSG VLTVDAPRKQDSVPERDIPI TREEKPAIAGAQRK | 12 |
| Homo sapiens CRYAA | MDVTIQHPWFKRTLGPFYPE RLFDQFFGSGLFSYDLLPFL EETIEPYYRQELFRTVLDEG IESVREDRDKFVIFLDVKHF EPSDLTVKVQDDFVSIHGKH NSRQDDHGYIERSFHRRYRL PENVDQEALECELEADGMLT FCGPKIQTGLDATHASRAIP VERSSKPTEAPEE | 13 |

TABLE 1B-continued

Recombinant Polypeptide Sequences

| Name | Amino Acid Sequence | SEQ ID NO: |
|---|---|---|
| Drosophila melanogaster HSP23 | MANIPLLLSLAVVLGRMSMD PFYEPYYCQRQRNPYLALDG PMEQQLRQLEKQDGASSGSS GADSKIGKVGFQDCMVDSHF KPSELDDKDQVNSDLDEGNH EEREVVHGFITRHFDRRYAL PPGYEAVKDASTLSSVGDLT IKDPKPPAIEVKGNERIDQI QQDGPAHLNDKENPKEADEQ VNGNVK | 14 |
| Drosophila melanogaster HSP22 | MRLSPMFWRMAEEMARMPRS LLPFHAFFHEPPDWLDASPR NWQHIARWQEQESAPPATDN KVGYKSTSVDKVYLESKDKD SVELDDSDEAKLEQQEAEQG GYLLRHFSGRYDSPVGYEAV KDLLLSLVVGDSTILDPNPP GDQETSKEREDTIEQTGEPA KKLAEEPKVKTALQ | 15 |
| Anser cygnoides domesticus CRYAB | MSITIHNPLIRRPLFDWLAP DRIFSQIFGEHLQEDELLPA DPDLDPFLMRDPIFRMPDWL ETGLDEMRLEKSKFDVNLSV KHFDPEELKVKVLGSMVEIH GKHEERQSEHGFIAREFNRK YRIPASVSPLTITDDLDLSG VLTVDAPRKQDSVPERDIPI TREEKPAIAGAQRK | 16 |

The present disclosure provides an alpha crystallin recombinant polypeptide sequence or amino acid sequence derived from *Anser cygnoides domesticus* alpha-A-crystallin (CRYAA) (GenBank # XP_013036875.1) comprising, consisting essentially of, or consisting of, the amino acid sequence of SEQ ID NO: 1 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 1.

The present disclosure provides an acidic alpha crystallin recombinant polypeptide variant sequence or amino acid sequence derived from *Anser cygnoides domesticus* alpha-A-crystallin (CRYAA) (GenBank # XP_013036875.1) comprising, consisting essentially of, or consisting of, the amino acid sequence of SEQ ID NO: 1, wherein the alpha crystallin recombinant polypeptide variant is acidic as determined by isoelectric point (pI), or an acidic alpha crystallin recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 1, wherein the alpha crystallin recombinant polypeptide variant is acidic as determined by isoelectric point (pI). In some aspects, the pI of the recombinant polypeptide is lower than the pI of SEQ ID NO: 1. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic alpha crystallin recombinant polypeptide variant or are greater than or equal to in abundance to the next most abundant amino acid residue of the acidic alpha crystallin recombinant polypeptide variant.

In a preferred aspect, the recombinant polypeptide is an acidic variant derived from *Anser cygnoides domesticus* alpha-A-crystallin (CRYAA) (GenBank # XP_013036875.1) comprising, consisting essentially of, or consisting of, the amino acid sequence of SEQ ID NO: 9 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 9. For example, SEQ ID NO:9 has at least 80% sequence identity to the polypeptide of SEQ ID NO:1, SEQ ID NO:9 is acidic as determined by pI, the pI of SEQ ID NO:9 is lower than the pI of SEQ ID NO:1, and aspartic acid (D), glutamic acid (E) and leucine (L) are each independently present in an amount greater than, or equal to, the amount of any other amino acid residue present within SED ID NO:9 (that is, glutamic acid (E) is 23 residues, leucine (L) is 15 residues, and aspartic acid (D) is 14 residues of the 173 amino acid sequence of SEQ ID NO:9, with proline (P) (14 residues) being the next most present amino acid residue within SEQ ID NO:9).

The present disclosure provides an alpha crystallin recombinant polypeptide sequence or amino acid sequence derived from *Rhea Americana* alpha-A-crystallin (CRYAA) (GenBank # P02505.1) comprising, consisting essentially of, or consisting of, the amino acid sequence of SEQ ID NO: 2 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 2.

The present disclosure provides an acidic alpha crystallin recombinant polypeptide variant sequence or amino acid sequence derived from *Rhea Americana* alpha-A-crystallin (CRYAA) (GenBank # P02505.1) comprising, consisting essentially of, or consisting of, the amino acid sequence of SEQ ID NO: 2, wherein the alpha crystallin recombinant polypeptide variant is acidic as determined by isoelectric point (pI), or an acidic alpha crystallin recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 2, wherein the alpha crystallin recombinant polypeptide variant is acidic as determined by isoelectric point (pI). In some aspects, the pI of the recombinant polypeptide is lower than the pI of SEQ ID NO: 2. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic alpha crystallin recombinant polypeptide variant or are greater than or equal to in abundance to the next most abundant amino acid residue of the acidic alpha crystallin recombinant polypeptide variant.

In a preferred aspect, the recombinant polypeptide is an acidic variant derived from *Rhea Americana* alpha-A-crystallin (CRYAA) (GenBank # P02505.1) comprising, consisting essentially of, or consisting of, the amino acid sequence of SEQ ID NO: 10 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 10. For example, SEQ ID NO:10 has at least 75% sequence identity to the polypeptide of SEQ ID NO:2, SEQ ID NO:10 is acidic as determined by pI, the pI of SEQ ID NO:10 is lower than the pI of SEQ ID NO:2, and aspartic acid (D), glutamic acid (E) and leucine (L) are each independently present in an amount greater than, or equal to, the amount of any other amino acid residue present within SED ID NO:10.

The present disclosure provides an alpha crystallin recombinant polypeptide sequence or amino acid sequence derived from *Anas platyrhynchos* alpha-A-crystallin (CRYAA) (GenBank #O12984.1) comprising, consisting essentially of, consisting of, the amino acid sequence of SEQ ID NO: 3 or a recombinant polypeptide comprising, consisting essentially of, consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 3.

The present disclosure provides an acidic alpha crystallin recombinant polypeptide variant sequence or amino acid sequence derived from *Anas platyrhynchos* alpha-A-crystallin (CRYAA) (GenBank #O12984.1) comprising, consisting essentially of, or consisting of, the amino acid sequence of SEQ ID NO: 3, wherein the alpha crystallin recombinant polypeptide variant is acidic as determined by isoelectric point (pI), or an acidic alpha crystallin recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 3, wherein the alpha crystallin recombinant polypeptide variant is acidic as determined by isoelectric point (pI). In some aspects, the pI of the recombinant polypeptide is lower than the pI of SEQ ID NO: 3. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic alpha crystallin recombinant polypeptide variant or are greater than or equal to in abundance to the next most abundant amino acid residue of the acidic alpha crystallin recombinant polypeptide variant.

In a preferred aspect, the recombinant polypeptide is an acidic variant derived from *Anas platyrhynchos* alpha-A-crystallin (CRYAA) (GenBank #O12984.1) comprising, consisting essentially of, or consisting of, the amino acid sequence of SEQ ID NO: 11 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 11. For example, SEQ ID NO:11 has at least 80% sequence identity to the polypeptide of SEQ ID NO:3, SEQ ID NO:11 is acidic as determined by pI, the pI of SEQ ID NO:11 is lower than the pI of SEQ ID NO:3, and aspartic acid (D), glutamic acid (E) and leucine (L) are each independently present in an amount greater than, or equal to, the amount of any other amino acid residue present within SED ID NO:11.

The present disclosure provides an alpha crystallin recombinant polypeptide sequence or amino acid sequence derived from *Anas platyrhynchos* alpha-B-crystallin (CRYAB) (GenBank # Q05557.1) comprising, consisting essentially of, consisting of, the amino acid sequence of SEQ ID NO: 4 or a recombinant polypeptide comprising, consisting essentially of, consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 4.

The present disclosure provides an acidic alpha crystallin recombinant polypeptide variant sequence or amino acid sequence derived from *Anas platyrhynchos* alpha-B-crystallin (CRYAB) (GenBank # Q05557.1) comprising, consisting essentially of, or consisting of, the amino acid sequence of SEQ ID NO: 4, wherein the alpha crystallin recombinant polypeptide variant is acidic as determined by isoelectric point (pI), or an acidic alpha crystallin recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 4, wherein the alpha crystallin recombinant polypeptide variant is acidic as determined by isoelectric point (pI). In some aspects, the pI of the recombinant polypeptide is lower than the pI of SEQ ID NO: 4. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic alpha crystallin recombinant polypeptide variant or are greater than or equal to in abundance to the next most abundant amino acid residue of the acidic alpha crystallin recombinant polypeptide variant.

In a preferred aspect, the recombinant polypeptide is an acidic variant derived from *Anas platyrhynchos* alpha-B-crystallin (CRYAB) (GenBank # Q05557.1) comprising, consisting essentially of, or consisting of, the amino acid sequence of SEQ ID NO: 12 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 12. For example, SEQ ID NO:12 has at least 80% sequence identity to the polypeptide of SEQ ID NO:4, SEQ ID NO:12 is acidic as determined by pI, the pI of SEQ ID NO:12 is lower than the pI of SEQ ID NO:4, and aspartic acid (D), glutamic acid (E) and leucine (L) are each independently present in an amount greater than, or equal to, the amount of any other amino acid residue present within SED ID NO:12.

The present disclosure provides an alpha crystallin recombinant polypeptide sequence or amino acid sequence derived from *Homo sapiens* alpha-A-crystallin (CRYAA) (GenBank # AAH69528.1) comprising, consisting essentially of, or consisting of, the amino acid sequence of SEQ ID NO: 5 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 5.

The present disclosure provides an acidic alpha crystallin recombinant polypeptide variant sequence or amino acid sequence derived from *Homo sapiens* alpha-A-crystallin (CRYAA) (GenBank # AAH69528.1) comprising, consisting essentially of, or consisting of, the amino acid sequence of SEQ ID NO: 5, wherein the alpha crystallin recombinant polypeptide variant is acidic as determined by isoelectric point (pI), or an acidic alpha crystallin recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 5, wherein the alpha crystallin recombinant polypeptide variant is acidic as determined by isoelectric point (pI). In some aspects, the pI of the recombinant polypeptide is lower than the pI of SEQ ID NO: 5. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic alpha crystallin recombinant polypeptide variant or are greater than or equal to in abundance to the next most abundant amino acid residue of the acidic alpha crystallin recombinant polypeptide variant.

In a preferred aspect, the recombinant polypeptide is an acidic variant derived from *Homo sapiens* alpha-A-crystallin (CRYAA) (GenBank # AAH69528.1) comprising, consisting essentially of, or consisting of, the amino acid sequence of SEQ ID NO: 13 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 13. For example, SEQ ID NO:13 has at least 80% sequence identity to the polypeptide of SEQ ID NO:5, SEQ ID NO:13 is acidic as determined by pI, the pI of SEQ ID NO:13 is lower than the pI of SEQ ID NO:5, and aspartic acid (D), glutamic acid (E) and leucine (L) are each independently present in an amount greater than, or equal to, the amount of any other amino acid residue present within SED ID NO:13.

The present disclosure provides an HSP23 recombinant polypeptide sequence or amino acid sequence derived from *Drosophila melanogaster* HSP23 (GenBank # AAA28637.1) comprising, consisting essentially of, or consisting of, the amino acid sequence of SEQ ID NO: 6 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 6.

The present disclosure provides an HSP23 recombinant polypeptide variant sequence or amino acid sequence derived from *Drosophila melanogaster* HSP23 (GenBank # AAA28637.1) comprising, consisting essentially of, or consisting of, the amino acid sequence of SEQ ID NO: 6, wherein the HSP23 recombinant polypeptide variant is acidic as determined by isoelectric point (pI), or an acidic HSP23 recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 6, wherein the HSP23 recombinant polypeptide variant is acidic as determined by isoelectric point (pI). In some aspects, the pI of the recombinant polypeptide is lower than the pI of SEQ ID NO: 6. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic HSP23 recombinant polypeptide variant or are greater than or equal to in abundance to the next most abundant amino acid residue of the acidic HSP23 recombinant polypeptide variant.

In a preferred aspect, the recombinant polypeptide is an acidic variant derived from *Drosophila melanogaster* HSP23 (GenBank # AAA28637.1) comprising, consisting essentially of, or consisting of, the amino acid sequence of SEQ ID NO: 14 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 14. For example, SEQ ID NO:14 has at least 80% sequence identity to the polypeptide of SEQ ID NO:6, SEQ ID NO:14 is acidic as determined by pI, the pI of SEQ ID NO:14 is lower than the pI of SEQ ID NO:6, and aspartic acid (D), glutamic acid (E) and leucine (L) are each independently present in an amount greater than, or equal to, the amount of any other amino acid residue present within SED ID NO:14.

The present disclosure provides an HSP22 recombinant polypeptide sequence or amino acid sequence derived from *Drosophila melanogaster* HSP22 (GenBank # AAA28635.1) comprising, consisting essentially of, or consisting of, the amino acid sequence of SEQ ID NO: 7 or a recombinant polypeptide having an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 7.

The present disclosure provides an acidic HSP22 recombinant polypeptide variant sequence or amino acid sequence derived from *Drosophila melanogaster* HSP22 (GenBank # AAA28635.1) comprising, consisting essentially of, or consisting of, the amino acid sequence of SEQ ID NO: 7, wherein the HSP22 recombinant polypeptide variant is acidic as determined by isoelectric point (pI), or an acidic HSP22 recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 7, wherein the HSP22 recombinant polypeptide variant is acidic as determined by isoelectric point (pI). In some aspects, the pI of the recombinant polypeptide is lower than the pI of SEQ ID NO: 7. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic HSP22 recombinant polypeptide variant or are greater than or equal to in abundance to the next most abundant amino acid residue of the acidic HSP22 recombinant polypeptide variant.

In a preferred aspect, the recombinant polypeptide is an acidic variant derived from *Drosophila melanogaster* HSP22 (GenBank # AAA28635.1) comprising, consisting essentially of, or consisting of, the amino acid sequence of SEQ ID NO: 15 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 15. For example, SEQ ID NO:15 has at least 65% sequence identity to the polypeptide of SEQ ID NO:7, SEQ ID NO:15 is acidic as determined by pI, the pI of SEQ ID NO:15 is lower than the pI of SEQ ID NO:7, and aspartic acid (D), glutamic acid (E) and leucine (L) are each independently present in an amount greater than, or equal to, the amount of any other amino acid residue present within SED ID NO:15.

The present disclosure provides an alpha crystallin recombinant polypeptide sequence or amino acid sequence derived from *Anser cygnoides domesticus* alpha-B-crystallin (CRYAB) (GenBank # XP_013042703.1) comprising, consisting essentially of, or consisting of, the amino acid sequence of SEQ ID NO: 8 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 8.

The present disclosure provides an acidic alpha crystallin recombinant polypeptide variant sequence or amino acid sequence derived from *Anser cygnoides domesticus* alpha-B-crystallin (CRYAB) (GenBank # XP_013042703.1) comprising, consisting essentially of, or consisting of, the amino acid sequence of SEQ ID NO: 8, wherein the alpha crystallin recombinant polypeptide variant is acidic as determined by isoelectric point (pI), or an acidic alpha crystallin recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 8, wherein the alpha crystallin recombinant polypeptide variant is acidic as determined by isoelectric point (pI). In some aspects, the pI of the recombinant polypeptide is lower than the pI of SEQ ID NO: 8. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic alpha crystallin recombinant polypeptide variant or are greater than or equal to in abundance to the next most abundant amino acid residue of the acidic alpha crystallin recombinant polypeptide variant.

In a preferred aspect, the recombinant polypeptide is an acidic variant derived from *Anser cygnoides domesticus* alpha-B-crystallin (CRYAB) (GenBank # XP_013042703.1) comprising, consisting essentially of, or consisting of, the amino acid sequence of SEQ ID NO: 16 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 16. For example, SEQ ID NO:16 has at least 80% sequence identity to the polypeptide of SEQ ID NO:8, SEQ ID NO:16 is acidic as determined by pI, the pI of SEQ ID NO:16 is lower than the pI of SEQ ID NO:8, and aspartic acid (D), glutamic acid (E) and leucine (L) are each independently present in an amount greater than, or equal to, the amount of any other amino acid residue present within SED ID NO:16.

The present disclosure provides an isolated nucleic acid molecule encoding a recombinant polypeptide that comprises, consists essentially of, or consists of, any of the amino acid sequences shown in Table 1A. The present disclosure also provides isolated nucleic acid molecules encoding recombinant polypeptides comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences shown in Table 1A.

The present disclosure also provides an isolated nucleic acid molecule encoding a recombinant polypeptide variant that comprises, consists essentially of, or consists of, any of the amino acid sequences shown in Table 1A, wherein the recombinant polypeptide variant is acidic as determined by isoelectric point (pI). The present disclosure also provides isolated nucleic acid molecules encoding a recombinant polypeptide variants comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences shown in Table 1A.

The present disclosure also provides isolated nucleic acid molecules encoding acidic recombinant polypeptide variants that comprise, consist essentially of, or consist of, any of the amino acid sequences shown in Table 1A, wherein the recombinant polypeptide variant is acidic as determined by isoelectric point (pI), wherein the pI of the recombinant peptide variant is lower than the pI of peptide sequence from which the recombinant peptide was derived, and wherein leucine (L), aspartic acid (D) and glutamic acid (E) are each independently present in an amount greater than, or equal to, the amount of any other amino acid residue present within the recombinant polypeptide sequence. The present disclosure also provides isolated nucleic acid molecules encoding acidic recombinant polypeptide variants that comprise, consist essentially of, or consist of, any of the amino acid sequences shown in Table 1A, wherein the recombinant polypeptide variant is acidic as determined by isoelectric point (pI) and wherein leucine (L), aspartic acid (D) and glutamic acid (E) are the three most abundant amino acid sequences of the acidic variant or are greater than or equal to in abundance to the next most abundant amino acid residue of the acidic alpha crystallin recombinant polypeptide variant. The present disclosure also provides isolated nucleic acid molecules encoding acid recombinant polypeptide variants comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences shown in Table 1A.

The present disclosure also provides isolated nucleic acid molecules that comprise, consist essentially of, or consist of, any of the nucleic acid sequences shown in Table 2A. The present disclosure also provides nucleic acid molecules comprising, consisting essentially of, or consisting of, a nucleic acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the nucleic acid sequences shown in Table 2A.

TABLE 2A

Nucleic Acid Sequences

| Name | Nucleic Acid Sequence | SEQ ID NO: |
|---|---|---|
| Anser cygnoides domesticus CRYAA | ATGGATATTACCATTCAGCA TCCGTGGTTTAAACGCGCG TGGGCCCGCTGATTCCGAGC CGCCTGTTTGATCAGTTTTT TGGCGAAGGCCTGCTGGAAT ATGATCTGCTGCCGCTGTTT AGCAGCACCATTAGCCCGTA TTATCGCCAGAGCCTGTTTC GCAGCGTGCTGGAAAGCGGC ATTAGCGAAGTGCGCAGCGA TCGCGATAAATTTACCATTA TGCTGGATGTGAAACATTTT AGCCCGGAAGATCTGAGCGT GAAAATTATTGATGATTTTG TGGAAATTCATGGCAAACAT AGCGAACGCCAGGATGATCA TGGCTATATTAGCCGCGAAT TTCATCGCCGCTATCGCCTG CCGGCGAACGTGGATCAGAG CGCGATTACCTGCAGCCTGA GCGGCGATGGCATGCTGACC TTTAGCGGCCCGAAAGTGCC GAGCAACATGGATCCGACCC ATAGCGAACGCCCGATTCCG GTGAGCCGCGAAGAAAAACC GACCAGCGCGCCGAGCAGC | 17 |
| Rhea americana CRYAA | ATGGATATTACCATTCAGCA TCCGTGGTTTAAACGCGCGC TGGGCCCGCTGATTCCGAGC | 18 |

TABLE 2A-continued

Nucleic Acid Sequences

| Name | Nucleic Acid Sequence | SEQ ID NO: |
|---|---|---|
| | CGCCTGTTTGATCAGTTTTT<br>TGGCGAAGGCCTGCTGGAAT<br>ATGATCTGCTGCCGCTGTTT<br>AGCAGCACCATTAGCCCGTA<br>TTATCGCCAGAGCCTGTTTC<br>GCAGCGTGCTGGAAAGCGGC<br>ATTAGCGAAGTGCGCAGCGA<br>TCGCGAAAAATTTACCATTA<br>TGCTGGATGTGAAACATTTT<br>AGCCCGGAAGATCTGAGCGT<br>GAAAATTATTGATGATTTTG<br>TGGAAATTCATGGCAAACAT<br>AGCGAACGCCAGGATGATCA<br>TGGCTATATTAGCCGCGAAT<br>TTCATCGCCGCTATCGCCTG<br>CCGAGCAACGTGGATCAGAG<br>CGCGATTACCTGCAGCCTGA<br>GCAGCGATGGCATGCTGACC<br>TTTAGCGGCCCGAAAGTGCA<br>GGCGAACATGGATCCGAGCC<br>ATAGCGAACGCCCGATTCCG<br>GTGAGCCGCAAGAAAAACC<br>GACCAGCGCGCCGAGCAGC | |
| Anas platyrhynchos<br>CRYAA | CGCGCGCTGGGCCCGCTGAT<br>TCCGAGCCGCCTGTTTGATC<br>AGTTTTTTGGCGAAGGCCTG<br>CTGGAATATGATCTGCTGCC<br>GCTGTTTAGCAGCACCATTA<br>GCCCGTATTATCGCCAGAGC<br>CTGTTTCGCAGCGTGCTGGA<br>AAGCGGCATTAGCGAAGTGC<br>GCAGCGATCGCGATAAATTT<br>ACCATTATGCTGGATGTGAA<br>ACATTTTAGCCCGGAAGATC<br>TGAGCGTGAAAATTATTGAT<br>GATTTTGTGGAAATTCATGG<br>CAAACATAGCGAACGCCAGG<br>ATGATCATGGCTATATTAGC<br>CGCGAATTTCATCGCCGCTA<br>TCGCCTGCCGGCGAACGTGG<br>ATCAGAGCGCGATTACCTGC<br>AGCCTGAGCGGCGATGGCAT<br>GCTGACCTTTAGCGGCCCGA<br>AAGTGCCGAGCAACATGGAT<br>CCGACCCATAGCGAACGCCC<br>GATTCCG | 19 |
| Anas platyrhynchos<br>CRYAB | ATGGATATTACCATTCATAA<br>CCCGCTGATTCGCCGCCCGC<br>TGTTTAGCTGGCTGGCGCCG<br>AGCCGCATTTTTGATCAGAT<br>TTTTGGCGAACATCTGCAGG<br>AAAGCGAACTGCTGCCGGCG<br>AGCCCGAGCCTGAGCCCGTT<br>TCTGATGCGCAGCCCGATTT<br>TTCGCATGCCGAGCTGGCTG<br>GAAACCGGCCTGAGCGAAAT<br>GCGCCTGGAAAAAGATAAAT<br>TTAGCGTGAACCTGGATGTG<br>AAACATTTTAGCCCGGAAGA<br>ACTGAAAGTGAAAGTGCTGG<br>GCGATATGGTGGAAATTCAT<br>GGCAAACATGAAGAACGCCA<br>GGATGAACATGGCTTTATTG<br>CGCGCGAATTTAACCGCAAA<br>TATCGCATTCCGGCGGATGT<br>GGATCCGCTGACCATTACCA<br>GCAGCCTGAGCCTGGATGGC<br>GTGCTGACCGTGAGCGCGCC<br>GCGCAAACAGAGCGATGTGC<br>CGGAACGCAGCATTCCGATT<br>ACCCGCGAAGAAAAACCGGC<br>GATTGCGGGCGCGCAGCGCA<br>AA | 20 |

TABLE 2A-continued

Nucleic Acid Sequences

| Name | Nucleic Acid Sequence | SEQ ID NO: |
|---|---|---|
| Homo sapiens CRYAA | ATGGATGTGACCATTCAGCA TCCGTGGTTTAAACGCACCC TGGGCCCGTTTTATCCGAGC CGCCTGTTTGATCAGTTTTT TGGCGAAGGCCTGTTTGAAT ATGATCTGCTGCCGTTTCTG AGCAGCACCATTAGCCCGTA TTATCGCCAGAGCCTGTTTC GCACCGTGCTGGATAGCGGC ATTAGCGAAGTGCGCAGCGA TCGCGATAAATTTGTGATTT TTCTGGATGTGAAACATTTT AGCCCGGAAGATCTGACCGT GAAAGTGCAGGATGATTTTG TGGAAATTCATGGCAAACAT AACGAACGCCAGGATGATCA TGGCTATATTAGCCGCGAAT TTCATCGCCGCTATCGCCTG CCGAGCAACGTGGATCAGAG CGCGCTGAGCTGCAGCCTGA GCGCGGATGGCATGCTGACC TTTTGCGGCCCGAAAATTCA GACCGGCCTGGATGCGACCC ATGCGGAACGCGCGATTCCG GTGAGCCGCGAAGAAAAACC GACCAGCGCGCCGAGCAGC | 21 |
| Drosophila melanogaster HSP23 | ATGGCGAACATTCCGCTGCT GCTGAGCCTGGCGGATGATC TGGGCCGCATGAGCATGGTG CCGTTTTATGAACCGTATTA TTGCCAGCGCCAGCGCAACC CGTATCTGGCGCTGGTGGGC CCGATGGAACAGCAGCTGCG CCAGCTGGAAAAACAGGTGG GCGCGAGCAGCGGCAGCAGC GGCGCGGTGAGCAAAATTGG CAAAGATGGCTTTCAGGTGT GCATGGATGTGAGCCATTTT AAACCGAGCGAACTGGTGGT GAAAGTGCAGGATAACAGCG TGCTGGTGGAAGGCAACCAT GAAGAACGCGAAGATGATCA TGGCTTTATTACCCGCCATT TTGTGCGCCGCTATGCGCTG CCGCCGGGCTATGAAGCGGA TAAAGTGGCGAGCACCCTGA GCAGCGATGGCGTGCTGACC ATTAAAGTGCCGAAACCGCC GGCGATTGAAGATAAAGGCA ACGAACGCATTGTGCAGATT CAGCAGGTGGGCCCGGCGCA TCTGAACGTGAAAGAAAACC CGAAAGAAGCGGTGGAACAG GATAACGGCAACGATAAA | 22 |
| Drosophila melanogaster HSP22 | ATGCGCAGCCTGCCGATGTT TTGGCGCATGGCGGAAGAAA TGGCGCGCATGCCGCGCCTG AGCAGCCCGTTTCATGCGTT TTTTCATGAACCGCCGGTGT GGAGCGTGGCGCTGCCGCGC AACTGGCAGCATATTGCGCG CTGGCAGGAACAGGAACTGG CGCCGCCGGCGACCGTGAAC AAAGATGGCTATAAACTGAC CCTGGATGTGAAAGATTATA GCGAACTGAAAGTGAAAGTG CTGGATGAAAGCGTGGTGCT GGTGGAAGCGAAAAGCGAAC AGCAGGAAGCGGAACAGGGC GGCTATAGCAGCCGCCATTT TCTGGGCCGCTATGTGCTGC CGGATGGCTATGAAGCGGAT AAAGTGAGCAGCAGCCTGAG CGATGATGGCGTGCTGACCA | 23 |

TABLE 2A-continued

Nucleic Acid Sequences

| Name | Nucleic Acid Sequence | SEQ ID NO: |
|---|---|---|
| | TTAGCGTGCCGAACCCGCCG<br>GGCGTGCAGGAAACCCTGAA<br>AGAACGCGAAGTGACCATTG<br>AACAGACCGGCGAACCGGCG<br>AAAAAAAGCGCGGAAGAACC<br>GAAAGATAAAACCGCGAGCCAG | |
| Anser cygnoides domesticus CRYAB | ATGGATATTACCATTCATAA<br>CCCGCTGATTCGCCGCCCGC<br>TGTTTAGCTGGCTGGCGCCG<br>AGCCGCATTTTTGATCAGAT<br>TTTTGGCGAACATCTGCAGG<br>AAAGCGAACTGCTGCCGGCG<br>AGCCCGAGCCTGAGCCCGTT<br>TCTGATGCGCAGCCCGATTT<br>TTCGCATGCCGAGCTGGCTG<br>GAAACCGGCCTGAGCGAAAT<br>GCGCCTGGAAAAAGATAAAT<br>TTAGCGTGAACCTGGATGTG<br>AAACATTTTAGCCCGGAAGA<br>ACTGAAAGTGAAAGTGCTGG<br>GCGATATGGTGGAAATTCAT<br>GGCAAACATGAAGAACGCCA<br>GGATGAACATGGCTTTATTG<br>CGCGCGAATTTAACCGCAAA<br>TATCGCATTCCGGCGGATGT<br>GGATCCGCTGACCATTACCA<br>GCAGCCTGAGCCTGGATGGC<br>GTGCTGACCGTGAGCGCGCC<br>GCGCAAACAGAGCGATGTGC<br>CGGAACGCAGCATTCCGATT<br>ACCCGCGAAGAAAAACCGGC<br>GATTGCGGGCGCGCAGCGCA<br>AA | 24 |

In a preferred aspect, the present disclosure provides isolated nucleic acid molecules that comprise, consist essentially of, or consist of, any of the nucleic acid sequences shown in Table 2B. The present disclosure also provides nucleic acid molecules comprising, consisting essentially of, or consisting of, a nucleic acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the nucleic acid sequences shown in Table 2B.

TABLE 2B

Nucleic Acid Sequences

| Name | Nucleic Acid Sequence | SEQ ID NO: |
|---|---|---|
| CRYA_1B<br>Anser cygnoides domesticus<br>CRYAA | ATGGATATTACCATTCAGCA<br>TCCGTGGTTTAAACGCGCGC<br>TGGGCCCGCTGATTCCGGAA<br>CGCCTGTTTGATCAGTTTTT<br>TGGCAGCGGCCTGCTGAGCT<br>ATGATCTGCTGCCGCTGTTT<br>GAAGAAACCATTGAACCGTA<br>TTATCGCCAGGAACTGTTTC<br>GCGAAGTGCTGAGCGAAGGC<br>ATTGAAAGCGTGCGCGAAGA<br>TCGCGATAAATTTACCATTA<br>TGCTGGATGTGAAACATTTT<br>GAACCGAGCGATCTGGAAGT<br>GAAAATTATTGATGATTTTG<br>TGAGCATTCATGGCAAACAT<br>GAAAGCCGCCAGGATGATCA<br>TGGCTATATTGAACGCAGCT<br>TCATCGCCGCTATCGCCTG<br>CCGGCGAACGTGGATCAGGA<br>AGCGATTACCTGCGAACTGG<br>AAGGCGATGGCATGCTGACC<br>TTTGAAGGCCCGAAAGTGCC<br>GGAAAACATGGATCCGACCC<br>ATGAAAGCCGCCCGATTCCG | 25 |

TABLE 2B-continued

Nucleic Acid Sequences

| Name | Nucleic Acid Sequence | SEQ ID NO: |
|---|---|---|
| | GTGGAACGCAGCAGCAAACC<br>GACCGAAGCGCCGGAAGAA | |
| Rhea americana<br>CRYAA | ATGGATATTACCATTCAGCA<br>TCCGTGGTTTAAACGCGCGC<br>TGGGCCCGCTGATTCCGGAA<br>CGCCTGTTTGATCAGTTTTT<br>TGGCAGCGGCCTGCTGAGCT<br>ATGATCTGCTGCCGCTGTTT<br>GAAGAAACCATTGAACCGTA<br>TTATCGCCAGGAACTGTTTC<br>GCGAAGTGCTGAGCGAAGGC<br>ATTGAAAGCGTGCGCGAAGA<br>TCGCAGCAAATTTACCATTA<br>TGCTGGATGTGAAACATTTT<br>GAACCGAGCGATCTGGAAGT<br>GAAAATTATTGATGATTTTG<br>TGAGCATTCATGGCAAACAT<br>GAAAGCCGCCAGGATGATCA<br>TGGCTATATTGAACGCAGCT<br>TTCATCGCCGCTATCGCCTG<br>CCGGAAAACGTGGATCAGGA<br>AGCGATTACCTGCGAACTGG<br>AAGAAGATGGCATGCTGACC<br>TTTGAAGGCCCGAAAGTGCA<br>GGCGAACATGGATCCGGAAC<br>ATGAAAGCCGCCCGATTCCG<br>GTGGAACGCAGCAGCAAACC<br>GACCGAAGCGCCGGAAGAA | 26 |
| Anas platyrhynchos<br>CRYAA | CGCGCGCTGGGCCCGCTGAT<br>TCCGGAACGCCTGTTTGATC<br>AGTTTTTTGGCAGCGGCCTG<br>CTGAGCTATGATCTGCTGCC<br>GCTGTTTGAAGAAACCATTG<br>AACCGTATTATCGCCAGGAA<br>CTGTTTCGCGAAGTGCTGAG<br>CGAAGGCATTGAAAGCGTGC<br>GCGAAGATCGCGATAAATTT<br>ACCATTATGCTGGATGTGAA<br>ACATTTTGAACCGAGCGATC<br>TGGAAGTGAAAATTATTGAT<br>GATTTTGTGAGCATTCATGG<br>CAAACATGAAAGCCGCCAGG<br>ATGATCATGGCTATATTGAA<br>CGCAGCTTTCATCGCCGCTA<br>TCGCCTGCCGGCGAACGTGG<br>ATCAGGAAGCGATTACCTGC<br>GAACTGGAAGGCGATGGCAT<br>GCTGACCTTTGAAGGCCCGA<br>AAGTGCCGGAAAACATGGAT<br>CCGACCCATGAAAGCCGCCC<br>GATTCCG | 27 |
| Anas platyrhynchos<br>CRYAB | ATGAGCATTACCATTCATAA<br>CCCGCTGATTCGCCGCCCGC<br>TGTTTGATTGGCTGGCGCCG<br>GATCGCATTTTTAGCCAGAT<br>TTTTGGCGAACATCTGCAGG<br>AAGATGAACTGCTGCCGGCG<br>GATCCGGATCTGGATCCGTT<br>TCTGATGCGCGATCCGATTT<br>TCGCATGCCGGATTGGCTG<br>GAAACCGGCCTGGATGAAAT<br>GCGCCTGGAAAAAAGCAAAT<br>TTGATGTGAACCTGAGCGTG<br>AAACATTTTGATCCGGAAGA<br>ACTGAAAGTGAAAGTGCTGG<br>GCAGCATGGTGGAAATTCAT<br>GGCAAACATGAAGAACGCCA<br>GAGCGAACATGGCTTTATTG<br>CGCGCGAATTTAACCGCAAA<br>TATCGCATTCCGGCGAGCGT<br>GAGCCCGCTGACCATTACCG<br>ATGATCTGGATCTGAGCGGC<br>GTGCTGACCGTGGATGCGCC | 28 |

TABLE 2B-continued

Nucleic Acid Sequences

| Name | Nucleic Acid Sequence | SEQ ID NO: |
|---|---|---|
| | GCGCAAACAGGATAGCGTGC<br>CGGAACGCGATATTCCGATT<br>ACCCGCGAAGAAAAACCGGC<br>GATTGCGGGCGCGCAGCGCA<br>AA | |
| Homo sapiens<br>CRYAA | ATGGATGTGACCATTCAGCA<br>TCCGTGGTTTAAACGCACCC<br>TGGGCCCGTTTTATCCGGAA<br>CGCCTGTTTGATCAGTTTTT<br>TGGCAGCGGCCTGTTTAGCT<br>ATGATCTGCTGCCGTTTCTG<br>GAAGAAACCATTGAACCGTA<br>TTATCGCCAGGAACTGTTTC<br>GCACCGTGCTGGATGAAGGC<br>ATTGAAAGCGTGCGCGAAGA<br>TCGCGATAAATTTGTGATTT<br>TTCTGGATGTGAAACATTTT<br>GAACCGAGCGATCTGACCGT<br>GAAAGTGCAGGATGATTTTG<br>TGAGCATTCATGGCAAACAT<br>AACAGCCGCCAGGATGATCA<br>TGGCTATATTGAACGCAGCT<br>TTCATCGCCGCTATCGCCTG<br>CCGGAAAACGTGGATCAGGA<br>AGCGCTGGAATGCGAACTGG<br>AAGCGGATGGCATGCTGACC<br>TTTTGCGGCCCGAAAATTCA<br>GACCGGCCTGGATGCGACCC<br>ATGCGAGCCGCGCGATTCCG<br>GTGGAACGCAGCAGCAAACC<br>GACCGAAGCGCCGGAAGAA | 29 |
| Drosophila melanogaster<br>HSP23 | ATGGCGAACATTCCGCTGCT<br>GCTGAGCCTGGCGGTGGTGC<br>TGGGCCGCATGAGCATGGAT<br>CCGTTTTATGAACCGTATTA<br>TTGCCAGCGCCAGCGCAACC<br>CGTATCTGGCGCTGGATGGC<br>CCGATGGAACAGCAGCTGCG<br>CCAGCTGGAAAAACAGGATG<br>CGCGAGCAGCGGCAGCAGC<br>GGCGCGGATAGCAAAATTGG<br>CAAAGTGGGCTTTCAGGATT<br>GCATGGTGGATAGCCATTTT<br>AAACCGAGCGAACTGGATGA<br>TAAAGATCAGGTGAACAGCG<br>ATCTGGATGAAGGCAACCAT<br>GAAGAACGCGAAGTGGTGCA<br>TGGCTTTATTACCCGCCATT<br>TTGATCGCCGCTATGCGCTG<br>CCGCCGGGCTATGAAGCGGT<br>GAAAGATGCGAGCACCCTGA<br>GCAGCGTGGGCGATCTGACC<br>ATTAAAGATCCGAAACCGCC<br>GGCGATTGAAGTGAAAGGCA<br>ACGAACGCATTGATCAGATT<br>CAGCAGGATGGCCCGGCGCA<br>TCTGAACGATAAAGAAAACC<br>CGAAAGAAGCGGATGAACAG<br>GTGAACGGCAACGTGAAA | 30 |
| Drosophila melanogaster<br>HSP22 | ATGCGCCTGAGCCCGATGTT<br>TTGGCGCATGGCGGAAGAAA<br>TGGCGCGCATGCCGCGCAGC<br>CTGCTGCCGTTTCATGCGTT<br>TTTTCATGAACCGCCGGATT<br>GGCTGGATGCGAGCCCGCGC<br>AACTGGCAGCATATTGCGCG<br>CTGGCAGGAACAGGAAAGCG<br>CGCCGCCGGCGACCGATAAC<br>AAAGTGGGCTATAAAGCAC<br>CAGCGTGGATAAAGTGTATC<br>TGGAAAGCAAAGATAAAGAT<br>AGCGTGGAACTGGATGATAG<br>CGATGAAGCGAAACTGGAAC | 31 |

TABLE 2B-continued

Nucleic Acid Sequences

| Name | Nucleic Acid Sequence | SEQ ID NO: |
|---|---|---|
| | AGCAGGAAGCGGAACAGGGC<br>GGCTATCTGCTGCGCCATTT<br>TAGCGGCCGCTATGATAGCC<br>CGGTGGGCTATGAAGCGGTG<br>AAAGATCTGCTGCTGAGCCT<br>GGTGGTGGGCGATAGCACCA<br>TTCTGGATCCGAACCCGCCG<br>GGCGATCAGGAAACCAGCAA<br>AGAACGCGAAGATACCATTG<br>AACAGACCGGCGAACCGGCG<br>AAAAAACTGGCGGAAGAACC<br>GAAAGTGAAAACCGCGCTGCAG | |
| Anser cygnoides domesticus CRYAB | ATGAGCATTACCATTCATAA<br>CCCGCTGATTCGCCGCCCGC<br>TGTTTGATTGGCTGGCGCCG<br>GATCGCATTTTTAGCCAGAT<br>TTTTGGCGAACATCTGCAGG<br>AAGATGAACTGCTGCCGGCG<br>GATCCGGATCTGGATCCGTT<br>TCTGATGCGCGATCCGATTT<br>TTCGCATGCCGGATTGGCTG<br>GAAACCGGCCTGGATGAAAT<br>GCGCCTGGAAAAAAGCAAAT<br>TTGATGTGAACCTGAGCGTG<br>AAACATTTTGATCCGGAAGA<br>ACTGAAAGTGAAAGTGCTGG<br>GCAGCATGGTGGAAATTCAT<br>GGCAAACATGAAGAACGCCA<br>GAGCGAACATGGCTTTATTG<br>CGCGCGAATTTAACCGCAAA<br>TATCGCATTCCGGCGAGCGT<br>GAGCCCGCTGACCATTACCG<br>ATGATCTGGATCTGAGCGGC<br>GTGCTGACCGTGGATGCGCC<br>GCGCAAACAGGATAGCGTGC<br>CGGAACGCGATATTCCGATT<br>ACCCGCGAAGAAAAACCGGC<br>GATTGCGGGCGCGCAGCGCAAA | 32 |

The present disclosure also provides pharmaceutical compositions comprising the recombinant polypeptides or nucleic acids disclosed herein.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

In one aspect, the pharmaceutical composition can comprise, consist essentially of, or consist of any one of the recombinant polypeptides disclosed herein in a pharmaceutically acceptable carrier. In some aspects, the pharmaceutical composition is formulated as an aqueous formulation. The aqueous formulation can comprise, consist essentially of, or consist of a salt buffer that may be selected from, but is not limited to, NaCl, KCl, and NaOAc. In a preferred aspect, the salt buffer comprises NaCl. In a more preferred aspect, the NaCl is at a concentration from about 0.4M to about 1.0M. In one aspect, the pH of the buffer solution is between about 7.5 and about 9.0.

A compound or pharmaceutical composition of the invention can be administered to a subject in many of the well-known methods currently used for chemotherapeutic treatment. For example, for the treatment of cancer, a compound of the invention may be injected directly into tumors, injected into the blood stream or body cavities, taken orally or applied through the skin with patches.

The term "therapeutically effective amount," as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In one aspect, the disease or condition to be treated is a cell proliferative disorder. In a preferred aspect, the disease or condition to be treated is cancer.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freezedrying that yields a powder of the active ingredient plus any additional desired ingredient from a previously sterilefiltered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The pharmaceutical compositions can include co-formulations of any of the recombinant polypeptides and nucleic acids described herein.

The pharmaceutical compositions can be included in a container, pack, or dispenser together with instructions for administration.

The present disclosure also provides plasmids, expression vectors and host cells comprising the recombinant polypeptides disclosed herein and the nucleic acid molecules encoding the recombinant polypeptides disclosed herein. In one aspect, the disclosure provides a plasmid or an expression vector comprising a nucleic acid molecule, the molecule comprising a nucleotide sequence of any one of SEQ ID NO: 17-32, or a nucleic acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the nucleic acid sequence of SEQ ID NO: 17-32, or a fragment thereof. In one aspect, the disclosure provides a host cell comprising a recombinant polypeptide comprising an amino acid sequence of any one of SEQ ID NO: 1-16, or an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences of SEQ ID NO: 1-16, or a fragment thereof, or a host cell comprising a nucleic acid molecule comprising a nucleic acid sequence of any one of SEQ ID NO: 17-32, or a nucleic acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the nucleic acid sequence of SEQ ID NO: 17-32, or a fragment thereof.

As used herein, the term "transformation," "transfection," and "transduction" refer to the transfer of nucleic acid (i.e., a nucleotide polymer) into a cell. As used herein, the term "genetic transformation" refers to the transfer and incorporation of DNA, especially recombinant DNA, into a cell. The transferred nucleic acid can be introduced into a cell via an expression vector.

Polynucleotide molecules comprising a desired polynucleotide sequence are propagated by placing the molecule in a vector. Viral and non-viral vectors can be used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. To express a nucleic acid encoding a polypeptide disclosed herein, a nucleic acid molecule encoding the polypeptide, operably linked to regulatory sequences that control transcriptional expression in an expression vector, is introduced into a host cell. In addition to transcriptional regulatory sequences, such as promoters and enhancers, expression vectors can include translational regulatory sequences and a marker gene which is suitable for selection of cells that carry the expression vector. The gene product encoded by a polynucleotide of the disclosure is expressed in any convenient expression system, including, for example, bacterial, yeast, insect, amphibian and mammalian systems. In the expression vector, the polypeptide-encoding polynucleotide is linked to a regulatory sequence as appropriate to obtain the desired expression properties. These can include promoters, enhancers, terminators, operators, repressors, and inducers. The promoters can be regulated (e.g., the promoter from the steroid inducible pIND vector (Invitrogen)) or constitutive (e.g., promoters from CMV, SV40, Elongation Factor, or LTR sequences). These are linked to the desired nucleotide sequence using the techniques described above for linkage to vectors. Any techniques known in the art can be used. Accordingly, the expression vector will generally provide a transcriptional and translational initiation region, which can be inducible or constitutive, where the coding region is operably linked under the transcriptional control of the transcriptional initiation region, and a transcriptional and translational termination region.

An expression cassette ("expression unit") can be introduced into a variety of vectors, e.g., plasmid, BAC, YAC, bacteriophage such as lambda, P1, M13, etc., plant or animal viral vectors (e.g., retroviral-based vectors, adenovirus vectors), and the like, where the vectors are normally characterized by the ability to provide selection of cells comprising the expression vectors. The vectors can provide for extrachromosomal maintenance, particularly as plasmids or viruses, or for integration into the host chromosome. Where extrachromosomal maintenance is desired, an origin sequence is provided for the replication of the plasmid, which can be low or high copy-number. A wide variety of markers are available for selection, particularly those which protect against toxins, more particularly against antibiotics. The particular marker that is chosen is selected in accordance with the nature of the host, where, in some cases, complementation can be employed with auxotrophic hosts. Introduction of the DNA construct can use any convenient method, including, e.g., conjugation, bacterial transformation, calcium-precipitated DNA, electroporation, fusion, transfection, infection with viral vectors, biolistics, and the like.

Accordingly, polypeptides for use within the present disclosure can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook and Russell, *Molecular Cloning: A Laboratory Manual* (3rd ed., Cold Spring Harbor Laboratory Press, Cold Spring Harbor, N.Y., 2001), and Ausubel et al., *Short Protocols in Molecular Biology* (4th ed., John Wiley & Sons, 1999). For example, the recombinant polypeptides of the disclosure can be expressed from bacterial *Escherichia coli* cells.

To direct a recombinant polypeptide into the secretory pathway of a host cell, a secretory signal sequence (also known as a leader sequence) can be provided in the expression vector. The secretory signal sequence can be that of the native form of the recombinant protein, or can be derived from another secreted protein or synthesized de novo. The secretory signal sequence is operably linked to the polypeptide-encoding DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences can be positioned elsewhere in the DNA sequence of interest (see, e.g., Welch et al., U.S. Pat. No. 5,037,743; Holland et al., U.S. Pat. No. 5,143,830).

Cultured mammalian cells can be suitable hosts for production of recombinant polypeptides for use within the present disclosure. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-845, 1982), DEAE-dextran mediated transfection (Ausubel et al., supra), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44; CHO DXB11 (Hyclone, Logan, Utah); see also, e.g., Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658). Additional suitable cell lines are known in the art and available from public depositories such as the American Type Culture Collection, Manassas, Va. Strong transcription promoters can be used, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants." Cells that have been cultured in the presence of the selective agent and are able to pass the gene of interest to their progeny are referred to as "stable transfectants." Exemplary selectable markers include a gene encoding resistance to the antibiotic neomycin, which allows selection to be carried out in the presence of a neomycin-type drug, such as G-418 or the like; the gpt gene for xanthine-guanine phosphoribosyl transferase, which permits host cell growth in the presence of mycophenolic acid/xanthine; and markers that provide resistance to zeocin, bleomycin, blastocidin, and hygromycin (see, e.g., Gatignol et al., *Mol. Gen. Genet.* 207:342, 1987; Drocourt et al., *Nucl. Acids Res.* 18:4009, 1990). Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g., hygromycin resistance, multi-drug resistance, puromycin acetyltransferase) can also be used.

Other higher eukaryotic cells can also be used as hosts, including insect cells, plant cells and avian cells. The use of *Agrobacterium rhizogenes* as a vector for expressing genes in plant cells has been reviewed by Sinkar et al., *J Biosci. (Bangalore)* 11:47-58, 1987. Transformation of insect cells and production of foreign polypeptides therein is disclosed by Guarino et al., U.S. Pat. No. 5,162,222 and WO 94/06463.

Insect cells can be infected with recombinant baculovirus, commonly derived from *Autographa californica* nuclear polyhedrosis virus (AcNPV). See King and Possee, *The Baculovirus Expression System: A Laboratory Guide* (Chapman & Hall, London); O'Reilly et al., *Baculovirus Expression Vectors: A Laboratory Manual* (Oxford University Press., New York 1994); and *Baculovirus Expression Protocols. Methods in Molecular Biology* (Richardson ed., Humana Press, Totowa, N.J., 1995). Recombinant baculovirus can also be produced through the use of a transposon-based system described by Luckow et al. (*J. Virol.* 67:4566-4579, 1993). This system, which utilizes transfer vectors, is commercially available in kit form (BAC-TO-BAC kit; Life Technologies, Gaithersburg, Md.). The transfer vector (e.g., PFASTBAC1; Life Technologies) contains a Tn7 transposon to move the DNA encoding the protein of interest into a baculovirus genome maintained in *E. coli* as a large plasmid called a "bacmid." See Hill-Perkins and Possee, *J. Gen. Virol.* 71:971-976, 1990; Bonning et al., *J. Gen. Virol.* 75:1551-1556, 1994; and Chazenbalk and Rapoport, *J. Biol. Chem.* 270:1543-1549, 1995. In addition, transfer vectors can include an in-frame fusion with DNA encoding a polypeptide extension or affinity tag as disclosed above. Using techniques known in the art, a transfer vector containing a protein-encoding DNA sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses the protein or interest is subsequently produced. Recombinant viral stocks are made by methods commonly used in the art.

For protein production, a recombinant virus can be used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, Calif.). See generally Glick and Pasternak, *Molecular Biotechnology, Principles & Applications of Recombinant DNA* (ASM Press, Washington, D.C., 1994). See also U.S. Pat. No. 5,300,435. Serum-free media are used to grow and maintain the cells. Suitable media formulations are known in the art and can be obtained from commercial suppliers. The cells are grown up from an inoculation density of approximately $2$-$5 \times 10^5$ cells to a density of $1$-$2 \times 10^6$ cells, at which time a recombinant viral stock is added at a multiplicity of infection (MOI) of 0.1 to 10, more typically near 3. Procedures used are generally described in available laboratory manuals (see, e.g., King and Possee, supra; O'Reilly et al., supra; Richardson, supra).

Fungal cells, including yeast cells, can also be used within the present disclosure. Yeast species of in this regard include, e.g., *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936; and 4,661,454. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii*, and *Candida maltosa* are known in the art. See, e.g., Gleeson et al., *J. Gen. Microbiol.* 132:3459-3465, 1986; Cregg, U.S. Pat. No. 4,882,279; and Raymond et al, Yeast 14:11-23, 1998. *Aspergillus* cells can be utilized according to the methods of McKnight et al., U.S. Pat. No. 4,935,349.

Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli, Bacillus*, and other genera are also useful host cells within the present disclosure. Techniques for transforming these hosts and expressing foreign DNA sequences cloned therein are well-known in the art (see, e.g., Sambrook and Russell, supra). When expressing a recombinant protein in bacteria such as *E. coli*, the protein can be retained in the cytoplasm, typically as insoluble granules, or can be directed to the periplasmic space by a bacterial secretion sequence. In the former case, the cells are lysed, and the granules are recovered and denatured using, for example, guanidine isothiocyanate or urea. The denatured protein can then be refolded and dimerized by diluting the denaturant, such as by dialysis against a solution of urea and a combination of reduced and oxidized glutathione, followed by dialysis against a buffered saline solution. In the alternative, the protein can be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted proteins can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media can also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

The recombinant polypeptides can be purified by conventional protein purification methods, typically by a combination of chromatographic techniques. See generally *Affinity Chromatography: Principles & Methods* (Pharmacia LKB Biotechnology, Uppsala, Sweden, 1988); Scopes, *Protein Purification: Principles and Practice* (Springer-Verlag, New York 1994). Additional purification steps, such as gel filtration, can be used to obtain the desired level of purity or to provide for desalting, buffer exchange, and the like.

Methods of the Present Disclosure

The present disclosure provides methods for enhancing or inducing an immune response in a subject in need thereof. The subject in need thereof can be a subject with a cell proliferation disorder. In one aspect, the subject has cancer and the cell is a cancer cell. In a preferred aspect, the subject has lung cancer, colon cancer or breast cancer. In a preferred aspect, the cancer cells can be lung cancer cells, colon cancer cells or breast cancer cells.

In one aspect, the methods for enhancing or inducing an immune response in a subject in need thereof comprise administering at least one recombinant polypeptide of the present disclosure, or a nucleic acid encoding a recombinant polypeptide of the present disclosure. In one aspect, the at least one recombinant polypeptide of the present disclosure comprises a recombinant polypeptide of SEQ ID NO: 1-8 or an amino acid sequence that is at least about 50%, about 55%, about 60%, about 65%, about 70%, about 75%, about 80%, about 85%, about 90%, about 91%, about 92%, about 93%, about 94%, about 95%, about 96%, about 9'7%, about 98% or about 99% identical to any of the amino acid sequences of SEQ ID NO: 1-8 or an acidic variant thereof as described herein. In one aspect, the at least one recombinant polypeptide of the present disclosure comprises a recombinant polypeptide of SEQ ID NO: 9-16 or an amino acid sequence that is at least about 50%, about 55%, about 60%, about 65%, about 70%, about 75%, about 80%, about 85%, about 90%, about 91%, about 92%, about 93%, about 94%, about 95%, about 96%, about 9'7%, about 98% or about 99% identical to any of the amino acid sequences of SEQ ID NO: 9-16. In a preferred aspect, the at least one recombinant polypeptide of the present disclosure comprises a recombinant polypeptide of SEQ ID NO: 9.

The present disclosure also provides methods for enhancing or inducing the endogenous presentation of disease associated antigens on a cell surface in a subject in need thereof. The subject in need thereof can be a subject with a cell proliferation disorder. In one aspect, the subject has cancer and the cell is a cancer cell. In a preferred aspect, the subject has lung cancer, colon cancer or breast cancer. In a preferred aspect, the cancer cells can be lung cancer cells, colon cancer cells or breast cancer cells.

In one aspect, the methods for enhancing or inducing the endogenous presentation of disease associated antigens on a cell surface in a subject in need thereof comprise administering at least one recombinant polypeptide of the present disclosure, or a nucleic acid encoding a recombinant polypeptide of the present disclosure. In one aspect, the at least one recombinant polypeptide of the present disclosure comprises a recombinant polypeptide of SEQ ID NO: 1-8 or an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences of SEQ ID NO: 1-8 or an acidic variant thereof as described herein. In one aspect, the at least one recombinant polypeptide of the present disclosure comprises a recombinant polypeptide of SEQ ID NO: 9-16 or an amino acid sequence that is at least about 50%, about 55%, about 60%, about 65%, about 70%, about 75%, about 80%, about 85%, about 90%, about 91%, about 92%, about 93%, about 94%, about 95%, about 96%, about 9'7%, about 98% or about 99% identical to any of the amino acid sequences of SEQ ID NO: 9-16. In a preferred aspect, the at least one recombinant polypeptide of the present disclosure comprises a recombinant polypeptide of SEQ ID NO: 9.

In one aspect, enhancing or inducing an "immune response" can be, for example, a cytokine release response or a humoral (antigen-specific) immune response. The immune response to be enhanced for example, can be an innate immune response, a local immune response, a mucosal immune response or a systemic immune response. As used herein, the terms "enhance" or "enhancing" refer to strengthening (augmenting) of an existing immune response. The term "inducing" refers to the initiation of an immune response.

In one aspect, "immune response" refers to "immunogenic cell death" or "immunogenic apoptosis", which is characterized by a robust immune response against antigens expressed by dying cells (FIG. 1). Dying cells, such as cancer cells, can have an increased expression of pre-apoptotic Damage-Associated-Molecular-Pattern (DAMP) signals comprising calreticulin (CRT), HSP70, HSP90, or a combination thereof. In a preferred aspect, the cells have increased expression of each of CRT, HSP70 and HSP90. Techniques known to one skilled in the art can be used to assess the expression of these cell surface markers. For example, the expression of the cell surface markers can be assessed using standard techniques such as flow cytometry, immunocytochemistry (e.g., staining with tissue specific or cell-marker specific antibodies), fluorescence activated cell sorting (FACS), magnetic activated cell sorting (MACS) or other similar methods known in the art. Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one aspect, cell surface marker-specific antibodies or ligands are labeled with distinct fluorescent labels. Cells are processed through the flow cytometer, allowing separation of cells based on their ability to bind to the antibodies used. In one aspect, the method of the present disclosure induces the expression of pre-apoptotic HSP70, HSP90 or calreticulin on a cell surface, such as a cancer cell surface.

In one aspect, "immunogenic cell death" or "immunogenic apoptosis" involves the interaction of dendritic cells with a cell, such as a cancer cell, leading to a more rapid rate of endogenous dendritic cell activation, dendritic cell maturation and phagocytosis. The recognition of pre-apoptotic DAMP signals comprising calreticulin (CRT), HSP70, HSP90, or a combination thereof, by the dendritic cells triggers "endogenous dendritic cell activation". This leads to "dendritic cell maturation", which comprises a redistribution of major histocompatibility complex (MHC) molecules from intracellular endocytic compartments to the dendritic cell surface, down-regulation of antigen internalization, an increase of surface expression of co-stimulatory molecules (including CD80 and CD86), cytoskeleton re-organization, secretion of chemokines, cytokines and proteases, surface expression of adhesion molecules and surface expression of chemokine receptors. Mature dendritic cells that have been exposed to cancer cells dying by immunogenic cell death can migrate to lymph nodes and induce high numbers of tumor-specific T lymphocytes (including CD4+ and CD8+ T cells). This triggers a targeted T-cell mediated response towards the cancer cell. The process of "immunogenic cell death" or "immunogenic apoptosis" is shown in FIG. 1. A person skilled in the art will appreciate that not all techniques known to induce cell death will necessarily induce immunogenic cell death. Only agents inducing immunogenic cell death will elicit efficient endogenous dendritic cell activation. In one aspect an "immune response" refers to endogenous dendritic cell activation, dendritic cell maturation or T-cell mediated response or a combination thereof.

In one aspect, "apoptosis" is the term used to describe the cell signaling cascade known as programmed cell death. Various therapeutic indications exist for molecules that induce apoptosis (e.g. cancer). Apoptosis can be monitored by any of a number of available techniques known and available in the art including, for example, assays that measure fragmentation of DNA, alterations in membrane asymmetry, activation of apoptotic caspases and/or release of cytochrome C and AIF. In one aspect, apoptosis is measured by the activation and expression of Caspase 3/7.

The present disclosure also provides methods for treating, preventing or alleviating at least one symptom of a cell proliferative disorder in a subject in need thereof. In one aspect, the method is alleviating at least one symptom of a cell proliferative disorder in a subject in need thereof. In one aspect the cell proliferative disorder is cancer. In a preferred aspect, the cancer is lung cancer, colon cancer or breast cancer.

In one aspect, the methods for treating, preventing or alleviating at least one symptom of a cell proliferative disorder in a subject in need thereof comprise administering at least one recombinant polypeptide of the present disclosure, or a nucleic acid encoding a recombinant polypeptide of the present disclosure. In one aspect, the at least one recombinant polypeptide of the present disclosure comprises a recombinant polypeptide of SEQ ID NO: 1-8 or an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences of SEQ ID NO: 1-8 or an acidic variant thereof as described herein. In one aspect, the at least one recombinant polypeptide of the present disclosure comprises a recombinant polypeptide of SEQ ID NO: 9-16. In a preferred aspect, the at least one recombinant polypeptide of the present disclosure comprises a recombinant polypeptide of SEQ ID NO: 9 or an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences of SEQ ID NO: 9-16.

As used herein, a "subject" can be any mammal, e.g., a human, a primate, mouse, rat, dog, cat, cow, horse, pig, sheep, goat, camel. In a preferred aspect, the subject is a human. In one aspect, a "subject in need thereof" is a subject having a cell proliferative disorder, or a subject having an increased risk of developing a cell proliferative disorder relative to the population at large. In one aspect, a subject in need thereof has a precancerous condition. In a preferred aspect, a subject in need thereof has cancer.

As used herein, "treating" describes the management and care of a patient for the purpose of combating a disease, condition, or disorder and includes decreasing or alleviating the symptoms or complications, or eliminating the disease, condition or disorder. As used herein, "preventing" describes stopping the onset of the symptoms or complications of the disease, condition or disorder. As used herein, "alleviating" describes reducing the symptoms or complications of disease, condition or disorder.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the disclosure encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi's sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "lung cancer" is a cell proliferative disorder involving cells of the lung. In one aspect, lung cancer include all forms of cell proliferative disorders affecting lung cells. In one aspect, lung cancer include lung cancer, a precancer or precancerous condition of the lung, benign growths or lesions of the lung, and malignant growths or lesions of the lung, and metastatic lesions in tissue and organs in the body other than the lung. In a preferred aspect, the method of the present disclosure may be used to treat lung cancer or cell proliferative disorders of the lung. In one aspect, lung cancer includes all forms of cancer of the lung. In another aspect, lung cancer includes malignant lung neoplasms, carcinoma in situ, typical carcinoid tumors, and atypical carcinoid tumors. In another aspect, lung cancer includes small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. In another aspect, lung cancer includes "scar carcinoma," bronchioalveolar carcinoma, giant cell carcinoma, spindle cell carcinoma, and large cell neuroendocrine carcinoma. In one aspect lung cancer includes stage 0, IA, IB, IIA, IIB, IIIA, IIIB and IV lung cancer. In another aspect, lung cancer includes lung neoplasms having histologic and ultrastructual heterogeneity (e.g., mixed cell types).

In one aspect, lung cancer include all forms of cell proliferative disorders affecting lung cells. In one aspect, cell proliferative disorders of the lung include lung cancer, precancerous conditions of the lung. In one aspect, cell proliferative disorders of the lung include hyperplasia, metaplasia, and dysplasia of the lung. In another aspect, lung cancer include asbestos-induced hyperplasia, squamous metaplasia, and benign reactive mesothelial metaplasia. In another aspect, cell proliferative disorders of the lung include replacement of columnar epithelium with stratified squamous epithelium, and mucosal dysplasia. In another aspect, individuals exposed to inhaled injurious environmental agents such as cigarette smoke and asbestos may be at increased risk for developing cell proliferative disorders of the lung. In another aspect, prior lung diseases that may predispose individuals to development of cell proliferative disorders of the lung include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "colon cancer" is a cell proliferative disorder involving cells of the colon. In a preferred aspect, the method of the present disclosure may be used to treat colon cancer or cell proliferative disorders of the colon. In one aspect, colon cancer includes all forms of cancer of the colon. In another aspect, colon cancer includes sporadic and hereditary colon cancers. In another aspect, colon cancer includes malignant colon neoplasms, carcinoma in situ, typical carcinoid tumors, and atypical carcinoid tumors. In another aspect, colon cancer includes adenocarcinoma, squamous cell carcinoma, and adenosquamous cell carcinoma. In another aspect, colon cancer is associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. In another aspect, colon cancer is caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

In one aspect, colon cancer include all forms of cell proliferative disorders affecting colon cells. In one aspect, colon cancer include colon cancer, precancerous conditions of the colon, adenomatous polyps of the colon and metachronous lesions of the colon. In one aspect colon cancer includes stage 0, I, IIA, IIB, IIC, IIIA, IIIB, IIIC, IVA, IVB and IVC colon cancer. In one aspect, a colon cancer includes adenoma. In one aspect, colon cancer is characterized by hyperplasia, metaplasia or dysplasia of the colon. In another aspect, prior colon diseases that may predispose individuals to development of cell proliferative disorders of the colon include prior colon cancer. In another aspect, current disease that may predispose individuals to development of cell proliferative disorders of the colon include Crohn's disease and ulcerative colitis. In one aspect, a cell proliferative disorder of the colon is associated with a mutation in a gene selected from the group consisting of p53, ras, FAP and DCC. In another aspect, an individual has an elevated risk of developing a cell proliferative disorder of the colon due to the presence of a mutation in a gene selected from the group consisting of p53, ras, FAP and DCC.

A "breast cancer" is a cell proliferative disorder involving cells of the breast. In a preferred aspect, breast cancer include all forms of cell proliferative disorders affecting breast cells. In one aspect, breast cancer include breast cancer, a precancer or precancerous condition of the breast, benign growths or lesions of the breast, and malignant growths or lesions of the breast, and metastatic lesions in tissue and organs in the body other than the breast. In another aspect, breast cancer include hyperplasia, metaplasia, and dysplasia of the breast.

In one aspect, breast cancer is a precancerous condition of the breast. In one aspect, the method of the present disclosure may be used to treat a precancerous condition of the breast. In one aspect, a precancerous condition of the breast includes atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). In another aspect, a precancerous condition of the breast has been staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

In one aspect, the method of the present disclosure may be used to treat breast cancer. In one aspect, breast cancer includes all forms of cancer of the breast. In one aspect, breast cancer includes primary epithelial breast cancers. In another aspect, breast cancer includes cancers in which the breast is involved by other tumors such as lymphoma, sarcoma or melanoma. In another aspect, breast cancer includes carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. In one aspect, breast cancer includes Stage I, II, IIIA, IIIB, IIIC and IV breast cancer. In one aspect, ductal carcinoma of the breast includes invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. In one aspect, lobular carcinoma of the breast includes invasive lobular carcinoma with predominant in situ component, invasive lobular carcinoma, and infiltrating lobular carcinoma. In one aspect, breast cancer includes Paget's disease, Paget's disease with intraductal carcinoma, and Paget's disease with invasive ductal carcinoma. In another aspect, breast cancer includes breast neoplasms having histologic and ultrastructual heterogeneity (e.g., mixed cell types).

In one aspect, treating cancer results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. In a preferred aspect, size of a tumor may be measured as a diameter of the tumor.

In another aspect, treating cancer results in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In another aspect, treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, treating cancer results in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is 2×, 3×, 4×, 5×, 10×, or 50×.

In another aspect, treating cancer results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in increase in average survival time of a population of treated subjects in comparison to a population receiving a therapy that is not a recombinant polypeptide of the present disclosure. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in a decrease in the mortality rate of a population of treated subjects in comparison to a population receiving carrier alone. In another aspect, treating cancer results in a decrease in the mortality rate of a population of treated subjects in comparison to an untreated population. In a further aspect, treating cancer results in a decrease in the mortality rate of a population of treated subjects in comparison to a population receiving monotherapy with a drug that is not a recombinant polypeptide of the present disclosure. Preferably, the mortality rate is decreased by more than 2%; more preferably, by more than 5%; more preferably, by more than 10%; and most preferably, by more than 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease-related deaths per unit time following completion of a first round of treatment with an active compound.

In another aspect, treating cancer results in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating cancer results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured, for example, by measuring an increase in the diameter of a tumor after a prior tumor shrinkage that followed treatment. In another preferred aspect, a decrease in tumor regrowth is indicated by failure of tumors to reoccur after treatment has stopped.

In another aspect, treating, preventing, or alleviating a cancer results in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating, preventing, or alleviating a cancer results in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. In a preferred aspect, the proportion of proliferating cells is measured, for example, by quantifying the number of dividing cells relative to the number of nondividing cells in a tissue sample. In another preferred aspect, the proportion of proliferating cells is equivalent to the mitotic index.

In another aspect, treating, preventing, or alleviating a cancer results in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. In a preferred aspect, size of an area or zone of cellular proliferation may be measured as a diameter or width of an area or zone of cellular proliferation.

In another aspect, treating, preventing, or alleviating a cancer results in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. In one aspect, an abnormal cellular morphology is measured by microscopy, e.g., using an inverted tissue culture microscope. In one aspect, an abnormal cellular morphology takes the form of nuclear pleiomorphism.

In one aspect, treating cancer or a cell proliferative disorder results in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. In one aspect, number of cells in a population is measured by fluorescence activated cell sorting (FACS). In another aspect, number of cells in a population is measured by immunofluorescence microscopy. In another aspect, number of cells in a population is measured by light microscopy. In another aspect, methods of measuring cell death are as shown in Li et al., (2003) Proc Natl Acad Sci USA. 100(5): 2674-8. In a preferred aspect, cell death occurs by immunogenic cell death.

Any of the above aspects can be combined with any other aspect as disclosed herein.

Example 1: Methods of Producing Recombinant Polypeptides

Materials and Methods

The methods of producing the recombinant polypeptides of the present disclosure utilized the PCR primers disclosed in Table 3.

TABLE 3

| Primer Sequences | | |
| --- | --- | --- |
| Primer | Nucleotide Sequence (5' to 3') | SEQ ID NO: |
| A1 | GGGGGGCATATGGACATTACCATCCAGCACCCCTGGTTCAAGCGCGCTCT | 33 |
| A2 | GGGGGGAAGCTTTTACTCCTCAGGCGCCTCGGTGGGCTT | 34 |
| ioE1 | CCTCTGTTCGAGGAGACTATCGAGCCCTACTA | 35 |
| ioE2 | TAGTAGGGCTCGATAGTCTCCTCGAACAGAGG | 36 |
| ioE3 | ACCGGCAGGAGCTGTTCCGCGAGGTGCTGTCGGAGGGCATTGAGTCGGTGAGGGAGGACCGGGA | 37 |
| ioE4 | TCCCGGTCCTCCCTCACCGACTCAATGCCCTCCGACAGCACCTCGCGGAACAGCTCCTGCCGGT | 38 |

TABLE 3-continued

Primer Sequences

| Primer | Nucleotide Sequence (5' to 3') | SEQ ID NO: |
|---|---|---|
| ioE5 | ACTATGCTGGACGTAAAACACTTTGAGCCTTCGGACCTGGAGGTGAAGATTA | 39 |
| ioE6 | TAATCTTCACCTCCAGGTCCGAAGGCTCAAAGTGTTTTACGTCCAGCATGAT | 40 |
| ioE7 | AAGATTATCGACGACTTTGTGTCGATCCATGGC | 41 |
| ioE8 | GCCATGGATCGACACAAAGTCGTCGATAATCTT | 42 |
| ioE9 | GGCAAGCACGAGTCGAGACAGGACGACCACGGCTACATCGAGCGGTCGTTTCACCGC | 43 |
| ioE10 | GCGGTGAAACGACCGCTCGATGTAGCCGTGGTCGTCCTGTCTCGACTCGTGCTTGCC | 44 |
| ioE11 | GCGGACCAGGAGGCCATCACCTGCGAGCTGGAGGGCGACGG | 45 |
| ioE12 | CCGTCGCCCTCCAGCTCGCAGGTGATGGCCTCCTGGTCCAC | 46 |
| ioE13 | TTCGACCAGTTTTTCGGATCGGGTCTGCTGTCGTATGACCTGCTGCCTCTGTTC | 47 |
| ioE14 | GGGGACCTTGGGGCCCTCGAAGGTCAGCATGCCGTCGCC | 48 |
| ioE15 | TTCAAGCGCGCTCTGGGACCCCTGATTCCAGAGCGTCTGTTCGACCAGTTTTTCGGA | 49 |
| ioE16 | CACGGGGATGGGCCTCGACTCGTGGGTGGGGTCCATGTTCTCGGGGACCTTGGGG | 50 |
| ioE17 | ATGGACATTACCATCCAG | 51 |
| ioE18 | AAGCTTTTACTCCTCAGGCGCCTCGGTGGGCTTCGACGACCGCTCCACGGGGATGGGCCT | 52 |

Preparation of Template DNA

The full length CRYAA sequence from *Anser cygnoides domesticus* (SEQ ID NO: 17) was amplified in a PCR reaction using Pfu polymerase. A1 primer (SEQ ID NO: 33) and A2 primer (SEQ ID NO: 34) were used in the PCR reaction. The gene was cloned into NdeI and HindIII sites in a pET24a vector (Novagen) using the manufacturer's protocol. The ligation mixture was transformed into *Escherichia coli* DH5alpha cells and transformants were selected on LB ampicillin plates. Plasmid DNA was isolated from several transformants and screened by restriction digestion of NdeI and HindIII sites. A sequence verified clone containing *Anser cygnoides domesticus* CRYAA (SEQ ID NO: 17) was identified and used as template.

Cloning of Plasmid Containing the CRYA_1B Recombinant Polypeptide Sequence

The recombinant plasmid containing CRYA_1B (SEQ ID NO: 25) was prepared in the following manner. PCR was performed using the template DNA described above, forward primer IoE1 (SEQ ID NO: 35) and reverse primer IoE2 (SEQ ID NO: 36). PCR temperature and time were programmed as follows: denaturing at 95° C. for 5 minutes; followed by 30 cycles of PCR reactions with denaturation at 95° C. for 30 sec, annealing at 60° C. for 30 sec, and elongation at 72° C. for 1 minute; final elongation at 72° C. for 10 minutes. All PCR amplifications were performed with Pfu Ultra polymerase (Stratagene). PCR products were separated electrophoretically using 1.0% agarose gel, and stained with ethidium bromide. The DNA fragment was extracted from the gel using GFX™ PCR DNA and Gel Bind Purification Kit (GE Healthcare) and ligated into a pET24a (Novagen) vector. The ligation mixture was transformed into the DH5alpha *Escherichia coli* strain and transformants were selected on LB plates containing ampicillin. Plasmid DNA was isolated from transformants. A sequence verified clone, Plasmid_1, was used as a template for a subsequent round of PCR amplification.

PCR amplification was performed using Plasmid_1, forward primer IoE3 (SEQ ID NO: 37) and reverse primer IoE4 (SEQ ID NO: 38). PCR amplification and cloning were performed using the procedure described above and the following PCR conditions: 95° C. for 5 minutes, 32 cycles of (95° C. for 30 seconds, 65° C. for 30 seconds, 72° C. for 1 minute), followed by 5 minutes at 72° C. The PCR product was purified and cloned into a pET24a plasmid using NdeI and HindIII restriction sites. A sequence verified clone, Plasmid_2, was used as a template for a subsequent round of PCR amplification.

PCR amplification was performed using Plasmid_2, forward primer IoE5 (SEQ ID NO: 39) and reverse primer IoE6 (SEQ ID NO: 40). PCR amplification and cloning were performed using the procedure described above and the following PCR conditions: 95° C. for 5 minutes, followed by 95° C. for 30 seconds, 58° C. for 30 seconds, 72° C. for 1 minute in 35 cycles, with a final 5 minute extension at 72° C. PCR products were separated electrophoretically using 1.0% agarose gel, and stained with ethidium bromide. The DNA fragment was excised from the gel, extracted and cloned into a pET24a plasmid. A sequence verified clone, Plasmid_3, was used as a template for a subsequent round of PCR amplification.

PCR amplification was performed using Plasmid_3, forward primer IoE7 (SEQ ID NO: 41) and reverse primer IoE8

(SEQ ID NO: 42). PCR amplification and cloning were performed using the procedure described above and the following PCR conditions: 95° C. for 5 minutes, followed by 95° C. for 30 seconds, 55° C. for 30 seconds, 72° C. for 1 minute in 28 cycles, with a final 5 minute extension at 72° C. PCR products were separated electrophoretically using 1.0% agarose gel, and stained with ethidium bromide. The DNA fragment was excised from the gel, extracted and cloned into a pET24a plasmid. A sequence verified clone, Plasmid_4, was used as a template for a subsequent round of PCR amplification.

PCR amplification was performed using Plasmid_4, forward primer IoE9 (SEQ ID NO: 43) and reverse primer IoE10 (SEQ ID NO: 44). PCR amplification and cloning were performed using the procedure described above and the following PCR conditions: 95° C. for 5 minutes, followed by 95° C. for 30 seconds, 53° C. for 30 seconds, 72° C. for 1 minute in 33 cycles, with a final 5 minute extension at 72° C. PCR products were separated electrophoretically using 1.0% agarose gel, and stained with ethidium bromide. The DNA fragment was excised from the gel, extracted and cloned into a pET24a plasmid. A sequence verified clone, Plasmid_5, was used as a template for a subsequent round of PCR amplification.

PCR amplification was performed using Plasmid_5, forward primer IoE11 (SEQ ID NO: 45) and reverse primer IoE12 (SEQ ID NO: 46). PCR amplification and cloning were performed using the procedure described above and the following PCR conditions: 95° C. for 5 minutes, followed by 95° C. for 30 seconds, 57° C. for 30 seconds, 72° C. for 1 minute in 30 cycles, with a final 5 minute extension at 72° C. PCR products were separated electrophoretically using 1.0% agarose gel, and stained with ethidium bromide. The DNA fragment was excised from the gel, extracted and cloned into a pET24a plasmid. A sequence verified clone, Plasmid_6, was used as a template for a subsequent round of PCR amplification.

PCR amplification was performed using Plasmid_6, forward primer IoE13 (SEQ ID NO: 47) and reverse primer IoE14 (SEQ ID NO: 48). PCR amplification and cloning were performed using the procedure described above and the following PCR conditions: 95° C. for 5 minutes, followed by 95° C. for 30 seconds, 51° C. for 30 seconds, 72° C. for 1 minute in 32 cycles, with a final 5 minute extension at 72° C. PCR products were separated electrophoretically using 1.0% agarose gel, and stained with ethidium bromide. The DNA fragment was excised from the gel, extracted and cloned into a pET24a plasmid. A sequence verified clone, Plasmid_7, was used as a template for a subsequent round of PCR amplification.

PCR amplification was performed using Plasmid_7, forward primer IoE15 (SEQ ID NO: 49) and reverse primer IoE16 (SEQ ID NO: 50). PCR amplification and cloning were performed using the procedure described above and the following PCR conditions: 95° C. for 5 minutes, followed by 95° C. for 30 seconds, 54° C. for 30 seconds, 72° C. for 1 minute in 32 cycles, with a final 5 minute extension at 72° C. PCR products were separated electrophoretically using 1.0% agarose gel, and stained with ethidium bromide. The DNA fragment was excised from the gel, extracted and cloned into a pET24a plasmid. A sequence verified clone, Plasmid_8, was used as a template for a subsequent round of PCR amplification.

PCR amplification was performed using Plasmid_8, forward primer IoE17 (SEQ ID NO: 51) and reverse primer IoE18 (SEQ ID NO: 52). PCR amplification and cloning were performed using the procedure described above and the following PCR conditions: 95° C. for 5 minutes, followed by 95° C. for 30 seconds, 52° C. for 30 seconds, 72° C. for 1 minute in 32 cycles, with a final 5 minute extension at 72° C. PCR products were separated electrophoretically using 1.0% agarose gel, and stained with ethidium bromide. The DNA fragment was excised from the gel, extracted and cloned into a pET24a plasmid. The ligation mixture was transformed into DH5alpha strain of *Escherichia coli* cells and transformants were selected on LB plates containing ampicillin. A sequence verified clone, Plasmid_9 contains the CRYA_1B (SEQ ID NO: 25) in the correct reading frame.

Expression of Recombinant Polypeptide CRYA_1B

Figure 2:
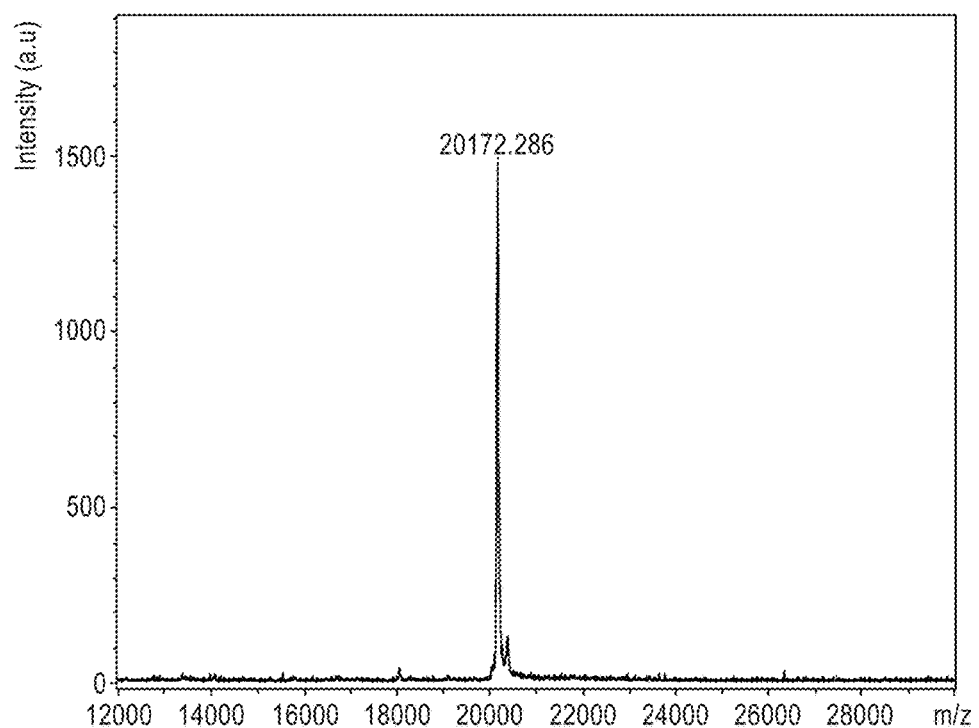
FIG. 2 shows a graph depicting the molecular weight of CRYA_1B recombinant polypeptide (SEQ ID NO: 9) of about 20 kDa as determined by mass spectrometry.
Figure 3A:
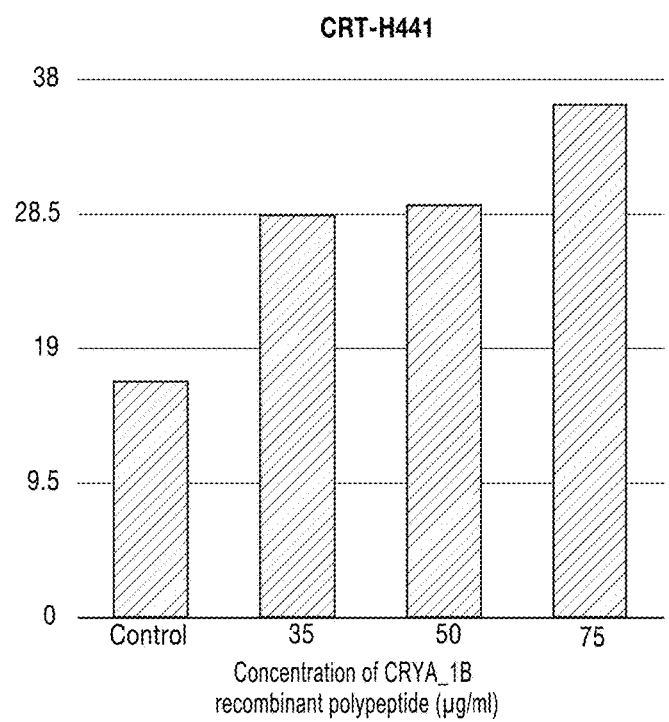
FIG. 3A shows a bar graph quantifying the percentage of cells that express CRT(Caltreticulin) following treatment of H441 human lung cancer cell lines (HTB-174, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 µg/ml and the H441 cells were incubated for 1 hour at 37° C. The CRT-expressing H441 cells were determined by FACSCalibur (BD Biosciences) flow cytometry using CRT mAb (Abcam).
Figure 5A:
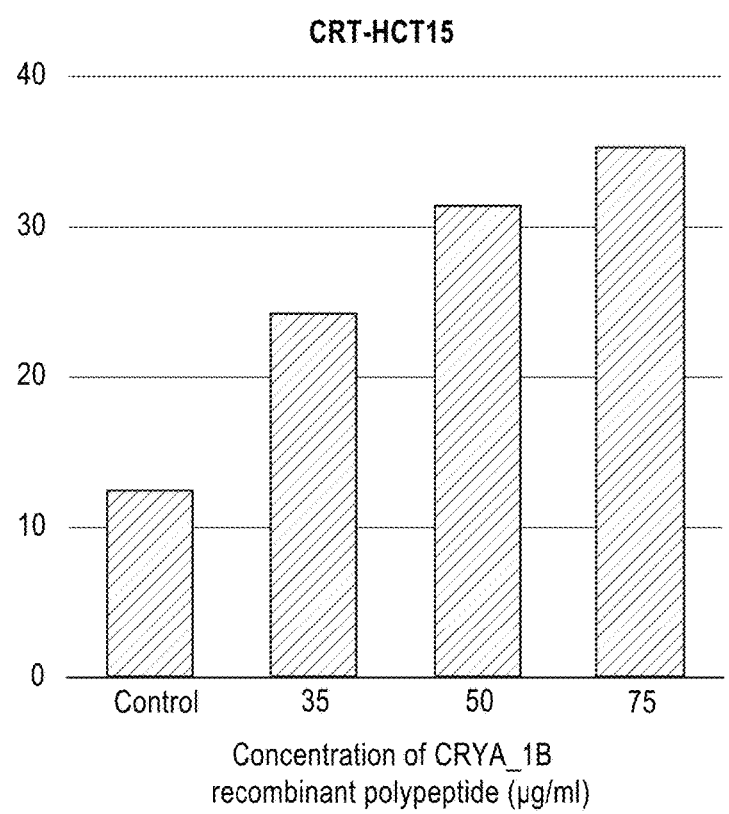
FIG. 5A shows a bar graph quantifying the percentage of cells that express CRT following treatment of HCT15 human colon cancer cell lines (CCL-225, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 µg/ml and the HCT15 cells were incubated for 55 minutes at 37° C. The CRT-expressing HCT15 cells were determined by FACSCalibur (BD Biosciences) flow cytometry using CRT mAb (Abcam).
Figure 5B:
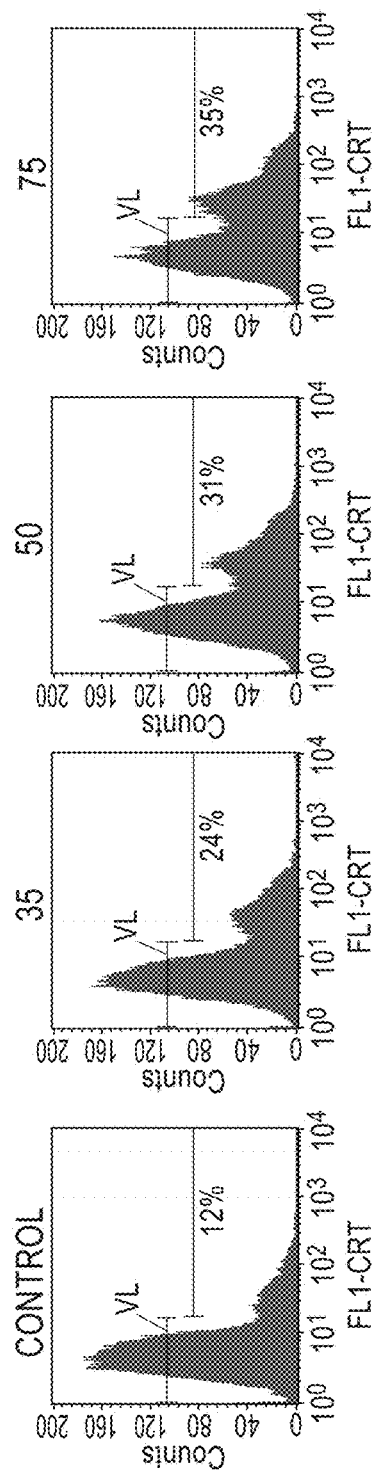
FIG. 5B shows the flow cytometry profiles used for quantification.
Figure 6A:
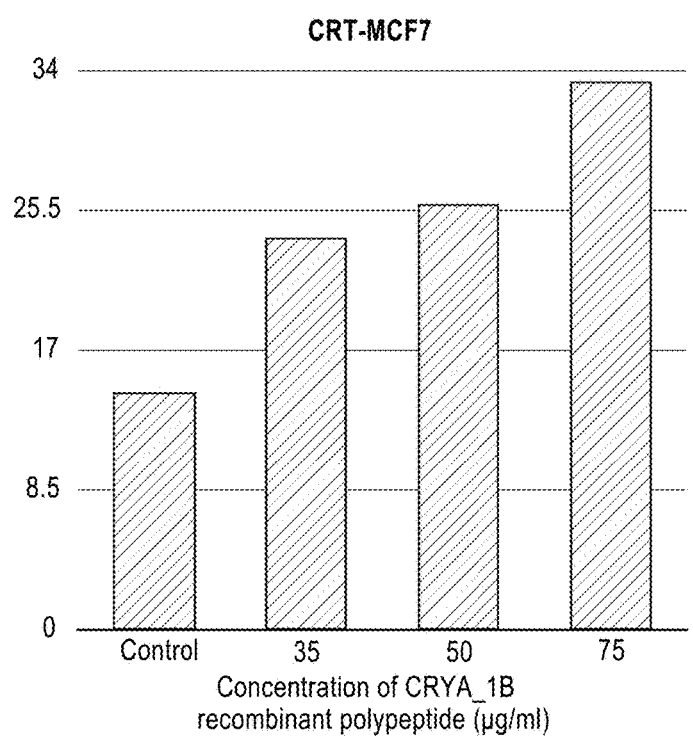
FIG. 6A shows a bar graph quantifying the percentage of cells that express CRT following treatment of MCF7 human breast cancer cell lines (HTB-22, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 µg/ml and the MCF7 cells were incubated for 1 hour and 10 minutes at 37° C. The CRT-expressing MCF7 cells were determined by FACSCalibur (BD Biosciences) flow cytometry using CRT mAb (Abcam).
Figure 7B:
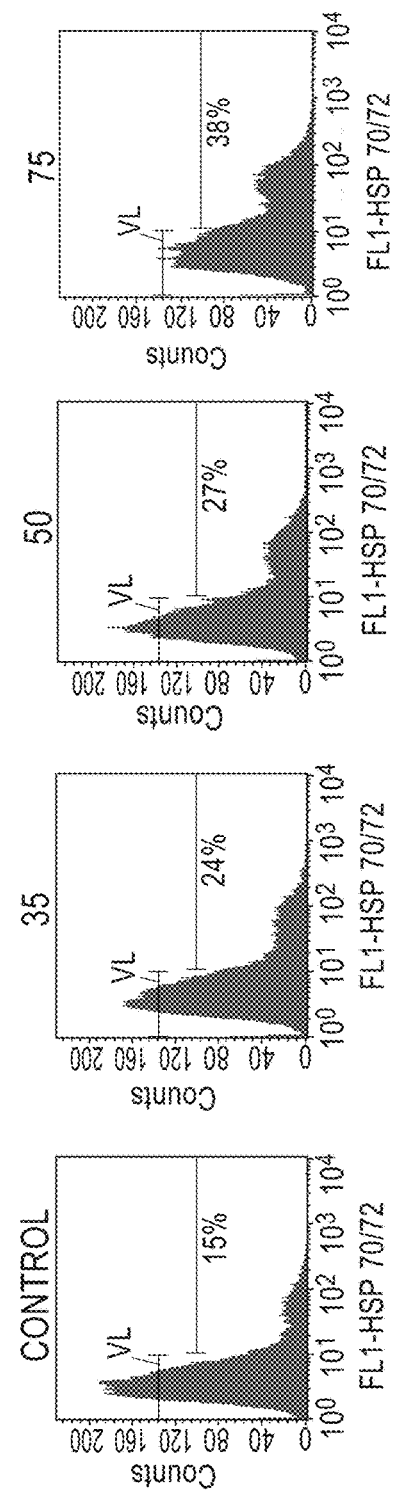
FIG. 7B shows the flow cytometry profiles used for quantification.
Figure 8A:
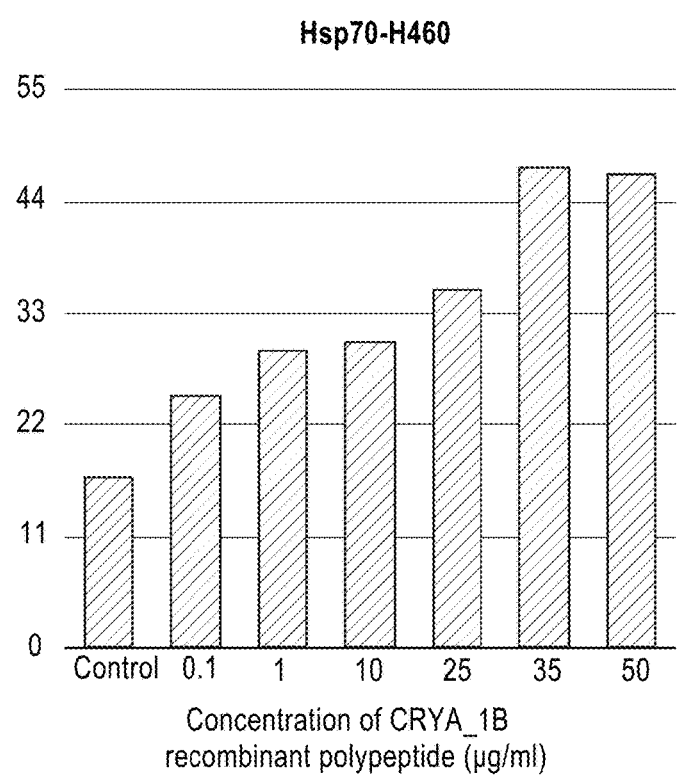
FIG. 8A shows a bar graph quantifying the percentage of cells that express HSP70 following treatment of H460 human lung cancer cell lines (HTB-177, ATCC) with various concentrations of CRYA_1B recombinant polypeptide (SEQ ID NO: 9). The stock CRYA_1B recombinant polypeptide (SEQ ID NO: 9) was diluted to the final concentration of 0.1, 1, 10, 25, 35, 50 µg/ml and the H460 cells were incubated for 1 hour and 15 minutes at 37° C. The Hsp70-expressing H460 cells were determined by FACSCalibur (BD Biosciences) flow cytometry using Hsp70 mAb (Enzo Life Sciences).
Figure 8B:
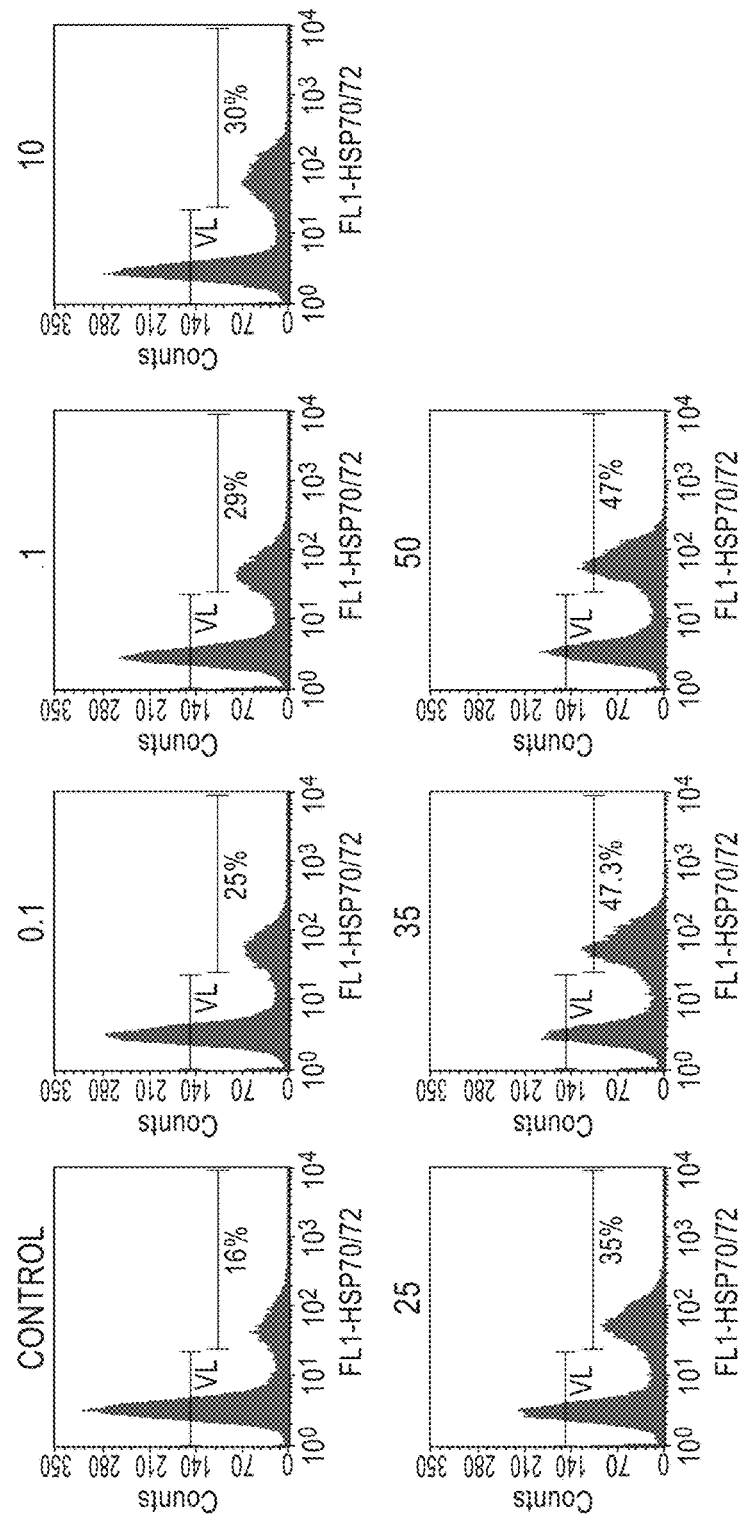
FIG. 8B shows the flow cytometry profiles used for quantification.
Figure 9A:
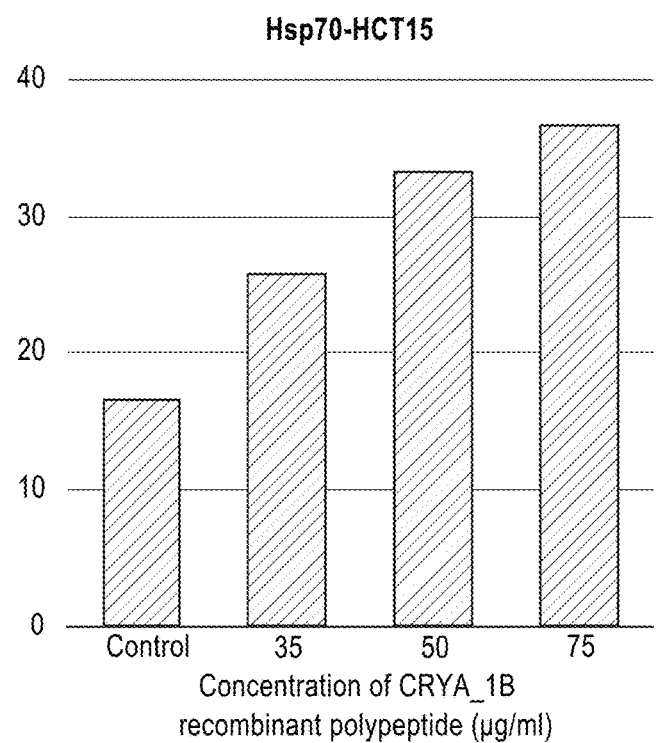
FIG. 9A shows a bar graph quantifying the percentage of cells that express HSP70 following treatment of HCT15 human colon cancer cell lines (CCL-225, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 µg/ml and the HCT15 cells were incubated for 1 hour and 50 minutes at 37° C. The Hsp70-expressing HCT15 cells were determined by FACSCalibur (BD Biosciences) flow cytometry using Hsp70 mAb (Enzo Life Sciences).
Figure 9B:
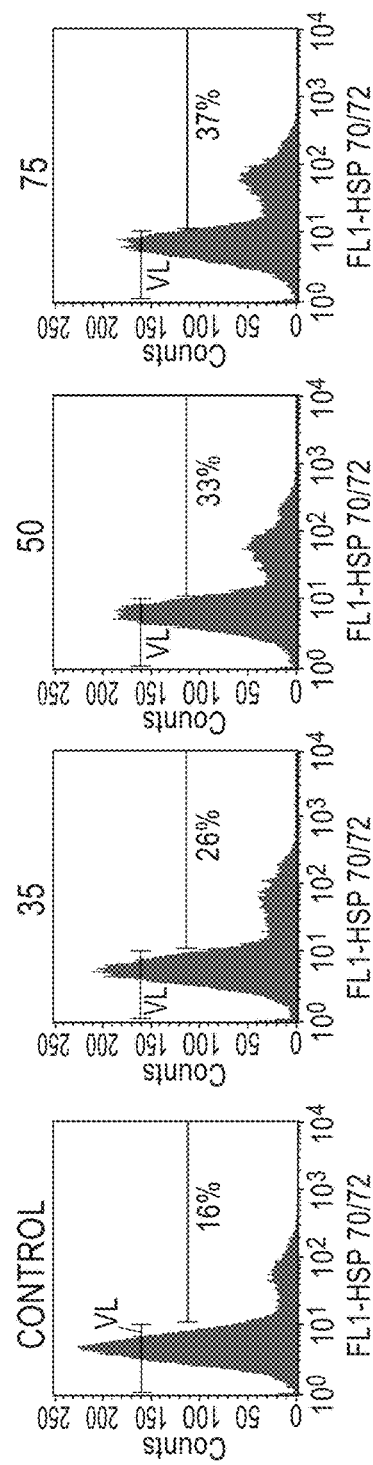
FIG. 9B shows the flow cytometry profiles used for quantification.
Figure 10A:
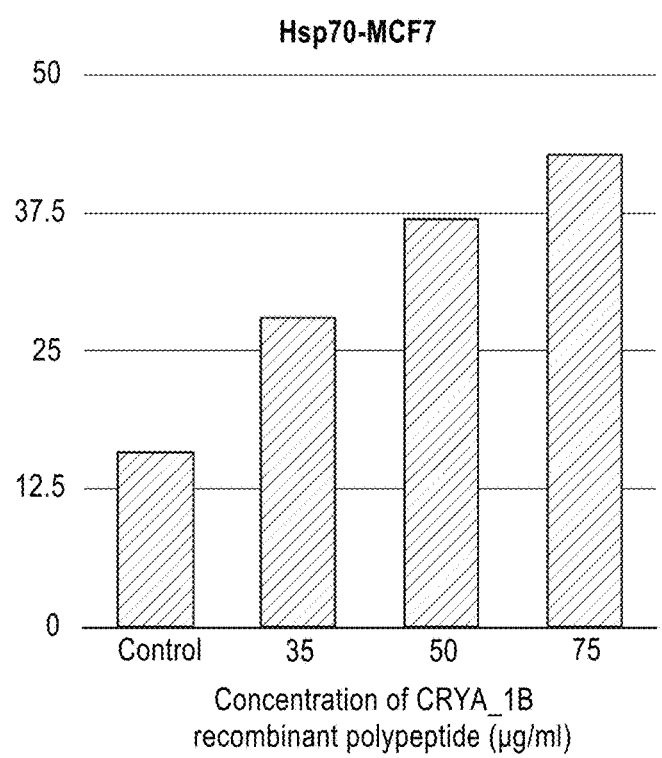
FIG. 10A shows a bar graph quantifying the percentage of cells that express HSP70 following treatment of MCF7 human breast cancer cell lines (HTB-22, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 µg/ml and the MCF7 cells were incubated for 1 hour and 40 minutes at 37° C. The Hsp70-expressing MCF7 cells were determined by FACSCalibur (BD Biosciences) flow cytometry using Hsp70 mAb (Enzo Life Sciences).
Figure 10B:
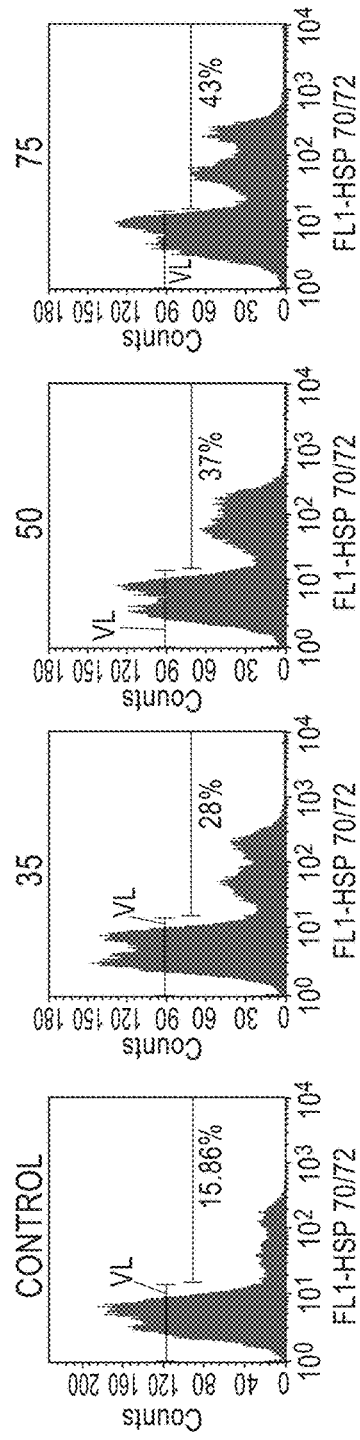
FIG. 10B shows the flow cytometry profiles used for quantification.
Figure 11A:
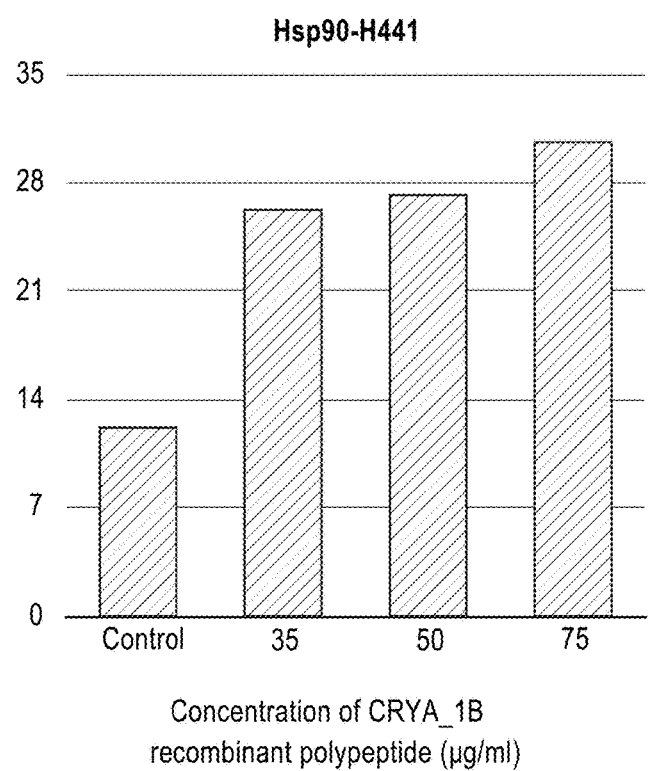
FIG. 11A shows a bar graph quantifying the percentage of cells that express HSP90 (90 kDa heat shock protein) following treatment of H441 human lung cancer cell lines (HTB-174, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 µg/ml and the H441 cells were incubated for 1 hour and 40 minutes at 37° C. The Hsp90-expressing H441 cells were determined by FACSCalibur (BD Biosciences) flow cytometry using Hsp90 mAb (Enzo Life Sciences).
Figure 12A:
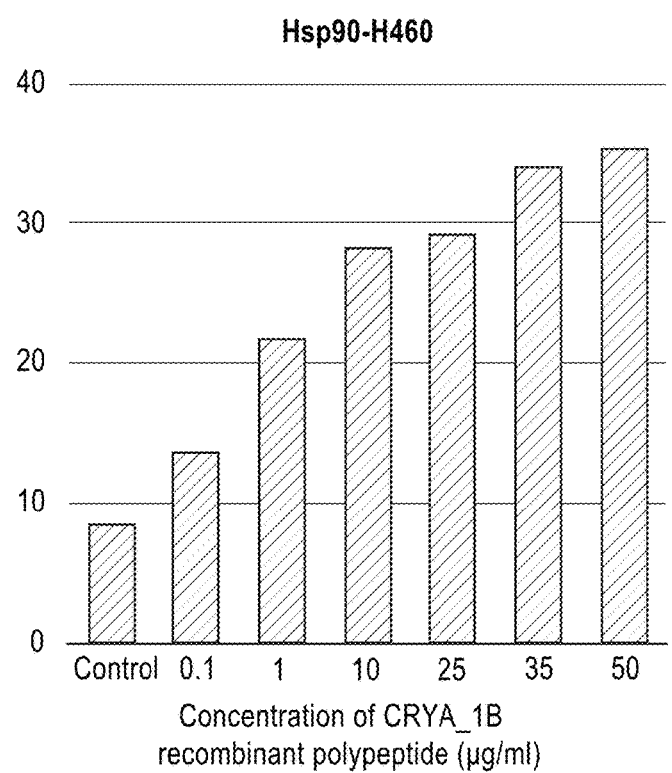
FIG. 12A shows a bar graph quantifying the percentage of cells that express HSP90 following treatment of H460 human lung cancer cell lines (HTB-177, ATCC) with various concentrations of CRYA_1B recombinant polypeptide (SEQ ID NO: 9). The stock CRYA_1B recombinant polypeptide (SEQ ID NO: 9) was diluted to the final concentration of 0.1, 1, 10, 25, 35, 50 µg/ml and the H460 cells were incubated for 1 hour and 5 minutes at 37° C. The Hsp90-expressing H460 cells were determined by FACSCalibur (BD Biosciences) flow cytometry using Hsp90 mAb (Enzo Life Sciences).
Figure 13A:
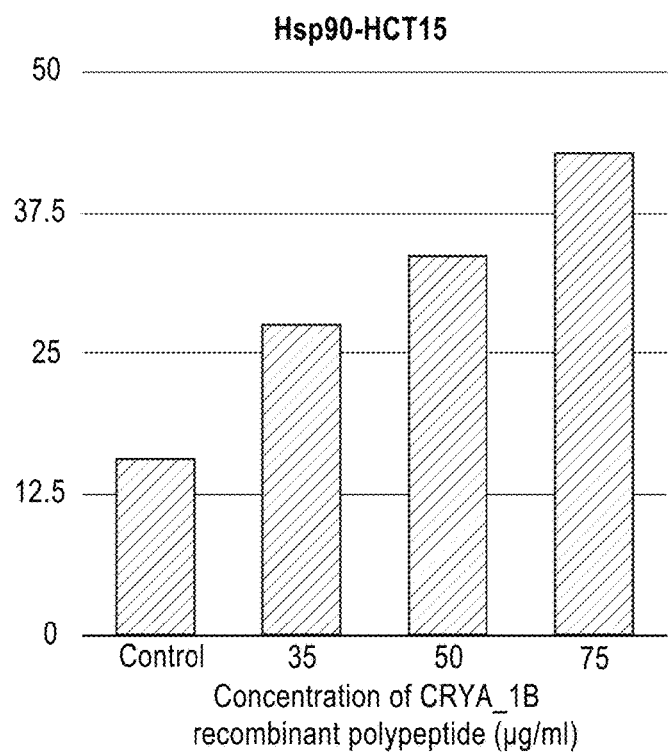
FIG. 13A shows a bar graph quantifying the percentage of cells that express HSP90 following treatment of HCT15 human colon cancer cell lines (CCL-225, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 µg/ml and the HCT15 cells were incubated for 1 hour and 30 minutes at 37° C. The Hsp90-expressing HCT15 cells were determined by FACSCalibur (BD Biosciences) flow cytometry using Hsp90 mAb (Enzo Life Sciences).
Figure 13B:
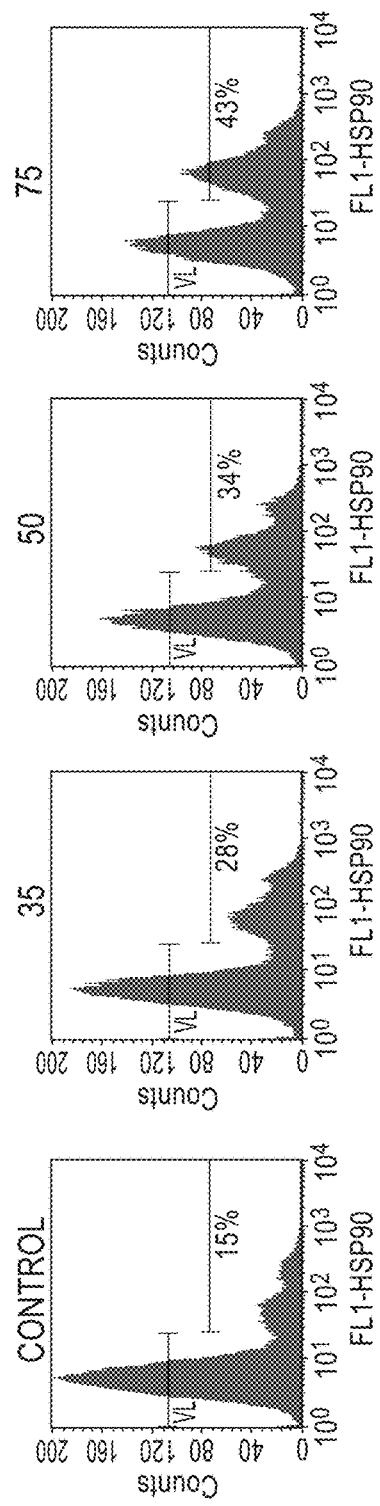
FIG. 13B shows the flow cytometry profiles used for quantification.
Figure 14A:
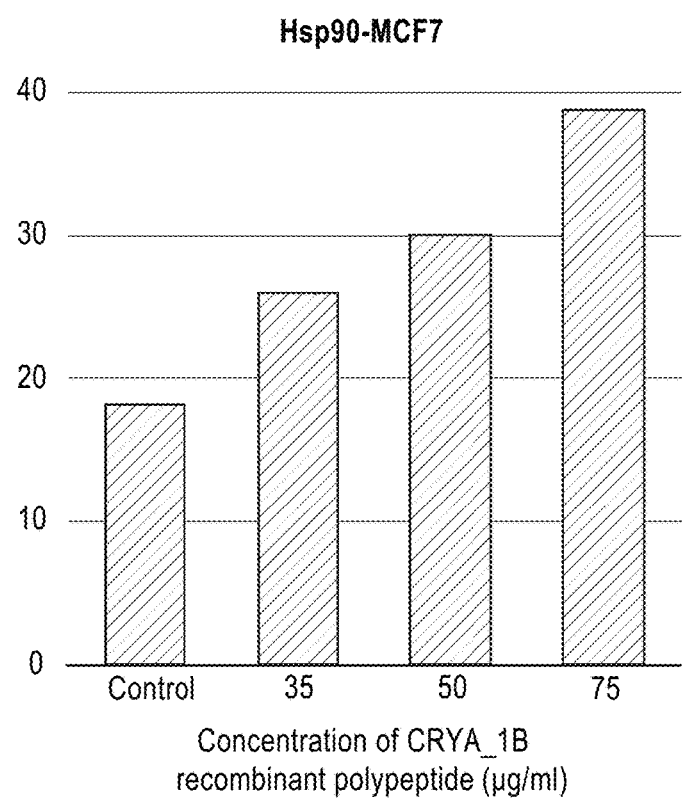
FIG. 14A shows a bar graph quantifying the percentage of cells that express HSP90 following treatment of MCF7 human breast cancer cell lines (HTB-22, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 µg/ml and the MCF7 cells were incubated for 1 hour and 45 minutes at 37° C. The Hsp90-expressing MCF7 cells were determined by FACSCalibur (BD Biosciences) flow cytometry using Hsp90 mAb (Enzo Life Sciences).
Figure 14B:
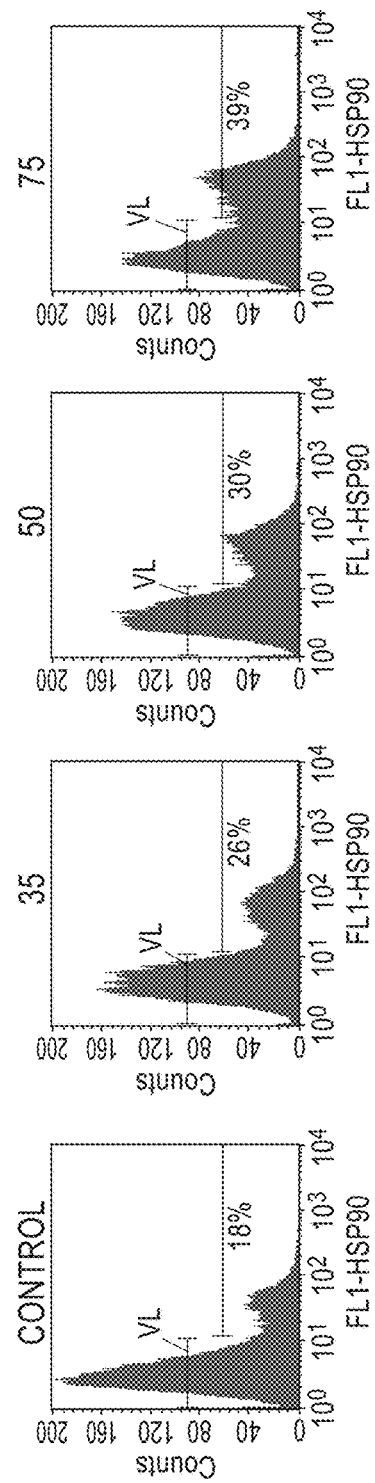
FIG. 14B shows the flow cytometry profiles used for quantification.
Figure 15A:
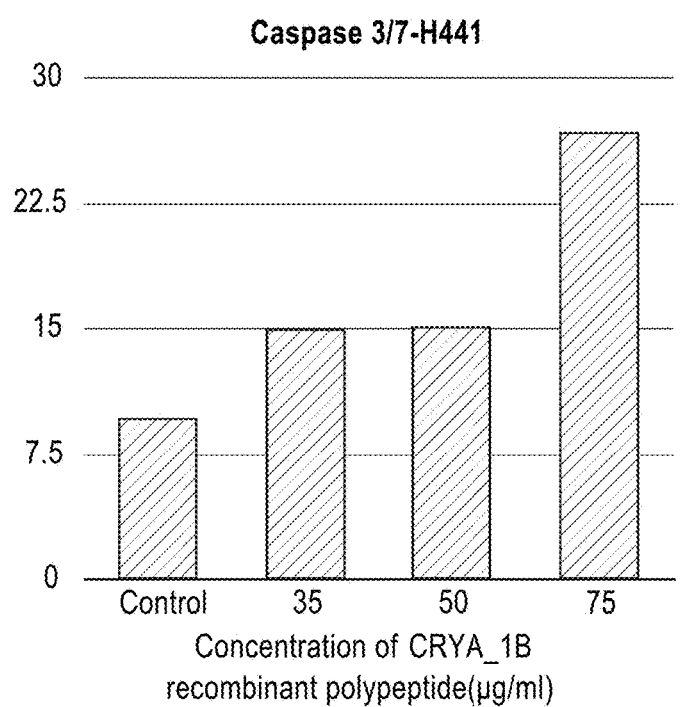
FIG. 15A shows a bar graph quantifying the percentage of cells that express Caspase 3/7 following treatment of H441 human lung cancer cell lines (HTB-174, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50 and 75 µg/ml and the H441 cells were incubated for 2 hours and 45 minutes at 37° C. The H441 cells were determined by FACSCalibur (BD Biosciences) flow cytometry using Caspase 3/7 (Invitrogen) assay.
Figure 15B:
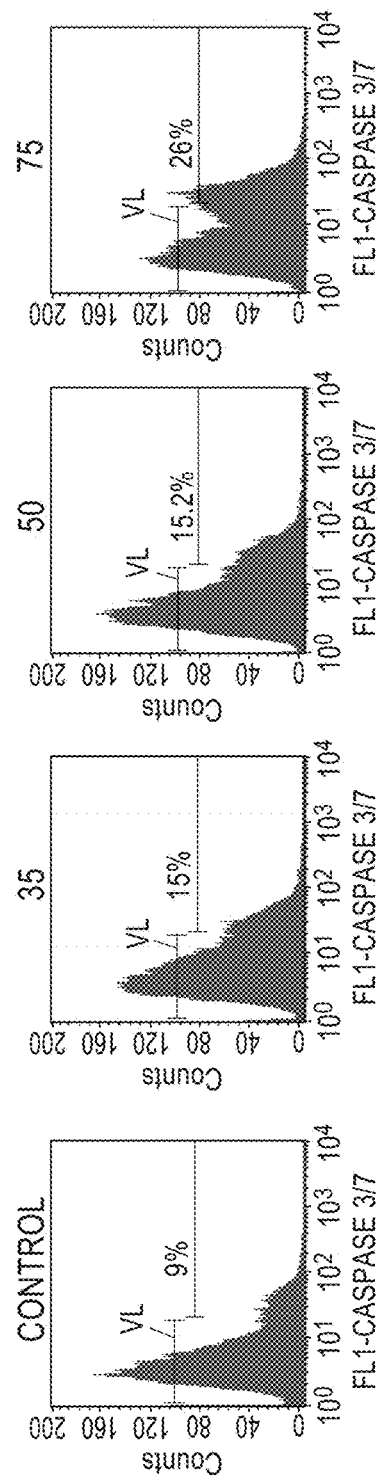
FIG. 15B shows the flow cytometry profiles used for quantification.
Figure 16A:
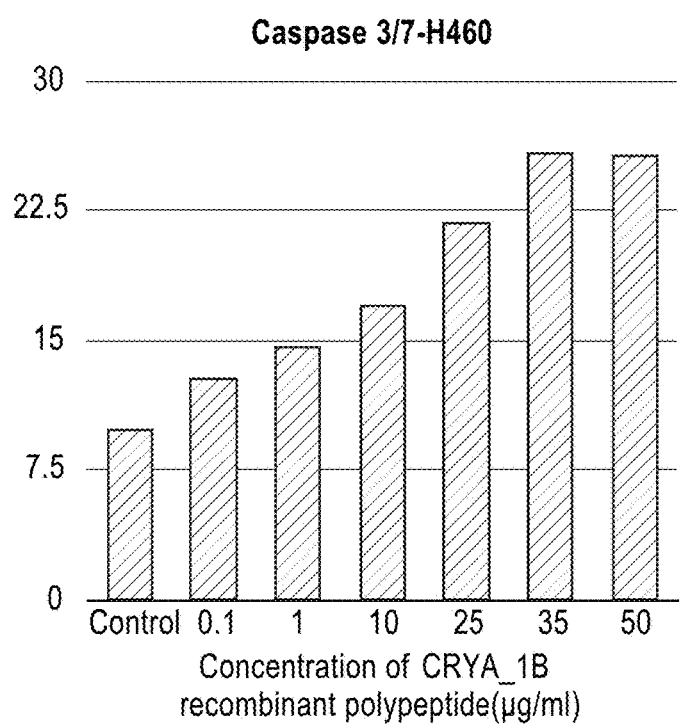
FIG. 16A shows a bar graph quantifying the percentage of cells that express Caspase 3/7 following treatment of H460 human lung cancer cell lines (HTB-177, ATCC) with various concentrations of CRYA_1B recombinant polypeptide (SEQ ID NO: 9). The stock CRYA_1B recombinant polypeptide (SEQ ID NO: 9) was diluted to the final concentration of 0.1, 1, 10, 25, 35 and 50 µg/ml and the H460 cells were incubated for 2 hours and 45 minutes at 37° C. The H460 cells were determined by FACSCalibur (BD Biosciences) flow cytometry using Caspase 3/7 (Invitrogen) assay.
Figure 16B:
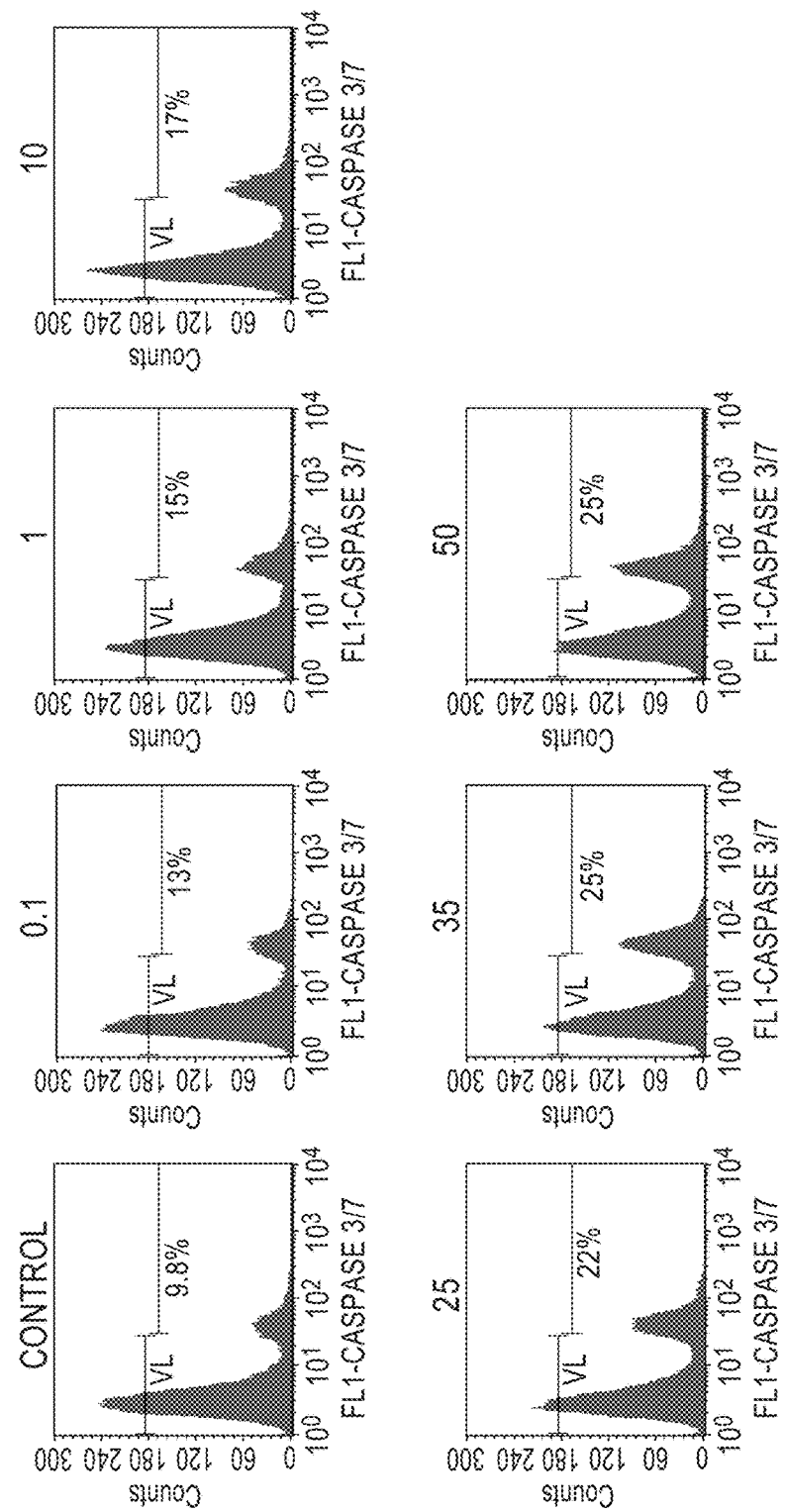
FIG. 16B shows the flow cytometry profiles used for quantification.
Figure 17A:
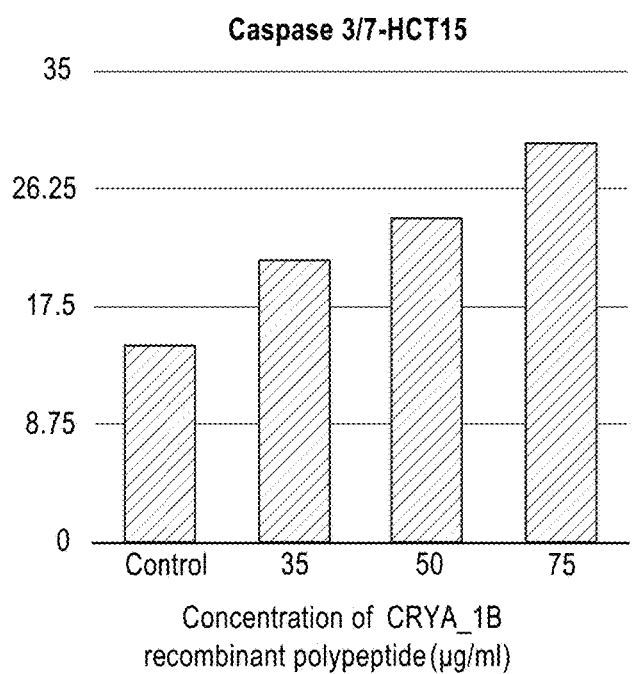
FIG. 17A shows a bar graph quantifying the percentage of cells that express Caspase 3/7 following treatment of HCT15 human colon cancer cell lines (CCL-225, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 µg/ml and the HCT15 cells were incubated for 2 hours and 30 minutes at 37° C. The HCT15 cells were determined by FACSCalibur (BD Biosciences) flow cytometry using Caspase 3/7 (Invitrogen) assay.
Figure 18A:
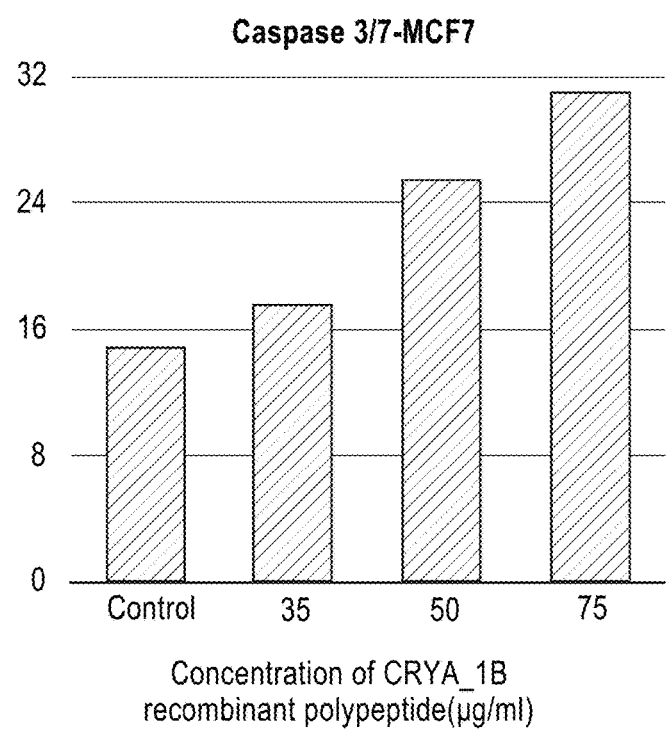
FIG. 18A shows a bar graph quantifying the percentage of cells that express Caspase 3/7 following treatment of MCF7 human breast cancer cell lines (HTB-22, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 µg/ml and the MCF7 cells were incubated for 2 hours and 45 minutes at 37° C. The MCF7 cells were determined by FACSCalibur (BD Biosciences) flow cytometry using Caspase 3/7 (Invitrogen) assay.

Plasmid_9 was transformed into the expression *Escherichia coli* strain BL21, and the ampicillin-resistant colonies were selected. The expected molecular weight for CRYA_1B recombinant polypeptide was 20 kDa (FIG. 2). A single colony from Luria-Betani (LB)-agar plate supplemented with 100 µg/ml ampicillin was selected. In this preparation, a 50 ml conical tube containing 3 ml of LB medium (10 g tryptone, 10 g NaCl and 5 g yeast extract per L) and 100 µg/ml of ampicillin was inoculated with a single colony and grown overnight in a shaking incubator set at 37° C. and 200 RPM. The culture was further expanded by adding 3 ml of the culture into a sterile 500 ml Erlenmeyer flask containing 100 ml of 2YT medium (16 g tryptone, 15 g yeast extract and 8 g NaCl per L) and 100 µg/ml of ampicillin and grown overnight in a shaking incubator set at 37° C. and 200 RPM. This resulted in a seed culture.

A 6 L bioreactor was used to further expand the seed culture. 4 L of 2YT medium containing 100 µg/ml of ampicillin was inoculated with 100 ml of seed culture grown overnight in a shaking incubator set at 37° C. and 200 RPM. In the bioreactor, cultures were incubated at 37° C., airflow and agitation of 2 SLPM (standard liners per minute) and 200 RPM. When the OD600 reached 0.65 to 0.75, protein overexpression was induced with 1.0 mM Isoropyl-β-D-thiogalactopyranoside (IPTG). The cells were allowed to grow for 7 to 8 hours and the agitation speed, temperature and air flow were set to 400 RPM, 28° C. and 4 SLPM, respectively. To control foaming, Polyglycol P-2000 antifoam was added as required. After 7 to 8 hours of induction, the cells were harvested by centrifugation at 8000 rpm for 15 minutes at 4° C. The cell pellets were frozen and stored at −80° C.

Purification of Recombinant Polypeptide CRYA_1B

In this preparation, the pellets, equivalent to 6 g of CRYA_1B recombinant polypeptide (SEQ ID NO: 9) was resuspended in 40 ml of Buffer A (50 mM Tris-HCl buffer) and disrupted by sonication on ice (28 cycles of 10-s pulses with 30-s intervals, 30% amplitude using an ultrasonic cell disruptor Misonix Ultrasonic Liquid Processors S-4000, USA) to obtain the total protein extract for solubility analysis. The total protein extract was centrifuged at 14,000 rpm for 45 min at 4° C. using a Sorvall RCSC Plus (USA) ultracentrifuge using a type SS-34 rotor. The supernatant was filtered through a 0.45 µm filter (Millipore) and loaded onto a Q-Sepharose anion exchange column equilibrated in the same buffer. Q-Sepharose was packed into a C 26/40 Column (GE Healthcare) to a bed height of 20 cm. A 40 mL volume of supernatant containing CRYA_1B recombinant polypeptide (SEQ ID NO: 9) was loaded onto the column using AKTA FPLC (GE Healthcare) at a flow rate of 5 ml/min. CRYA_1B recombinant polypeptide (SEQ ID NO: 9) was eluted by a concentration gradient by using an equilibrium buffer containing 50 mM Tris-HCl, NaCl buffer and collected in a single peak based on A280 absorbance for further application on the hydrophobic interaction column. The eluents collected were analyzed by 15% SDS-polyacrylamide gel electrophoresis.

Hydrophobic Interaction Chromatography

After ion exchange chromatography, the eluted CRYA_1B recombinant polypeptide (SEQ ID NO: 9) was pooled together, concentrated by Amicon Ultra 15 ml Centrifugal Filter (Merck), and subsequently added to the saturated ammonium sulphate buffer (50 mM Tris-HCl, 3.8 M ammonium sulphate, 1 mM DTT and 1 mM EDTA), resulting in a final concentration of 1.2 M ammonium sulphate. The concentrated product with adding ammonium sulphate was filtered using a 0.45 μm syringe filter (Millipore) and loaded to Hydrophobic Interaction Chromatography column (C 10/20 column, Ge Healthcare) at a flow rate of 2 ml/min. Source 15PHE (GE Healthcare) was packed into C 10/20 column (GE Healthcare) to a bed height of 10 cm and pre-equilibrated with buffer A (50 mM Tris-HCl, 1.2 M ammonium sulphate, 10% glycerol, 1 mM DTT and 1 mM EDTA). The column was washed with buffer A and the protein elution using buffer B (50 mM Tris-HCl, 10% glycerol, 1 mM DTT and 1 mM EDTA) was achieved with a linear gradient with decreasing ammonium sulphate and increasing glycerol. The eluted protein was analyzed by 15% SDS-PAGE. The fractions were further concentrated by Amicon Ultra 15 ml Centrifugal Filter (Merck).

Buffer Exchange Using Gel Filtration

The purified recombinant polypeptide was further exchanged into PBS buffer by using a Sephadex G-25 column. Sephadex G-25 was packed into a C 26/100 column (GE Healthcare) to a bed height of 85 cm and pre-equilibrated with PBS buffer at a flow rate of 1 ml/min. The concentrated protein was eluted after 2.5 hours and analyzed by 15% SDS-PAGE. The resulting eluates were then concentrated by Amicon Ultra 15 ml Centrifugal Filter (Merck).

Example 2: Methods of Inducing or Enhancing an Immune Response

Cancer cell lines were treated with CRYA_1B recombinant polypeptide (SEQ ID NO: 9), CRYA_1B recombinant polypeptide was diluted to various concentrations and incubated with human cancer cell lines H441 (lung cancer, HTB-174, ATCC), H460 (lung cancer, HTB-177, ATCC), HCT15 (colon cancer, CCL-225, ATCC) and MCF7 (breast cancer, HTB-22, ATCC) all at 37° C. As of CRT, HSP70, HSP90, and Caspase 3/7 assay, the recombinant polypeptide incubation time for H441 is 60 min, 1 hr50 min, 1 hr40 min, and 2 hr45 min respectively, for H460 is 30 min, 1 hr15 min, 1 hr5 min, and 2 hr30 min respectively, for HCT15 is 55 min, 1 hr50 min, 1 hr30 min, and 2 hr30 min respectively, and for MCF7 is 1 hr10 min, 1 hr40 min, 1 hr45 min, and 2 hr45 min respectively. Flow cytometry was used to assess the cell surface expression of calreticulin (CRT) (FIGS. 3-6), HSP70 (FIGS. 7-10), HSP90 (FIGS. 11-14) and Caspase 3/7 (FIGS. 15-18) in cells treated with CRYA_1B recombinant polypeptide and in untreated control cells. This was performed using a FACSCalibur (BD Biosciences) using CRT mAb (Abcam), HSP70 mAb (Enzo Life Sciences), HSP90 mAb (Enzo Life Sciences) and Caspase 3/7 (Invitrogen assay), respectively.

What is claimed is:

1. A recombinant polypeptide comprising an amino acid sequence of SEQ ID NO: 9.

2. A pharmaceutical composition comprising the recombinant polypeptide of claim 1 and a pharmaceutically acceptable carrier.

3. The pharmaceutical composition of claim 2, wherein the final NaCl concentration is 0.4M-1.0M and the pharmaceutically acceptable carrier comprises a buffer solution of pH 7.5-9.0.

* * * * *

SEQUENCE LISTING

<160> NUMBER OF SEQ ID NOS: 52

<210> SEQ ID NO 1
<211> LENGTH: 173
<212> TYPE: PRT
<213> ORGANISM: Anser cygnoides

<400> SEQUENCE: 1

Met Asp Ile Thr Ile Gln His Pro Trp Phe Lys Arg Ala Leu Gly Pro
1               5                   10                  15

Leu Ile Pro Ser Arg Leu Phe Asp Gln Phe Phe Gly Glu Gly Leu Leu
            20                  25                  30

Glu Tyr Asp Leu Leu Pro Leu Phe Ser Ser Thr Ile Ser Pro Tyr Tyr
        35                  40                  45

Arg Gln Ser Leu Phe Arg Ser Val Leu Glu Ser Gly Ile Ser Glu Val
    50                  55                  60

Arg Ser Asp Arg Asp Lys Phe Thr Ile Met Leu Asp Val Lys His Phe
65                  70                  75                  80

Ser Pro Glu Asp Leu Ser Val Lys Ile Ile Asp Phe Val Glu Ile
                85                  90                  95

His Gly Lys His Ser Glu Arg Gln Asp Asp His Gly Tyr Ile Ser Arg
            100                 105                 110

Glu Phe His Arg Arg Tyr Arg Leu Pro Ala Asn Val Asp Gln Ser Ala
        115                 120                 125

Ile Thr Cys Ser Leu Ser Gly Asp Gly Met Leu Thr Phe Ser Gly Pro
    130                 135                 140

Lys Val Pro Ser Asn Met Asp Pro Thr His Ser Glu Arg Pro Ile Pro
145                 150                 155                 160

```
Val Ser Arg Glu Glu Lys Pro Thr Ser Ala Pro Ser Ser
              165                 170
```

```
<210> SEQ ID NO 2
<211> LENGTH: 173
<212> TYPE: PRT
<213> ORGANISM: Rhea americana

<400> SEQUENCE: 2
```

```
Met Asp Ile Thr Ile Gln His Pro Trp Phe Lys Arg Ala Leu Gly Pro
1               5                   10                  15

Leu Ile Pro Ser Arg Leu Phe Asp Gln Phe Gly Glu Gly Leu Leu
            20                  25                  30

Glu Tyr Asp Leu Leu Pro Leu Phe Ser Ser Thr Ile Ser Pro Tyr Tyr
            35                  40                  45

Arg Gln Ser Leu Phe Arg Ser Val Leu Glu Ser Gly Ile Ser Glu Val
    50                  55                  60

Arg Ser Asp Arg Glu Lys Phe Thr Ile Met Leu Asp Val Lys His Phe
65                  70                  75                  80

Ser Pro Glu Asp Leu Ser Val Lys Ile Ile Asp Asp Phe Val Glu Ile
                85                  90                  95

His Gly Lys His Ser Glu Arg Gln Asp Asp His Gly Tyr Ile Ser Arg
            100                 105                 110

Glu Phe His Arg Arg Tyr Arg Leu Pro Ser Asn Val Asp Gln Ser Ala
        115                 120                 125

Ile Thr Cys Ser Leu Ser Ser Asp Gly Met Leu Thr Phe Ser Gly Pro
    130                 135                 140

Lys Val Gln Ala Asn Met Asp Pro Ser His Ser Glu Arg Pro Ile Pro
145                 150                 155                 160

Val Ser Arg Glu Glu Lys Pro Thr Ser Ala Pro Ser Ser
                165                 170
```

```
<210> SEQ ID NO 3
<211> LENGTH: 149
<212> TYPE: PRT
<213> ORGANISM: Anas platyrhynchos

<400> SEQUENCE: 3
```

```
Arg Ala Leu Gly Pro Leu Ile Pro Ser Arg Leu Phe Asp Gln Phe Phe
1               5                   10                  15

Gly Glu Gly Leu Leu Glu Tyr Asp Leu Leu Pro Leu Phe Ser Ser Thr
            20                  25                  30

Ile Ser Pro Tyr Tyr Arg Gln Ser Leu Phe Arg Ser Val Leu Glu Ser
        35                  40                  45

Gly Ile Ser Glu Val Arg Ser Asp Arg Asp Lys Phe Thr Ile Met Leu
    50                  55                  60

Asp Val Lys His Phe Ser Pro Glu Asp Leu Ser Val Lys Ile Ile Asp
65                  70                  75                  80

Asp Phe Val Glu Ile His Gly Lys His Ser Glu Arg Gln Asp Asp His
                85                  90                  95

Gly Tyr Ile Ser Arg Glu Phe His Arg Arg Tyr Arg Leu Pro Ala Asn
            100                 105                 110

Val Asp Gln Ser Ala Ile Thr Cys Ser Leu Ser Gly Asp Gly Met Leu
        115                 120                 125

Thr Phe Ser Gly Pro Lys Val Pro Ser Asn Met Asp Pro Thr His Ser
    130                 135                 140
```

Glu Arg Pro Ile Pro
145

<210> SEQ ID NO 4
<211> LENGTH: 174
<212> TYPE: PRT
<213> ORGANISM: Anas platyrhynchos

<400> SEQUENCE: 4

Met Asp Ile Thr Ile His Asn Pro Leu Ile Arg Arg Pro Leu Phe Ser
1               5                   10                  15

Trp Leu Ala Pro Ser Arg Ile Phe Asp Gln Ile Phe Gly Glu His Leu
            20                  25                  30

Gln Glu Ser Glu Leu Leu Pro Ala Ser Pro Ser Leu Ser Pro Phe Leu
        35                  40                  45

Met Arg Ser Pro Ile Phe Arg Met Pro Ser Trp Leu Glu Thr Gly Leu
    50                  55                  60

Ser Glu Met Arg Leu Glu Lys Asp Lys Phe Ser Val Asn Leu Asp Val
65                  70                  75                  80

Lys His Phe Ser Pro Glu Glu Leu Lys Val Lys Val Leu Gly Asp Met
                85                  90                  95

Val Glu Ile His Gly Lys His Glu Glu Arg Gln Asp Glu His Gly Phe
            100                 105                 110

Ile Ala Arg Glu Phe Asn Arg Lys Tyr Arg Ile Pro Ala Asp Val Asp
        115                 120                 125

Pro Leu Thr Ile Thr Ser Ser Leu Ser Leu Asp Gly Val Leu Thr Val
    130                 135                 140

Ser Ala Pro Arg Lys Gln Ser Asp Val Pro Glu Arg Ser Ile Pro Ile
145                 150                 155                 160

Thr Arg Glu Glu Lys Pro Ala Ile Ala Gly Ala Gln Arg Lys
                165                 170

<210> SEQ ID NO 5
<211> LENGTH: 173
<212> TYPE: PRT
<213> ORGANISM: Homo sapiens

<400> SEQUENCE: 5

Met Asp Val Thr Ile Gln His Pro Trp Phe Lys Arg Thr Leu Gly Pro
1               5                   10                  15

Phe Tyr Pro Ser Arg Leu Phe Asp Gln Phe Phe Gly Glu Gly Leu Phe
            20                  25                  30

Glu Tyr Asp Leu Leu Pro Phe Leu Ser Ser Thr Ile Ser Pro Tyr Tyr
        35                  40                  45

Arg Gln Ser Leu Phe Arg Thr Val Leu Asp Ser Gly Ile Ser Glu Val
    50                  55                  60

Arg Ser Asp Arg Asp Lys Phe Val Ile Phe Leu Asp Val Lys His Phe
65                  70                  75                  80

Ser Pro Glu Asp Leu Thr Val Lys Val Gln Asp Asp Phe Val Glu Ile
                85                  90                  95

His Gly Lys His Asn Glu Arg Gln Asp Asp His Gly Tyr Ile Ser Arg
            100                 105                 110

Glu Phe His Arg Arg Tyr Arg Leu Pro Ser Asn Val Asp Gln Ser Ala
        115                 120                 125

Leu Ser Cys Ser Leu Ser Ala Asp Gly Met Leu Thr Phe Cys Gly Pro
    130                 135                 140

Lys Ile Gln Thr Gly Leu Asp Ala Thr His Ala Glu Arg Ala Ile Pro
145                 150                 155                 160

Val Ser Arg Glu Glu Lys Pro Thr Ser Ala Pro Ser Ser
                165                 170

<210> SEQ ID NO 6
<211> LENGTH: 186
<212> TYPE: PRT
<213> ORGANISM: Drosophila melanogaster

<400> SEQUENCE: 6

Met Ala Asn Ile Pro Leu Leu Leu Ser Leu Ala Asp Asp Leu Gly Arg
1               5                   10                  15

Met Ser Met Val Pro Phe Tyr Glu Pro Tyr Tyr Cys Gln Arg Gln Arg
                20                  25                  30

Asn Pro Tyr Leu Ala Leu Val Gly Pro Met Glu Gln Gln Leu Arg Gln
            35                  40                  45

Leu Glu Lys Gln Val Gly Ala Ser Ser Gly Ser Ser Gly Ala Val Ser
    50                  55                  60

Lys Ile Gly Lys Asp Gly Phe Gln Val Cys Met Asp Val Ser His Phe
65                  70                  75                  80

Lys Pro Ser Glu Leu Val Val Lys Val Gln Asp Asn Ser Val Leu Val
                85                  90                  95

Glu Gly Asn His Glu Glu Arg Glu Asp Asp His Gly Phe Ile Thr Arg
            100                 105                 110

His Phe Val Arg Arg Tyr Ala Leu Pro Pro Gly Tyr Glu Ala Asp Lys
        115                 120                 125

Val Ala Ser Thr Leu Ser Ser Asp Gly Val Leu Thr Ile Lys Val Pro
    130                 135                 140

Lys Pro Pro Ala Ile Glu Asp Lys Gly Asn Glu Arg Ile Val Gln Ile
145                 150                 155                 160

Gln Gln Val Gly Pro Ala His Leu Asn Val Lys Glu Asn Pro Lys Glu
                165                 170                 175

Ala Val Glu Gln Asp Asn Gly Asn Asp Lys
            180                 185

<210> SEQ ID NO 7
<211> LENGTH: 174
<212> TYPE: PRT
<213> ORGANISM: Drosophila melanogaster

<400> SEQUENCE: 7

Met Arg Ser Leu Pro Met Phe Trp Arg Met Ala Glu Glu Met Ala Arg
1               5                   10                  15

Met Pro Arg Leu Ser Ser Pro Phe His Ala Phe Phe His Glu Pro Pro
                20                  25                  30

Val Trp Ser Val Ala Leu Pro Arg Asn Trp Gln His Ile Ala Arg Trp
            35                  40                  45

Gln Glu Gln Glu Leu Ala Pro Pro Ala Thr Val Asn Lys Asp Gly Tyr
    50                  55                  60

Lys Leu Thr Leu Asp Val Lys Asp Tyr Ser Glu Leu Lys Val Lys Val
65                  70                  75                  80

Leu Asp Glu Ser Val Val Leu Val Glu Ala Lys Ser Glu Gln Gln Glu
                85                  90                  95

Ala Glu Gln Gly Gly Tyr Ser Ser Arg His Phe Leu Gly Arg Tyr Val
            100                 105                 110

```
Leu Pro Asp Gly Tyr Glu Ala Asp Lys Val Ser Ser Leu Ser Asp
            115                 120                 125

Asp Gly Val Leu Thr Ile Ser Val Pro Asn Pro Pro Gly Val Gln Glu
130                 135                 140

Thr Leu Lys Glu Arg Glu Val Thr Ile Glu Gln Thr Gly Glu Pro Ala
145                 150                 155                 160

Lys Lys Ser Ala Glu Glu Pro Lys Asp Lys Thr Ala Ser Gln
                165                 170

<210> SEQ ID NO 8
<211> LENGTH: 174
<212> TYPE: PRT
<213> ORGANISM: Anser cygnoides

<400> SEQUENCE: 8

Met Asp Ile Thr Ile His Asn Pro Leu Ile Arg Arg Pro Leu Phe Ser
1               5                   10                  15

Trp Leu Ala Pro Ser Arg Ile Phe Asp Gln Ile Phe Gly Glu His Leu
            20                  25                  30

Gln Glu Ser Glu Leu Leu Pro Ala Ser Pro Ser Leu Ser Pro Phe Leu
        35                  40                  45

Met Arg Ser Pro Ile Phe Arg Met Pro Ser Trp Leu Glu Thr Gly Leu
    50                  55                  60

Ser Glu Met Arg Leu Glu Lys Asp Lys Phe Ser Val Asn Leu Asp Val
65                  70                  75                  80

Lys His Phe Ser Pro Glu Glu Leu Lys Val Lys Val Leu Gly Asp Met
                85                  90                  95

Val Glu Ile His Gly Lys His Glu Glu Arg Gln Asp Glu His Gly Phe
            100                 105                 110

Ile Ala Arg Glu Phe Asn Arg Lys Tyr Arg Ile Pro Ala Asp Val Asp
        115                 120                 125

Pro Leu Thr Ile Thr Ser Ser Leu Ser Leu Asp Gly Val Leu Thr Val
    130                 135                 140

Ser Ala Pro Arg Lys Gln Ser Asp Val Pro Glu Arg Ser Ile Pro Ile
145                 150                 155                 160

Thr Arg Glu Glu Lys Pro Ala Ile Ala Gly Ala Gln Arg Lys
                165                 170

<210> SEQ ID NO 9
<211> LENGTH: 173
<212> TYPE: PRT
<213> ORGANISM: Artificial Sequence
<220> FEATURE:
<223> OTHER INFORMATION: artificial polypeptide

<400> SEQUENCE: 9

Met Asp Ile Thr Ile Gln His Pro Trp Phe Lys Arg Ala Leu Gly Pro
1               5                   10                  15

Leu Ile Pro Glu Arg Leu Phe Asp Gln Phe Phe Gly Ser Gly Leu Leu
            20                  25                  30

Ser Tyr Asp Leu Leu Pro Leu Phe Glu Glu Thr Ile Glu Pro Tyr Tyr
        35                  40                  45

Arg Gln Glu Leu Phe Arg Glu Val Leu Ser Gly Ile Glu Ser Val
    50                  55                  60

Arg Glu Asp Arg Asp Lys Phe Thr Ile Met Leu Asp Val Lys His Phe
65                  70                  75                  80

Glu Pro Ser Asp Leu Glu Val Lys Ile Ile Asp Asp Phe Val Ser Ile
```

```
                85                  90                  95
His Gly Lys His Glu Ser Arg Gln Asp Asp His Gly Tyr Ile Glu Arg
            100                 105                 110

Ser Phe His Arg Arg Tyr Arg Leu Pro Ala Asn Val Asp Gln Glu Ala
            115                 120                 125

Ile Thr Cys Glu Leu Glu Gly Asp Gly Met Leu Thr Phe Glu Gly Pro
        130                 135                 140

Lys Val Pro Glu Asn Met Asp Pro Thr His Glu Ser Arg Pro Ile Pro
145                 150                 155                 160

Val Glu Arg Ser Ser Lys Pro Thr Glu Ala Pro Glu Glu
                165                 170

<210> SEQ ID NO 10
<211> LENGTH: 173
<212> TYPE: PRT
<213> ORGANISM: Artificial Sequence
<220> FEATURE:
<223> OTHER INFORMATION: artificial polypeptide

<400> SEQUENCE: 10

Met Asp Ile Thr Ile Gln His Pro Trp Phe Lys Arg Ala Leu Gly Pro
1               5                   10                  15

Leu Ile Pro Glu Arg Leu Phe Asp Gln Phe Gly Ser Gly Leu Leu
            20                  25                  30

Ser Tyr Asp Leu Leu Pro Leu Phe Glu Glu Thr Ile Glu Pro Tyr Tyr
        35                  40                  45

Arg Gln Glu Leu Phe Arg Glu Val Leu Ser Glu Gly Ile Glu Ser Val
    50                  55                  60

Arg Glu Asp Arg Ser Lys Phe Thr Ile Met Leu Asp Val Lys His Phe
65                  70                  75                  80

Glu Pro Ser Asp Leu Glu Val Lys Ile Ile Asp Asp Phe Val Ser Ile
                85                  90                  95

His Gly Lys His Glu Ser Arg Gln Asp Asp His Gly Tyr Ile Glu Arg
            100                 105                 110

Ser Phe His Arg Arg Tyr Arg Leu Pro Glu Asn Val Asp Gln Glu Ala
            115                 120                 125

Ile Thr Cys Glu Leu Glu Glu Asp Gly Met Leu Thr Phe Glu Gly Pro
        130                 135                 140

Lys Val Gln Ala Asn Met Asp Pro Glu His Glu Ser Arg Pro Ile Pro
145                 150                 155                 160

Val Glu Arg Ser Ser Lys Pro Thr Glu Ala Pro Glu Glu
                165                 170

<210> SEQ ID NO 11
<211> LENGTH: 149
<212> TYPE: PRT
<213> ORGANISM: Artificial Sequence
<220> FEATURE:
<223> OTHER INFORMATION: artificial polypeptide

<400> SEQUENCE: 11

Arg Ala Leu Gly Pro Leu Ile Pro Glu Arg Leu Phe Asp Gln Phe Phe
1               5                   10                  15

Gly Ser Gly Leu Leu Ser Tyr Asp Leu Leu Pro Leu Phe Glu Glu Thr
            20                  25                  30

Ile Glu Pro Tyr Tyr Arg Gln Glu Leu Phe Arg Glu Val Leu Ser Glu
        35                  40                  45
```

Gly Ile Glu Ser Val Arg Glu Asp Arg Asp Lys Phe Thr Ile Met Leu
        50                  55                  60

Asp Val Lys His Phe Glu Pro Ser Asp Leu Glu Val Lys Ile Ile Asp
 65                  70                  75                  80

Asp Phe Val Ser Ile His Gly Lys His Glu Ser Arg Gln Asp His
                 85                  90                  95

Gly Tyr Ile Glu Arg Ser Phe His Arg Tyr Arg Leu Pro Ala Asn
                100                 105                 110

Val Asp Gln Glu Ala Ile Thr Cys Glu Leu Glu Gly Asp Gly Met Leu
                115                 120                 125

Thr Phe Glu Gly Pro Lys Val Pro Glu Asn Met Asp Pro Thr His Glu
130                 135                 140

Ser Arg Pro Ile Pro
145

<210> SEQ ID NO 12
<211> LENGTH: 174
<212> TYPE: PRT
<213> ORGANISM: Artificial Sequence
<220> FEATURE:
<223> OTHER INFORMATION: artificial polypeptide

<400> SEQUENCE: 12

Met Ser Ile Thr Ile His Asn Pro Leu Ile Arg Arg Pro Leu Phe Asp
 1               5                  10                  15

Trp Leu Ala Pro Asp Arg Ile Phe Ser Gln Ile Phe Gly Glu His Leu
                20                  25                  30

Gln Glu Asp Glu Leu Leu Pro Ala Asp Pro Asp Leu Ser Pro Phe Leu
                35                  40                  45

Met Arg Asp Pro Ile Phe Arg Met Pro Asp Trp Leu Glu Thr Gly Leu
 50                  55                  60

Asp Glu Met Arg Leu Glu Lys Ser Lys Phe Asp Val Asn Leu Ser Val
 65                  70                  75                  80

Lys His Phe Asp Pro Glu Glu Leu Lys Val Lys Val Leu Gly Ser Met
                85                  90                  95

Val Glu Ile His Gly Lys His Glu Glu Arg Gln Ser Glu His Gly Phe
                100                 105                 110

Ile Ala Arg Glu Phe Asn Arg Lys Tyr Arg Ile Pro Ala Ser Val Ser
                115                 120                 125

Pro Leu Thr Ile Thr Asp Asp Leu Asp Leu Ser Gly Val Leu Thr Val
130                 135                 140

Asp Ala Pro Arg Lys Gln Asp Ser Val Pro Glu Arg Asp Ile Pro Ile
145                 150                 155                 160

Thr Arg Glu Glu Lys Pro Ala Ile Ala Gly Ala Gln Arg Lys
                165                 170

<210> SEQ ID NO 13
<211> LENGTH: 173
<212> TYPE: PRT
<213> ORGANISM: Artificial Sequence
<220> FEATURE:
<223> OTHER INFORMATION: artificial polypeptide

<400> SEQUENCE: 13

Met Asp Val Thr Ile Gln His Pro Trp Phe Lys Arg Thr Leu Gly Pro
 1               5                  10                  15

Phe Tyr Pro Glu Arg Leu Phe Asp Gln Phe Phe Gly Ser Gly Leu Phe
                20                  25                  30

```
Ser Tyr Asp Leu Leu Pro Phe Leu Glu Glu Thr Ile Glu Pro Tyr Tyr
        35                  40                  45

Arg Gln Glu Leu Phe Arg Thr Val Leu Asp Glu Gly Ile Glu Ser Val
 50                  55                  60

Arg Glu Asp Arg Asp Lys Phe Val Ile Phe Leu Asp Val Lys His Phe
 65                  70                  75                  80

Glu Pro Ser Asp Leu Thr Val Lys Val Gln Asp Asp Phe Val Ser Ile
                85                  90                  95

His Gly Lys His Asn Ser Arg Gln Asp His Gly Tyr Ile Glu Arg
            100                 105                 110

Ser Phe His Arg Arg Tyr Arg Leu Pro Glu Asn Val Asp Gln Glu Ala
            115                 120                 125

Leu Glu Cys Glu Leu Glu Ala Asp Gly Met Leu Thr Phe Cys Gly Pro
130                 135                 140

Lys Ile Gln Thr Gly Leu Asp Ala Thr His Ala Ser Arg Ala Ile Pro
145                 150                 155                 160

Val Glu Arg Ser Ser Lys Pro Thr Glu Ala Pro Glu Glu
                165                 170
```

<210> SEQ ID NO 14
<211> LENGTH: 186
<212> TYPE: PRT
<213> ORGANISM: Artificial Sequence
<220> FEATURE:
<223> OTHER INFORMATION: artificial polypeptide

<400> SEQUENCE: 14

```
Met Ala Asn Ile Pro Leu Leu Ser Leu Ala Val Val Leu Gly Arg
 1               5                  10                  15

Met Ser Met Asp Pro Phe Tyr Glu Pro Tyr Tyr Cys Gln Arg Gln Arg
                20                  25                  30

Asn Pro Tyr Leu Ala Leu Asp Gly Pro Met Glu Gln Gln Leu Arg Gln
            35                  40                  45

Leu Glu Lys Gln Asp Gly Ala Ser Ser Gly Ser Ser Gly Ala Asp Ser
 50                  55                  60

Lys Ile Gly Lys Val Gly Phe Gln Asp Cys Met Val Asp Ser His Phe
 65                  70                  75                  80

Lys Pro Ser Glu Leu Asp Asp Lys Asp Gln Val Asn Ser Asp Leu Asp
                85                  90                  95

Glu Gly Asn His Glu Glu Arg Glu Val Val His Gly Phe Ile Thr Arg
            100                 105                 110

His Phe Asp Arg Arg Tyr Ala Leu Pro Pro Gly Tyr Glu Ala Val Lys
            115                 120                 125

Asp Ala Ser Thr Leu Ser Ser Val Gly Asp Leu Thr Ile Lys Asp Pro
130                 135                 140

Lys Pro Pro Ala Ile Glu Val Lys Gly Asn Glu Arg Ile Asp Gln Ile
145                 150                 155                 160

Gln Gln Asp Gly Pro Ala His Leu Asn Asp Lys Glu Asn Pro Lys Glu
                165                 170                 175

Ala Asp Glu Gln Val Asn Gly Asn Val Lys
            180                 185
```

<210> SEQ ID NO 15
<211> LENGTH: 174
<212> TYPE: PRT
<213> ORGANISM: Artificial Sequence
<220> FEATURE:
<223> OTHER INFORMATION: artificial polypeptide

<400> SEQUENCE: 15

```
Met Arg Leu Ser Pro Met Phe Trp Arg Met Ala Glu Glu Met Ala Arg
1               5                   10                  15

Met Pro Arg Ser Leu Leu Pro Phe His Ala Phe Phe His Glu Pro Pro
            20                  25                  30

Asp Trp Leu Asp Ala Ser Pro Arg Asn Trp Gln His Ile Ala Arg Trp
        35                  40                  45

Gln Glu Gln Glu Ser Ala Pro Pro Ala Thr Asp Asn Lys Val Gly Tyr
    50                  55                  60

Lys Ser Thr Ser Val Asp Lys Val Tyr Leu Glu Ser Lys Asp Lys Asp
65                  70                  75                  80

Ser Val Glu Leu Asp Asp Ser Asp Glu Ala Lys Leu Glu Gln Gln Glu
                85                  90                  95

Ala Glu Gln Gly Gly Tyr Leu Leu Arg His Phe Ser Gly Arg Tyr Asp
            100                 105                 110

Ser Pro Val Gly Tyr Glu Ala Val Lys Asp Leu Leu Ser Leu Val
        115                 120                 125

Val Gly Asp Ser Thr Ile Leu Asp Pro Asn Pro Pro Gly Asp Gln Glu
    130                 135                 140

Thr Ser Lys Glu Arg Glu Asp Thr Ile Glu Gln Thr Gly Glu Pro Ala
145                 150                 155                 160

Lys Lys Leu Ala Glu Glu Pro Lys Val Lys Thr Ala Leu Gln
                165                 170
```

<210> SEQ ID NO 16
<211> LENGTH: 174
<212> TYPE: PRT
<213> ORGANISM: Artificial Sequence
<220> FEATURE:
<223> OTHER INFORMATION: artificial polypeptide

<400> SEQUENCE: 16

```
Met Ser Ile Thr Ile His Asn Pro Leu Ile Arg Arg Pro Leu Phe Asp
1               5                   10                  15

Trp Leu Ala Pro Asp Arg Ile Phe Ser Gln Ile Phe Gly Glu His Leu
            20                  25                  30

Gln Glu Asp Glu Leu Leu Pro Ala Asp Pro Asp Leu Asp Pro Phe Leu
        35                  40                  45

Met Arg Asp Pro Ile Phe Arg Met Pro Asp Trp Leu Glu Thr Gly Leu
    50                  55                  60

Asp Glu Met Arg Leu Glu Lys Ser Lys Phe Asp Val Asn Leu Ser Val
65                  70                  75                  80

Lys His Phe Asp Pro Glu Glu Leu Lys Val Lys Val Leu Gly Ser Met
                85                  90                  95

Val Glu Ile His Gly Lys His Glu Glu Arg Gln Ser Glu His Gly Phe
            100                 105                 110

Ile Ala Arg Glu Phe Asn Arg Lys Tyr Arg Ile Pro Ala Ser Val Ser
        115                 120                 125

Pro Leu Thr Ile Thr Asp Asp Leu Asp Leu Ser Gly Val Leu Thr Val
    130                 135                 140

Asp Ala Pro Arg Lys Gln Asp Ser Val Pro Glu Arg Asp Ile Pro Ile
145                 150                 155                 160

Thr Arg Glu Glu Lys Pro Ala Ile Ala Gly Ala Gln Arg Lys
```

<210> SEQ ID NO 17
<211> LENGTH: 519
<212> TYPE: DNA
<213> ORGANISM: Anser cygnoides

<400> SEQUENCE: 17

```
atggatatta ccattcagca tccgtggttt aaacgcgcgc tgggcccgct gattccgagc      60
cgcctgtttg atcagttttt tggcgaaggc ctgctggaat atgatctgct gccgctgttt     120
agcagcacca ttagcccgta ttatcgccag agcctgtttc gcagcgtgct ggaaagcggc     180
attagcgaag tgcgcagcga tcgcgataaa tttaccatta tgctggatgt gaaacatttt     240
agcccggaag atctgagcgt gaaaattatt gatgattttg tggaaattca tggcaaacat     300
agcgaacgcc aggatgatca tggctatatt agccgcgaat tcatcgccg ctatcgcctg      360
ccggcgaacg tggatcagag cgcgattacc tgcagcctga gcggcgatgg catgctgacc     420
tttagcggcc cgaaagtgcc gagcaacatg gatccgaccc atagcgaacg cccgattccg     480
gtgagccgcg aagaaaaacc gaccagcgcg ccgagcagc                            519
```

<210> SEQ ID NO 18
<211> LENGTH: 519
<212> TYPE: DNA
<213> ORGANISM: Rhea americana

<400> SEQUENCE: 18

```
atggatatta ccattcagca tccgtggttt aaacgcgcgc tgggcccgct gattccgagc      60
cgcctgtttg atcagttttt tggcgaaggc ctgctggaat atgatctgct gccgctgttt     120
agcagcacca ttagcccgta ttatcgccag agcctgtttc gcagcgtgct ggaaagcggc     180
attagcgaag tgcgcagcga tcgcgaaaaa tttaccatta tgctggatgt gaaacatttt     240
agcccggaag atctgagcgt gaaaattatt gatgattttg tggaaattca tggcaaacat     300
agcgaacgcc aggatgatca tggctatatt agccgcgaat tcatcgccg ctatcgcctg      360
ccgagcaacg tggatcagag cgcgattacc tgcagcctga gcagcgatgg catgctgacc     420
tttagcggcc cgaaagtgca ggcgaacatg gatccgagcc atagcgaacg cccgattccg     480
gtgagccgcg aagaaaaacc gaccagcgcg ccgagcagc                            519
```

<210> SEQ ID NO 19
<211> LENGTH: 447
<212> TYPE: DNA
<213> ORGANISM: Anas platyrhynchos

<400> SEQUENCE: 19

```
cgcgcgctgg gcccgctgat tccgagccgc ctgtttgatc agttttttgg cgaaggcctg      60
ctggaatatg atctgctgcc gctgtttagc agcaccatta gcccgtatta tcgccagagc     120
ctgtttcgca gcgtgctgga aagcggcatt agcgaagtgc gcagcgatcg cgataaattt     180
accattatgc tggatgtgaa acattttagc ccggaagatc tgagcgtgaa aattattgat     240
gattttgtgg aaattcatgg caaacatagc gaacgccagg atgatcatgg ctatattagc     300
cgcgaatttc atcgccgcta tcgcctgccg gcgaacgtgg atcagagcgc gattacctgc     360
agcctgagcg gcgatggcat gctgaccttt agcggcccga agtgccgag caacatggat      420
ccgacccata gcgaacgccc gattccg                                         447
```

<210> SEQ ID NO 20
<211> LENGTH: 522
<212> TYPE: DNA
<213> ORGANISM: Anas platyrhynchos

<400> SEQUENCE: 20

```
atggatatta ccattcataa cccgctgatt cgccgcccgc tgtttagctg gctggcgccg      60
agccgcattt ttgatcagat ttttggcgaa catctgcagg aaagcgaact gctgccggcg     120
agcccgagcc tgagcccgtt tctgatgcgc agcccgattt ttcgcatgcc gagctggctg     180
gaaaccggcc tgagcgaaat gcgcctggaa aaagataaat ttagcgtgaa cctggatgtg     240
aaacatttta gcccggaaga actgaaagtg aaagtgctgg cgatatggt ggaaattcat      300
ggcaaacatg aagaacgcca ggatgaacat ggctttattg cgcgcgaatt taaccgcaaa     360
tatcgcattc cggcggatgt ggatccgctg accattacca gcagcctgag cctggatggc     420
gtgctgaccg tgagcgcgcc gcgcaaacag agcgatgtgc cggaacgcag cattccgatt     480
acccgcgaag aaaaaccggc gattgcgggc gcgcagcgca aa                         522
```

<210> SEQ ID NO 21
<211> LENGTH: 519
<212> TYPE: DNA
<213> ORGANISM: Homo sapiens

<400> SEQUENCE: 21

```
atggatgtga ccattcagca tccgtggttt aaacgcaccc tgggcccgtt ttatccgagc      60
cgcctgtttg atcagttttt tggcgaaggc ctgtttgaat atgatctgct gccgtttctg     120
agcagcacca ttagcccgta ttatcgccag agcctgtttc gcaccgtgct ggatagcggc     180
attagcgaag tgcgcagcga tcgcgataaa tttgtgattt ttctggatgt gaaacatttt     240
agcccggaag atctgaccgt gaaagtgcag gatgattttg tggaaattca tggcaaacat     300
aacgaacgcc aggatgatca tggctatatt agccgcgaat tcatcgccg ctatcgcctg      360
ccgagcaacg tggatcagag cgcgctgagc tgcagcctga gcgcggatgg catgctgacc     420
ttttgcggcc cgaaaattca gaccggcctg gatgcgaccc atgcggaacg cgcgattccg     480
gtgagccgcg aagaaaaaacc gaccagcgcg ccgagcagc                            519
```

<210> SEQ ID NO 22
<211> LENGTH: 558
<212> TYPE: DNA
<213> ORGANISM: Drosophila melanogaster

<400> SEQUENCE: 22

```
atggcgaaca ttccgctgct gctgagcctg gcggatgatc tgggccgcat gagcatggtg      60
ccgtttatg aaccgtatta ttgccagcgc cagcgcaacc gtatctggc gctggtgggc       120
ccgatggaac agcagctgcg ccagctggaa aaacaggtgg gcgcgagcag cggcagcagc     180
ggcgcggtga gcaaaattgg caaagatggc tttcaggtgt gcatggatgt gagccatttt     240
aaaccgagcg aactggtggt gaaagtgcag ataacagcg tgctggtgga aggcaaccat      300
gaagaacgcg aagatgatca tggctttatt acccgccatt ttgtgcgccg ctatgcgctg     360
ccgccgggct atgaagcgga taagtgcgcg agcaccctga gcgcgatgg cgtgctgacc      420
attaaagtgc gaaaccgcc ggcgattgaa gataaaggca cgaacgcat tgtgcagatt       480
cagcaggtgg gcccggcgca tctgaacgtg aagaaaaacc cgaaagaagc ggtggaacag     540
gataacggca acgataaa                                                   558
```

<210> SEQ ID NO 23
<211> LENGTH: 522
<212> TYPE: DNA
<213> ORGANISM: Drosophila melanogaster

<400> SEQUENCE: 23

| | | | | | |
|---|---|---|---|---|---|
| atgcgcagcc | tgccgatgtt | ttggcgcatg | gcggaagaaa | tggcgcgcat | gccgcgcctg | 60 |
| agcagcccgt | tcatgcgtt | ttttcatgaa | ccgccggtgt | ggagcgtggc | gctgccgcgc | 120 |
| aactggcagc | atattgcgcg | ctggcaggaa | caggaactgg | cgccgccggc | gaccgtgaac | 180 |
| aaagatggct | ataaactgac | cctggatgtg | aaagattata | gcgaactgaa | agtgaaagtg | 240 |
| ctggatgaaa | gcgtggtgct | ggtggaagcg | aaaagcgaac | agcaggaagc | ggaacagggc | 300 |
| ggctatagca | gccgccattt | tctgggccgc | tatgtgctgc | cggatggcta | tgaagcggat | 360 |
| aaagtgagca | gcagcctgag | cgatgatggc | gtgctgacca | ttagcgtgcc | gaacccgccg | 420 |
| ggcgtgcagg | aaaccctgaa | agaacgcgaa | gtgaccattg | aacagaccgg | cgaaccggcg | 480 |
| aaaaaaagcg | cggaagaacc | gaaagataaa | accgcgagcc | ag | | 522 |

<210> SEQ ID NO 24
<211> LENGTH: 522
<212> TYPE: DNA
<213> ORGANISM: Anser cygnoides

<400> SEQUENCE: 24

| | | | | | |
|---|---|---|---|---|---|
| atggatatta | ccattcataa | cccgctgatt | cgccgcccgc | tgtttagctg | gctggcgccg | 60 |
| agccgcattt | tgatcagat | ttttggcgaa | catctgcagg | aaagcgaact | gctgccggcg | 120 |
| agcccgagcc | tgagcccgtt | tctgatgcgc | agcccgattt | ttcgcatgcc | gagctggctg | 180 |
| gaaaccggcc | tgagcgaaat | gcgcctggaa | aaagataaat | ttagcgtgaa | cctggatgtg | 240 |
| aaacatttta | gcccggaaga | actgaaagtg | aaagtgctgg | gcgatatggt | ggaaattcat | 300 |
| ggcaaacatg | aagaacgcca | ggatgaacat | ggctttattg | cgcgcgaatt | taaccgcaaa | 360 |
| tatcgcattc | cggcggatgt | ggatccgctg | accattacca | gcagcctgag | cctggatggc | 420 |
| gtgctgaccg | tgagcgcgcc | gcgcaaacag | agcgatgtgc | cggaacgcag | cattccgatt | 480 |
| acccgcgaag | aaaaaccggc | gattgcgggc | gcgcagcgca | aa | | 522 |

<210> SEQ ID NO 25
<211> LENGTH: 519
<212> TYPE: DNA
<213> ORGANISM: Artificial Sequence
<220> FEATURE:
<223> OTHER INFORMATION: artificial polynucleotide

<400> SEQUENCE: 25

| | | | | | |
|---|---|---|---|---|---|
| atggatatta | ccattcagca | tccgtggttt | aaacgcgcgc | tgggcccgct | gattccggaa | 60 |
| cgcctgtttg | atcagttttt | tggcagcggc | ctgctgagct | atgatctgct | gccgctgttt | 120 |
| gaagaaacca | ttgaaccgta | ttatcgccag | gaactgtttc | gcgaagtgct | gagcgaaggc | 180 |
| attgaaagcg | tgcgcgaaga | tcgcgataaa | tttaccatta | tgctggatgt | gaaacatttt | 240 |
| gaaccgagcg | atctgaagt | gaaaattatt | gatgattttg | tgagcattca | tggcaaacat | 300 |
| gaaagccgcc | aggatgatca | tggctatatt | gaacgcagct | tcatcgccg | ctatcgcctg | 360 |
| ccggcgaacg | tggatcagga | agcgattacc | tgcgaactgg | aaggcgatgg | catgctgacc | 420 |
| tttgaaggcc | cgaaagtgcc | ggaaaacatg | gatccgaccc | atgaaagccg | cccgattccg | 480 |
| gtggaacgca | gcagcaaacc | gaccgaagcg | ccggaagaa | | | 519 |

<210> SEQ ID NO 26
<211> LENGTH: 519
<212> TYPE: DNA
<213> ORGANISM: Artificial Sequence
<220> FEATURE:
<223> OTHER INFORMATION: artificial polynucleotide

<400> SEQUENCE: 26

```
atggatatta ccattcagca tccgtggttt aaacgcgcgc tgggcccgct gattccggaa      60
cgcctgtttg atcagttttt tggcagcggc ctgctgagct atgatctgct gccgctgttt     120
gaagaaacca ttgaaccgta ttatcgccag gaactgtttc gcgaagtgct gagcgaaggc     180
attgaaagcg tgcgcgaaga tcgcagcaaa tttaccatta tgctggatgt gaaacatttt     240
gaaccgagcg atctggaagt gaaaattatt gatgattttg tgagcattca tggcaaacat     300
gaaagccgcc aggatgatca tggctatatt gaacgcagct tcatcgccg ctatcgcctg       360
ccggaaaacg tggatcagga agcgattacc tgcgaactgg aagaagatgg catgctgacc     420
tttgaaggcc gaaagtgca ggcgaacatg gatccggaac atgaaagccg cccgattccg      480
gtggaacgca gcagcaaacc gaccgaagcg ccggaagaa                            519
```

<210> SEQ ID NO 27
<211> LENGTH: 447
<212> TYPE: DNA
<213> ORGANISM: Artificial Sequence
<220> FEATURE:
<223> OTHER INFORMATION: artificial polynucleotide

<400> SEQUENCE: 27

```
cgcgcgctgg gcccgctgat tccggaacgc ctgtttgatc agttttttgg cagcggcctg      60
ctgagctatg atctgctgcc gctgtttgaa gaaaccattg aaccgtatta tcgccaggaa     120
ctgtttcgcg aagtgctgag cgaaggcatt gaaagcgtgc gcgaagatcg cgataaattt     180
accattatgc tggatgtgaa acattttgaa ccgagcgatc tggaagtgaa aattattgat     240
gattttgtga gcattcatgg caaacatgaa agccgccagg atgatcatgg ctatattgaa     300
cgcagctttc atcgccgcta tcgcctgccg gcgaacgtgg atcaggaagc gattacctgc     360
gaactggaag cgatggcat gctgaccttt gaaggcccga agtgccgga aacatggat        420
ccgacccatg aaagccgccc gattccg                                         447
```

<210> SEQ ID NO 28
<211> LENGTH: 522
<212> TYPE: DNA
<213> ORGANISM: Artificial Sequence
<220> FEATURE:
<223> OTHER INFORMATION: artificial polynucleotide

<400> SEQUENCE: 28

```
atgagcatta ccattcataa cccgctgatt cgccgcccgc tgtttgattg gctggcgccg      60
gatcgcattt ttagccagat ttttggcgaa catctgcagg aagatgaact gctgccggcg     120
gatccggatc tggatccgtt tctgatgcgc gatccgattt ttcgcatgcc ggattggctg     180
gaaaccggcc tggatgaaat gcgcctggaa aaaagcaaat tgatgtgaa cctgagcgtg      240
aaacattttg atccggaaga actgaaagtg aaagtgctgg gcagcatggt ggaaattcat     300
ggcaaacatg aagaacgcca gagcgaacat ggctttattg cgcgcgaatt taaccgcaaa     360
tatcgcattc cggcgagcgt gagcccgctg accattaccg atgatctgga tctgagcggc     420
```

| gtgctgaccg tggatgcgcc gcgcaaacag atagcgtgc cggaacgcga tattccgatt | 480 |
| acccgcgaag aaaaaccggc gattgcgggc gcgcagcgca aa | 522 |

<210> SEQ ID NO 29
<211> LENGTH: 519
<212> TYPE: DNA
<213> ORGANISM: Artificial Sequence
<220> FEATURE:
<223> OTHER INFORMATION: artificial polynucleotide

<400> SEQUENCE: 29

| atggatgtga ccattcagca tccgtggttt aaacgcaccc tgggcccgtt ttatccggaa | 60 |
| cgcctgtttg atcagttttt tggcagcggc ctgtttagct atgatctgct gccgtttctg | 120 |
| gaagaaacca ttgaaccgta ttatcgccag gaactgtttc gcaccgtgct ggatgaaggc | 180 |
| attgaaagcg tgcgcgaaga tcgcgataaa tttgtgattt ttctggatgt gaaacatttt | 240 |
| gaaccgagcg atctgaccgt gaaagtgcag gatgattttg tgagcattca tggcaaacat | 300 |
| aacagccgcc aggatgatca tggctatatt gaacgcagct tcatcgccg ctatcgcctg | 360 |
| ccggaaaacg tggatcagga agcgctggaa tgcgaactgg aagcggatgg catgctgacc | 420 |
| ttttgcggcc cgaaaattca gaccggcctg gatgcgaccc atgcgagccg cgcgattccg | 480 |
| gtggaacgca gcagcaaacc gaccgaagcg ccggaagaa | 519 |

<210> SEQ ID NO 30
<211> LENGTH: 558
<212> TYPE: DNA
<213> ORGANISM: Artificial Sequence
<220> FEATURE:
<223> OTHER INFORMATION: artificial polynucleotide

<400> SEQUENCE: 30

| atggcgaaca ttccgctgct gctgagcctg gcggtggtgc tgggccgcat gagcatggat | 60 |
| ccgtttatg aaccgtatta ttgccagcgc cagcgcaacc cgtatctggc gctggatggc | 120 |
| ccgatggaac agcagctgcg ccagctggaa aaacaggatg gcgcgagcag cggcagcagc | 180 |
| ggcgcggata gcaaaattgg caaagtgggc tttcaggatt gcatggtgga tagccatttt | 240 |
| aaaccgagcg aactggatga taaagatcag gtgaacagcg atctggatga aggcaaccat | 300 |
| gaagaacgcg aagtggtgca tggctttatt acccgccatt ttgatcgccg ctatgcgctg | 360 |
| ccgccgggct atgaagcggt gaaagatgcg agcaccctga gcagcgtggg cgatctgacc | 420 |
| attaaagatc cgaaaccgcc ggcgattgaa gtgaaaggca cgaacgcat tgatcagatt | 480 |
| cagcaggatg gcccggcgca tctgaacgat aaagaaaacc cgaaagaagc ggatgaacag | 540 |
| gtgaacggca acgtgaaa | 558 |

<210> SEQ ID NO 31
<211> LENGTH: 522
<212> TYPE: DNA
<213> ORGANISM: Artificial Sequence
<220> FEATURE:
<223> OTHER INFORMATION: artificial polynucleotide

<400> SEQUENCE: 31

| atgcgcctga gcccgatgtt ttggcgcatg gcggaagaaa tggcgcgcat gccgcgcagc | 60 |
| ctgctgccgt tcatgcgtt ttttcatgaa ccgccggatt ggctggatgc gagcccgcgc | 120 |
| aactggcagc atattgcgcg ctggcaggaa caggaaagcg cgccgccggc gaccgataac | 180 |
| aaagtgggct ataaaagcac cagcgtggat aaagtgtatc tggaaagcaa agataaagat | 240 |

```
agcgtggaac tggatgatag cgatgaagcg aaactggaac agcaggaagc ggaacagggc    300
ggctatctgc tgcgccattt tagcggccgc tatgatagcc cggtgggcta tgaagcggtg    360
aaagatctgc tgctgagcct ggtggtgggc gatagcacca ttctggatcc gaacccgccg    420
ggcgatcagg aaaccagcaa agaacgcgaa gataccattg aacagaccgg cgaaccggcg    480
aaaaaactgg cggaagaacc gaaagtgaaa accgcgctgc ag                       522

<210> SEQ ID NO 32
<211> LENGTH: 522
<212> TYPE: DNA
<213> ORGANISM: Artificial Sequence
<220> FEATURE:
<223> OTHER INFORMATION: artificial polynucleotide

<400> SEQUENCE: 32
atgagcatta ccattcataa cccgctgatt cgccgcccgc tgtttgattg gctggcgccg     60
gatcgcattt ttagccagat ttttggcgaa catctgcagg aagatgaact gctgccggcg    120
gatccggatc tggatccgtt tctgatgcgc gatccgattt ttcgcatgcc ggattggctg    180
gaaaccggcc tggatgaaat cgcctggaa aaaagcaaat ttgatgtgaa cctgagcgtg     240
aaacattttg atccggaaga actgaaagtg aaagtgctgg cagcatggt ggaaattcat     300 ggcaaacatg aagaacgcca gagcgaacat ggctttattg cgcgcgaatt taaccgcaaa    360
tatcgcattc cggcgagcgt gagcccgctg accattaccg atgatctgga tctgagcggc    420
gtgctgaccg tggatgcgcc gcgcaaacag gatagcgtgc cggaacgcga tattccgatt    480
acccgcgaag aaaaaccggc gattgcgggc gcgcagcgca aa                      522

<210> SEQ ID NO 33
<211> LENGTH: 50
<212> TYPE: DNA
<213> ORGANISM: Anser cygnoides

<400> SEQUENCE: 33 gggggggcata tggacattac catccagcac ccctggttca agcgcgctct               50

<210> SEQ ID NO 34
<211> LENGTH: 39
<212> TYPE: DNA
<213> ORGANISM: Anser cygnoides

<400> SEQUENCE: 34 gggggggaagc ttttactcct caggcgcctc ggtgggctt                           39

<210> SEQ ID NO 35
<211> LENGTH: 32
<212> TYPE: DNA
<213> ORGANISM: Artificial Sequence
<220> FEATURE:
<223> OTHER INFORMATION: artificial polynucleotide

<400> SEQUENCE: 35
cctctgttcg aggagactat cgagccctac ta                                   32

<210> SEQ ID NO 36
<211> LENGTH: 32
<212> TYPE: DNA
<213> ORGANISM: Artificial Sequence
<220> FEATURE:
<223> OTHER INFORMATION: artificial polynucleotide
```

```
<400> SEQUENCE: 36
tagtagggct cgatagtctc ctcgaacaga gg                                    32

<210> SEQ ID NO 37
<211> LENGTH: 64
<212> TYPE: DNA
<213> ORGANISM: Artificial Sequence
<220> FEATURE:
<223> OTHER INFORMATION: artificial polynucleotide

<400> SEQUENCE: 37
accggcagga gctgttccgc gaggtgctgt cggagggcat tgagtcggtg agggaggacc      60
ggga                                                                  64

<210> SEQ ID NO 38
<211> LENGTH: 64
<212> TYPE: DNA
<213> ORGANISM: Artificial Sequence
<220> FEATURE:
<223> OTHER INFORMATION: artificial polynucleotide

<400> SEQUENCE: 38
tcccggtcct ccctcaccga ctcaatgccc tccgacagca cctcgcggaa cagctcctgc      60
cggt                                                                  64

<210> SEQ ID NO 39
<211> LENGTH: 52
<212> TYPE: DNA
<213> ORGANISM: Artificial Sequence
<220> FEATURE:
<223> OTHER INFORMATION: artificial polynucleotide

<400> SEQUENCE: 39
actatgctgg acgtaaaaca ctttgagcct tcggacctgg aggtgaagat ta              52

<210> SEQ ID NO 40
<211> LENGTH: 52
<212> TYPE: DNA
<213> ORGANISM: Artificial Sequence
<220> FEATURE:
<223> OTHER INFORMATION: artificial polynucleotide

<400> SEQUENCE: 40
taatcttcac ctccaggtcc gaaggctcaa agtgttttac gtccagcatg at              52

<210> SEQ ID NO 41
<211> LENGTH: 33
<212> TYPE: DNA
<213> ORGANISM: Artificial Sequence
<220> FEATURE:
<223> OTHER INFORMATION: artificial polynucleotide

<400> SEQUENCE: 41
aagattatcg acgactttgt gtcgatccat ggc                                  33

<210> SEQ ID NO 42
<211> LENGTH: 33
<212> TYPE: DNA
<213> ORGANISM: Artificial Sequence
<220> FEATURE:
<223> OTHER INFORMATION: artificial polynucleotide

<400> SEQUENCE: 42
gccatggatc gacacaaagt cgtcgataat ctt                                  33
```

<210> SEQ ID NO 43
<211> LENGTH: 57
<212> TYPE: DNA
<213> ORGANISM: Artificial Sequence
<220> FEATURE:
<223> OTHER INFORMATION: artificial polynucleotide

<400> SEQUENCE: 43
ggcaagcacg agtcgagaca ggacgaccac ggctacatcg agcggtcgtt tcaccgc    57

<210> SEQ ID NO 44
<211> LENGTH: 57
<212> TYPE: DNA
<213> ORGANISM: Artificial Sequence
<220> FEATURE:
<223> OTHER INFORMATION: artificial polynucleotide

<400> SEQUENCE: 44
gcggtgaaac gaccgctcga tgtagccgtg gtcgtcctgt ctcgactcgt gcttgcc    57

<210> SEQ ID NO 45
<211> LENGTH: 41
<212> TYPE: DNA
<213> ORGANISM: Artificial Sequence
<220> FEATURE:
<223> OTHER INFORMATION: artificial polynucleotide

<400> SEQUENCE: 45
gcggaccagg aggccatcac ctgcgagctg gagggcgacg g    41

<210> SEQ ID NO 46
<211> LENGTH: 41
<212> TYPE: DNA
<213> ORGANISM: Artificial Sequence
<220> FEATURE:
<223> OTHER INFORMATION: artificial polynucleotide

<400> SEQUENCE: 46
ccgtcgccct ccagctcgca ggtgatggcc tcctggtcca c    41

<210> SEQ ID NO 47
<211> LENGTH: 54
<212> TYPE: DNA
<213> ORGANISM: Artificial Sequence
<220> FEATURE:
<223> OTHER INFORMATION: artificial polynucleotide

<400> SEQUENCE: 47
ttcgaccagt ttttcggatc gggtctgctg tcgtatgacc tgctgcctct gttc    54

<210> SEQ ID NO 48
<211> LENGTH: 39
<212> TYPE: DNA
<213> ORGANISM: Artificial Sequence
<220> FEATURE:
<223> OTHER INFORMATION: artificial polynucleotide

<400> SEQUENCE: 48
ggggaccttg gggccctcga aggtcagcat gccgtcgcc    39

<210> SEQ ID NO 49
<211> LENGTH: 57
<212> TYPE: DNA
<213> ORGANISM: Artificial Sequence
<220> FEATURE:

```
<223> OTHER INFORMATION: artificial polynucleotide

<400> SEQUENCE: 49
ttcaagcgcg ctctgggacc cctgattcca gagcgtctgt tcgaccagtt tttcgga      57

<210> SEQ ID NO 50
<211> LENGTH: 55
<212> TYPE: DNA
<213> ORGANISM: Artificial Sequence
<220> FEATURE:
<223> OTHER INFORMATION: artificial polynucleotide

<400> SEQUENCE: 50
cacggggatg ggcctcgact cgtgggtggg gtccatgttc tcggggacct tgggg        55

<210> SEQ ID NO 51
<211> LENGTH: 18
<212> TYPE: DNA
<213> ORGANISM: Artificial Sequence
<220> FEATURE:
<223> OTHER INFORMATION: artificial polynucleotide

<400> SEQUENCE: 51
atggacatta ccatccag                                                 18

<210> SEQ ID NO 52
<211> LENGTH: 60
<212> TYPE: DNA
<213> ORGANISM: Artificial Sequence
<220> FEATURE:
<223> OTHER INFORMATION: artificial polynucleotide

<400> SEQUENCE: 52
aagcttttac tcctcaggcg cctcggtggg cttcgacgac cgctccacgg ggatgggcct   60
```